US010480009B2

(12) United States Patent
Lu et al.

(10) Patent No.: US 10,480,009 B2
(45) Date of Patent: Nov. 19, 2019

(54) BIOLOGICAL STATE MACHINES

(71) Applicant: Massachusetts Institute of Technology, Cambridge, MA (US)

(72) Inventors: Timothy Kuan-Ta Lu, Cambridge, MA (US); Nathaniel B. Roquet, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 9 days.

(21) Appl. No.: 15/283,162

(22) Filed: Sep. 30, 2016

(65) Prior Publication Data

US 2017/0096680 A1   Apr. 6, 2017

Related U.S. Application Data

(60) Provisional application No. 62/348,601, filed on Jun. 10, 2016, provisional application No. 62/256,829, filed on Nov. 18, 2015, provisional application No. 62/235,776, filed on Oct. 1, 2015.

(51) Int. Cl.
| | | |
|---|---|---|
| *C12N 15/63* | (2006.01) | |
| *C12N 15/85* | (2006.01) | |
| *G16B 30/00* | (2019.01) | |
| *C12N 9/16* | (2006.01) | |

(52) U.S. Cl.
CPC ............... *C12N 15/85* (2013.01); *C12N 9/16* (2013.01); *G16B 30/00* (2019.02); *C12N 2800/107* (2013.01); *C12N 2800/30* (2013.01)

(58) Field of Classification Search
None
See application file for complete search history.

(56) References Cited

U.S. PATENT DOCUMENTS

2014/0315310 A1   10/2014   Lu et al.

OTHER PUBLICATIONS

Yang et al. Nature Method 2011, vol. 11, No. 12, pp. 1261-1266, and supplemental Figures.*
Roquet et al., Synthetic recombinase-based state machines in living cells. Science. Jul. 22, 2016;353(6297):aad8559. doi: 10.1126/science.aad8559. Epub Jul. 21, 2016.
Rutherford et al., The ins and outs of serine integrase site-specific recombination. Curr Opin Struct Biol. Feb. 2014;24:125-31. doi:10.1016/j.sbi.2014.01.003. Epub Feb. 11, 2014.
Suzuki et al., A novel system for simultaneous or sequential integration of multiple gene-loading vectors into a defined site of a human artificial chromosome. PLoS One. Oct. 10, 2014;9(10):e110404. doi:10.1371/journal.pone.0110404. eCollection 2014.
Xu et al., Accuracy and efficiency define Bxbl integrase as the best of fifteen candidate serine recombinases for the integration of DNA into the human genome. BMC Biotechnol. Oct. 20, 2013;13:87. doi: 10.1186/1472-6750-13-87.
Yang et al., Permanent genetic memory with >1-byte capacity. Nat Methods. Dec. 2014;11(12):1261-6. doi: 10.1038/nmeth.3147. Epub Oct. 26, 2014.
Auslander et al., Programmable single-cell mammalian biocomputers. Nature. Jul. 5, 2012;487(7405):123-7. doi: 10.1038/nature11149.
Benenson. Biomolecular computing systems: principles, progress and potential. Nat Rev Genet. Jun. 12, 2012;13(7):455-68. doi: 10.1038/nrg3197.
Bonnet et al., Amplifying genetic logic gates. Science. May 3, 2013;340(6132):599-603. doi: 10.1126/science.1232758. Epub Mar. 28, 2013.
Bonnet et al., Rewritable digital data storage in live cells via engineered control of recombination directionality. Proc Natl Acad Sci U S A. Jun. 5, 2012;109(23):8884-9. doi: 10.1073/pnas.1202344109. Epub May 21, 2012.
Callura et al., Tracking, tuning, and terminating microbial physiology using synthetic riboregulators. Proc Natl Acad Sci U S A. Sep. 7, 2010;107(36):15898-903. doi: 10.1073/pnas.1009747107. Epub Aug. 16, 2010.
Friedland et al., Synthetic gene networks that count. Science. May 29, 2009;324(5931):1199-202. doi:10.1126/science.1172005.
Ham et al., A tightly regulated inducible expression system utilizing the fim inversion recombination switch. Biotechnol Bioeng. May 5, 2006;94(1):1-4.
Ham et al., Design and construction of a double inversion recombination switch for heritable sequential genetic memory. PLoS One. Jul. 30, 2008;3(7):e2815. doi:10.1371/journal.pone.0002815.
Hasty et al., Engineered gene circuits. Nature. Nov. 14, 2002;420(6912):224-30.
Hsiao et al., A population-based temporal logic gate for timing and recording chemical events. bioRxiv. 2015. doi: 10.1101/029967.
Moon et al., Genetic programs constructed from layered logic gates in single cells. Nature. Nov. 8, 2012;491(7423):249-53. doi: 10.1038/nature11516. Epub Oct. 7, 2012.
Oishi et al., Framework for engineering finite state machines in gene regulatory networks. ACS Synth Biol. Sep. 19, 2014;3(9):652-65. doi:10.1021/sb4001799. Epub Mar. 5, 2014.
Prochazka et al., Highly modular bow-tie gene circuits with programmable dynamic behaviour. Nat Commun. Oct. 14, 2014;5:4729. doi: 10.1038/ncomms5729.
Regot et al., Distributed biological computation with multicellular engineered networks. Nature. Jan. 13, 2011;469(7329):207-11. doi:10.1038/nature09679. Epub Dec. 8, 2010.
Siuti et al., Synthetic circuits integrating logic and memory in living cells. Nat Biotechnol. May 2013;31(5):448-52. doi: 10.1038/nbt.2510. Epub Feb. 10, 2013.

(Continued)

*Primary Examiner* — Celine X Qian
(74) *Attorney, Agent, or Firm* — Wolf, Greenfield & Sacks, P.C.

(57) ABSTRACT

Provided herein are recombinase-based frameworks for building state machines in vitro and in vivo by using chemically controlled DNA excision and inversion operations to encode state in DNA sequence.

14 Claims, 49 Drawing Sheets

Specification includes a Sequence Listing.

(56) References Cited

OTHER PUBLICATIONS

Tamsir et al., Robust multicellular computing using genetically encoded NOR gates and chemical 'wires'. Nature. Jan. 13, 2011;469(7329):212-5. doi:10.1038/nature09565. Epub Dec. 8, 2010.
Teo et al., Development and characterization of AND-gate dynamic controllers with a modular synthetic GAL1 core promoter in *Saccharomyces cerevisiae*. Biotechnol Bioeng. Jan. 2014;111(1):144-51. doi: 10.1002/bit.25001. Epub Aug. 12, 2013.
Wang et al., Engineering modular and orthogonal genetic logic gates for robust digital-like synthetic biology. Nat Commun. Oct. 18, 2011;2:508. doi: 10.1038/ncomms1516.
Win et al., Higher-order cellular information processing with synthetic RNA devices. Science. Oct. 17, 2008;322(5900):456-60. doi: 10.1126/science.1160311.
PCT/US2016/054645, Apr. 12, 2008, International Preliminary Report on Patentability.
Brown et al., Serine recombinases as tools for genome engineering. Methods. Apr. 2011:53(4):372-9 doi: 10.1016/j.ymeth.2010.12.031. Epub Dec. 30, 2010.
Purcell et al., Synthetic analog and digital circuits for cellular computation and memory. Curr Opin Biotechnol. Oct. 2014;29:146-55. doi:10.1016/j.copbio.2014.04.009. Epub May 8, 2014.
Siuti et al., Engineering genetic circuits that compute and remember. Nat Protoc. 2014;9(6):1292-300. doi: 10.1038/nprot.2014.089. Epub May 8, 2014.

\* cited by examiner

Inputs: { A, B }
States: { S1, S2, S3, S4, S5 }

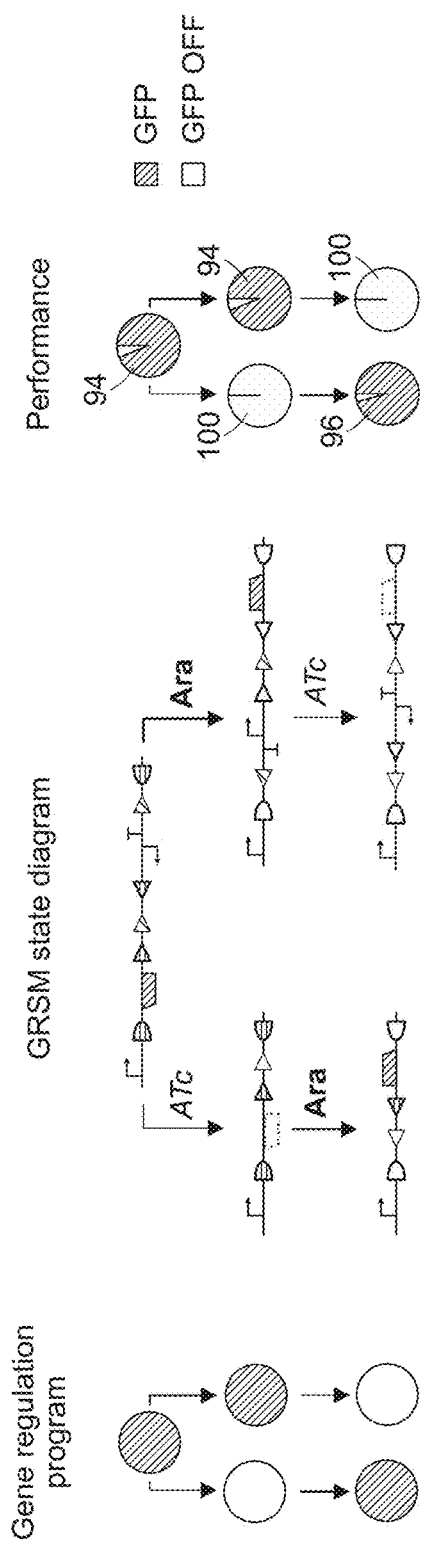
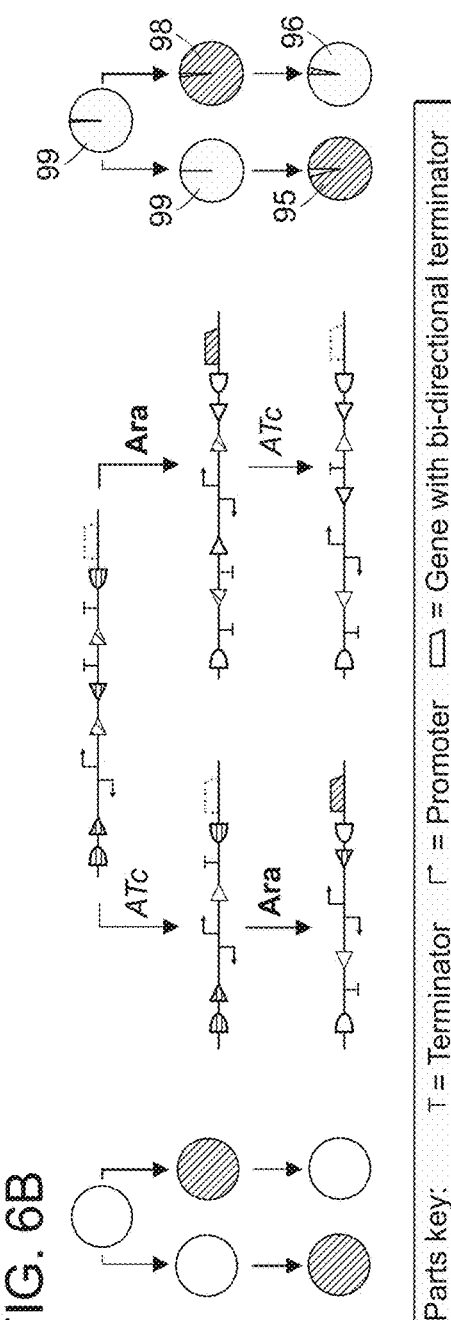
FIG. 6A
FIG. 6B

Parts key: T = Terminator  ⌐ = Promoter  ▭ = Gene with bi-directional terminator

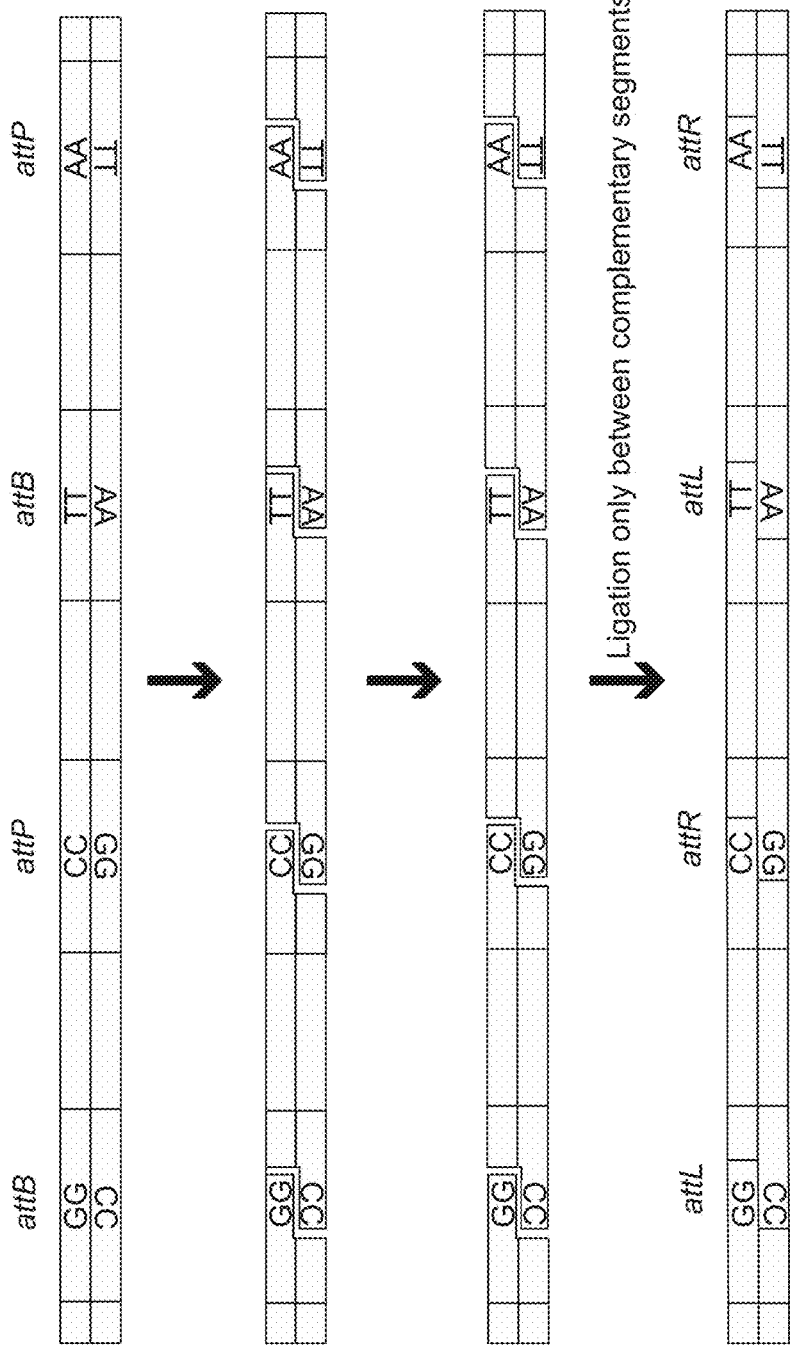

Parts key:  ⌐ = Promoter   ⊂⊃ = Gene with bi-directional terminator

■ None
▨ GFP
▤ BFP
▥ RFP
▨ GFP + BFP
▨ GFP + RFP
▥ RFP + BFP
☐ GFP + BFP + RFP

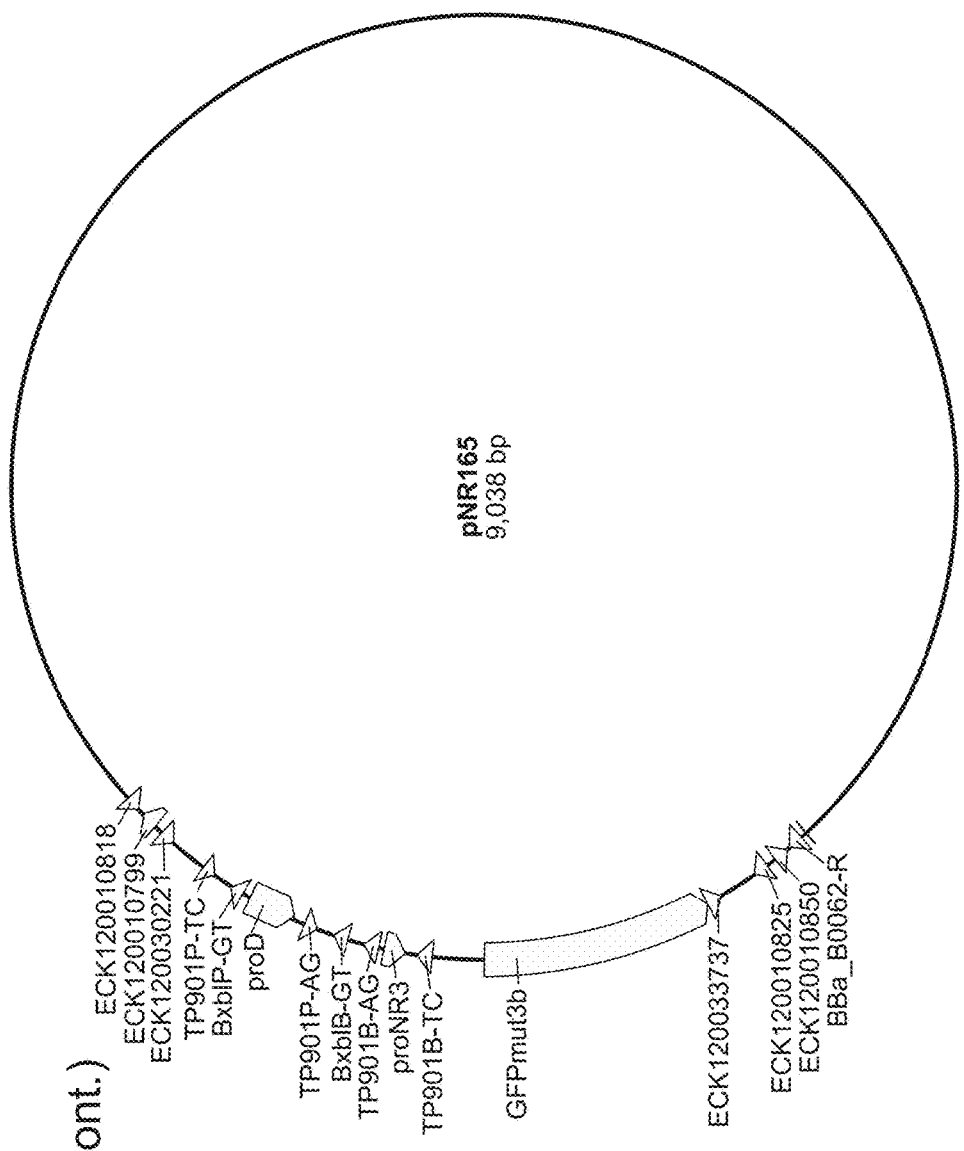

| Number of inputs | Register design | Number of states |
|---|---|---|
| 1 | | 2 |
| 2 | | 5 |
| 3 | | 16 |
| 4 | | 65 |
| 5 | | 326 |
| 6 | | 1957 |
| 7 | | 13700 |

FIG. 22

| Parts | Database ID | Palindromic? | Terminator read-through? | Promoter read-through? |
|---|---|---|---|---|
| | 1 | N | N | N |
| | 2 | N | N | N |
| | 3 | N | N | N |
| | 4 | Y | N | N |
| (empty) | 5 | Y | N | N |
| | 6 | Y | N | N |
| | 7 | N | Y | N |
| | 8 | Y | N | N |
| | 9 | N | N | Y |
| | 10 | N | N | Y |
| | 11 | N | N | Y |
| | 12 | N | N | Y |
| | 13 | Y | N | Y |
| | 14 | N | N | N |
| | 15 | N | N | N |
| | 16 | N | N | N |
| | 17 | N | N | N |
| | 18 | N | N | N |
| | 19 | Y | N | N |
| | 20 | Y | N | N |
| | 21 | Y | N | N |
| | 22 | N | N | Y |
| | 23 | N | N | Y |
| | 24 | N | N | Y |
| | 25 | Y | N | Y |

Parts Key: T = Terminator  T = Optional terminator  ⌐ = Promoter  ▭ = Gene with bi-directional terminator

FIG. 23

SEQUENCE LISTING

```
<160> NUMBER OF SEQ ID NOS: 70

<210> SEQ ID NO 1
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 1
atatagtgaa caaggattaa                                              20

<210> SEQ ID NO 2
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 2
ataggttaaa agccagacat                                              20

<210> SEQ ID NO 3
<211> LENGTH: 1503
<212> TYPE: DNA
<213> ORGANISM: Artificial Sequence
<220> FEATURE:
<223> OTHER INFORMATION: Synthetic Polynucleotide

<400> SEQUENCE: 3
gtgagagccc tggtagtcat ccgcctgtcc cgcgtcaccg atgctacgac ttcaccggag     60
cgtcagctgg agtcttgcca gcagctctgc gcccagcgcg gctgggacgt cgtcggggta    120
gcggaggatc tggacgtctc cggggcggtc gatccgttcg accggaagcg cagaccgaac    180
ctggcccggt ggctagcgtt cgaggagcaa ccgtttgacg tgatcgtggc gtaccgggta    240
gatcggttga cccgatcgat ccggcatctt cagcagctgt ccactgggc cgaggaccac    300 aagaagctgg tcgtctccgc gaccgaagcg cacttcgata cgacgacgcc gtttgcggcg    360
```

```
gtcgtcatcg cgcttatggg aacggtggcg cagatggaat tagaagcgat caaagagcgg      420
aaccgttcgg ctgcgcattt caatatccgc gccgggaaat accgaggatc cctgccgccg      480
tggggatacc tgcctacgcg cgtggacggg gagtggcggc tggtgccgga ccctgtgcag      540
cgagagcgca tcctcgaggt gtatcaccgc gtcgtcgaca accacgagcc gctgcatctg      600
gtggcccacg acctgaaccg gcgtggtgtc ctgtcgccga aggactactt cgcgcagctg      660
caaggccgcg agccgcaggg ccgggagtgg tcggctaccg cgctgaagcg atcgatgatc      720
tccgaggcga tgctcgggta cgcgactctg aacggtaaga ccgtccgaga cgacgacgga      780
gccccgctgg tgcgggctga gccgatcctg accgtgagc agctgaggc gctgcgcgcc        840 gagctcgtga agacctcccg ggcgaagccc gcggtgtcta ccccgtcgct gctgctgcgg      900
gtgttgttct gcgcggtgtg cggggagccc gcgtacaagt cgccgggggg aggacgtaag      960
cacccgcgct accgctgccg ctcgatgggg ttcccgaagc actgcgggaa cggcacggtg     1020
gcgatggccg agtgggacgc gttctgcgag gagcaggtac tggatctgct cggggacgcg     1080
gagcgtctgg agaaagtctg ggtagcgggc tcggactccg cggtcgaact cgcggaggtg     1140
aacgcggagc tggtggacct gacgtcgctg atcggctccc cggcctaccg ggcgggctct     1200
ccgcagcgag aagcactgga tgcccgtatt gcggcgctgg ccgcgcggca agaggagctg     1260
gagggcctgg aggctcgccc gtctggctgg gagtggcgcg agaccgggca gcggttcggg     1320
gactggtggc gggagcagga caccgcggca agaacacct ggcttcggtc gatgaacgtt      1380
cggctgacgt tcgacgtccg cggcgggctg actcgcacga tcgacttcgg ggatcttcag     1440
gagtacgagc agcatctcag gctcggcagc gtggtcgaac ggctacacac cgggatgtcg     1500
taa                                                                   1503

<210> SEQ ID NO 4
<211> LENGTH: 1527
<212> TYPE: DNA
<213> ORGANISM: Artificial Sequence
<220> FEATURE:
<223> OTHER INFORMATION: Synthetic Polynucleotide

<400> SEQUENCE: 4
atgaaacatc atcaccatca ccaccaggcc ggcactaaga agtagcaat ctatacacga        60 gtatccacta ctaaccaagc agaggaaggc ttctcaattg atgagcaaat tgaccgttta      120
acaaaatatg ctgaagcaat ggggtggcaa gtatctgata cttatactga tgctggtttt      180
tcagggccaa acttgaacg cccagcaatg caaagattaa tcaacgatat cgagaataaa      240
gcttttgata cagttcttgt atataagcta gaccgccttt cacgtagtgt aagagatact      300
ctttatcttg ttaaggatgt gttcacaaaa aataaaatag actttatctc gcttaatgaa      360
agtattgata cttcttctgc tatgggtagc ttgtttctca ctattctttc tgcaattaat      420
gagtttgaaa gagagaatat aaaagaacgc atgactatgg gtaaactagg gcgagcgaaa      480
tctggtaagt ctatgatgtg gactaagaca gcttttgggt attaccacaa cagaaagaca      540
ggtatattag aaattgttcc tttacaagct acaatagttg aacaaatatt cactgattat      600
ttatcaggaa tatcacttac aaaattaaga gataaactca atgaatctgg acacatcggt      660
aaagatatac cgtggtctta tcgtacccta agacaaacac ttgataatcc agtttactgt      720
ggttatatca aatttaagga cagcctattt gaaggtatgc acaaaccaat tatcccttat      780
gagacttatt taaagttca aaagagcta aagaaagac aacagcagac ttatgaaga       840 aataacaacc ctagaccttt ccaagctaaa tatatgctgt cagggatggc aaggtgcggt      900
```

```
tactgtggag cacctttaaa aattgttctt ggccacaaaa gaaaagatgg aagccgcact      960
atgaaatatc actgtgcaaa tagatttcct cgaaaaacaa aaggaattac agtatataat     1020
gacaataaaa agtgtgattc aggaacttat gatttaagta atttagaaaa tactgttatt     1080
gacaacctga ttggatttca agaaaataat gactccttat tgaaaattat caatggcaac     1140
aaccaaccta ttcttgatac ttcgtcattt aaaaagcaaa tttcacagat cgataaaaaa     1200
atacaaaaga actctgattt gtacctaaat gattttatca ctatggatga gttgaaagat     1260
cgtactgatt cccttcaggc tgagaaaaag ctgcttaaag ctaagattag cgaaaataaa     1320
tttaatgact ctactgatgt ttttgagtta gttaaaactc agttgggctc aattccgatt     1380
aatgaactat catatgataa taaaaagaaa atcgtcaaca accttgtatc aaaggttgat     1440
gttactgctg ataatgtaga tatcatattt aaattccaac tcgctaccgg tgctgctaag     1500
gacgaaaact acgctctggc tgcttaa                                          1527

<210> SEQ ID NO 5
<211> LENGTH: 1359
<212> TYPE: DNA
<213> ORGANISM: Artificial Sequence
<220> FEATURE:
<223> OTHER INFORMATION: Synthetic Polynucleotide

<400> SEQUENCE: 5
atgaaggcag ctatttatat acgtgtttct actcaagagc aagtagaaaa ttattcaata       60
caagctcaaa ctgaaaaact aacaggattg tgccgctcga aggactggga cgtatacgat      120
attttcattg acggcggata ctccggctca aatatgaatc gtcccgcatt aaatgaaatg      180
ctaagtaaac tacacgaaat tgatgctgta gtcgtatatc gattagacag actatcccgc      240
tcacaaagag acacaataac gcttattgaa gaatacttct taaaaaacaa tgtagagttt      300
gttagtttgt ctgaaacgct tgatactagt tccccttttcg gtcgtgcaat gattggtata      360
ttatcagtat tcgcacagct agagcgcgaa acaatccgag atcgtatggt gatggggaaa      420
attaagcgta ttgaagcagg tcttccgtta acaactgcga aggtagaac gttcggctat       480 gatgttatag atacaaaatt atacattaat gaagaagaag caaacagtt acaactgatt       540 tatgatattt cgaagaaga acaaagtata acttttttac agaaaagact aaaaaaatta       600
ggctttaaag ttagaacata taatcgctat aacaactggc taactaatga tttgtattgt      660
ggttatgttt catataaaga taaagttcat gtaaaaggta ttcatgaacc tatcatcagt      720
gaagagcaat tctatagagt tcaagaaata tttactcgta tgggtaaaaa tccgaacatg      780
aatagagatt cagcatcgtt gctaaataat ttagtagttt gtagtaaatg cgggttaggc      840
tttgttcatc gtagaaaaga tacaatgtcg cgtggtaaaa aatatcatta tagatattat      900
agttgcaaga cttataaaca tactcatgaa ctcgaaaaat gcgggaataa aatttggaga      960
gctgacaaac ttgaagaatt aattattaat cgtgtgaata attatagttt cgcttccaga     1020
aatgtagata agaagatga attagatagc ttaaatgaaa agcttaaaat agaacatgca      1080
aagaaaaaac gattatttga tttatatata aatggctcgt atgaagtttc agaacttgat     1140
tctatgatga atgatattga tgctcaaatt aattattatg atcacaaat agaagctaac     1200 gaagaattga agaaaaacaa aaagatacaa gaaaatttag ctgatttagc aacagttgat     1260
tttgactctt tagagttcag agaaaagcaa ctttatttaa aatcactaat aaacaaaatt     1320
tatattgatg gtgaacaagt tactattgaa tggctctag                            1359
```

<210> SEQ ID NO 6
<211> LENGTH: 603
<212> TYPE: DNA
<213> ORGANISM: Artificial Sequence
<220> FEATURE:
<223> OTHER INFORMATION: Synthetic Polynucleotide

<400> SEQUENCE: 6

```
atggcacgta cccgagccg tagcagcatt ggtagcctgc gtagtccgca tacccataaa    60
gcaattctga ccagcaccat tgaaatcctg aaagaatgtg gttatagcgg tctgagcatt   120
gaaagcgttg cacgtcgtgc cggtgcaagc aaaccgacca tttatcgttg gtggaccaat   180
aaagcagcac tgattgccga agtgtatgaa atgaaagcg aacaggtgcg taaatttccg    240
gatctgggta gctttaaagc cgatctggat tttctgctgc gtaatctgtg aaagtttgg    300
cgtgaaacca tttgtggtga agcatttcgt tgtgttattg cagaagcaca gctggaccct   360
gcaaccctga cccagctgaa agatcagttt atggaacgtc gtcgtgagat gccgaaaaaa   420
ctggttgaaa atgccattag caatggtgaa ctgccgaaag ataccaatcg tgaactgctg   480
ctggatatga ttttggttt tgttggtat cgcctgctga ccgaacagct gaccgttgaa    540
caggatattg aagaattac cttcctgctg attaatggtg tttgtccggg tacacagcgt   600
taa                                                                603
```

<210> SEQ ID NO 7
<211> LENGTH: 930
<212> TYPE: DNA
<213> ORGANISM: Artificial Sequence
<220> FEATURE:
<223> OTHER INFORMATION: Synthetic Polynucleotide

<400> SEQUENCE: 7

```
atgcaatatg acaattggt tcttctctg aatggcggga gtatgaaaag tatggctgaa    60
gcgcaaaatg atcccctgct gccgggatac tcgtttaatg cccatctggt ggcgggttta   120
acgccgattg aggccaacgg ttatctcgat tttttatcg accgaccgct gggaatgaaa    180
ggttatattc tcaatctcac cattcgcggt caggggtgg tgaaaaatca gggacgagaa    240
tttgttgcc gaccgggtga tattttgctg ttcccgccag gagagattca tcactacggt    300
cgtcatccgg aggctcgcga atggtatcac cagtgggtt actttcgtcc gcgcgcctac    360
tggcatgaat ggcttaactg gccgtcaata tttgccaata cggggttctt tcgcccggat    420
gaagcgcacc agccgcattt cagcgacctg tttgggcaaa tcattaacgc cgggcaaggg   480
gaagggcgct attcggagct gctggcgata aatctgcttg agcaattgtt actgcggcgc   540
atggaagcga ttaacgagtc gctccatcca ccgatggata tcgggtacg cgaggcttgt   600
cagtacatca gcgatcacct ggcagacagc aattttgata tcgccagcgt cgcacagcat   660
gtttgcttgt cgccgtcgcg tctgtcacat cttttccgcc agcagttagg gattagcgtc   720
ttaagctggc gcgaggacca acgtatcagc caggcgaagc tgcttttgag caccaccgg    780
atgcctatcg ccaccgtcgg tcgcaatgtt ggttttgacg atcaactcta tttctcgcgg   840
gtatttaaaa aatgcaccgg ggccagcccg agcgagttcc gtgccggttg tgaagaaaaa   900
gtgaatgatg tagccgtcaa gttgtcataa                                   930
```

<210> SEQ ID NO 8
<211> LENGTH: 51
<212> TYPE: DNA
<213> ORGANISM: Artificial Sequence

```
<220> FEATURE:
<223> OTHER INFORMATION: Synthetic Polynucleotide

<400> SEQUENCE: 8
tctgattcgt taccaattga catgatacga aacgtaccgt atcgttaagg t            51

<210> SEQ ID NO 9
<211> LENGTH: 130
<212> TYPE: DNA
<213> ORGANISM: Artificial Sequence
<220> FEATURE:
<223> OTHER INFORMATION: Synthetic Polynucleotide

<400> SEQUENCE: 9
acattgatta tttgcacggc gtcacacttt gctatgccat agcattttta tccataagat    60
tagcggatcc tacctgacgc tttttatcgc aactctctac tgtttctcca taccgttttt   120
ttgggctagc                                                          130

<210> SEQ ID NO 10
<211> LENGTH: 54
<212> TYPE: DNA
<213> ORGANISM: Artificial Sequence
<220> FEATURE:
<223> OTHER INFORMATION: Synthetic Polynucleotide

<400> SEQUENCE: 10
tccctatcag tgatagagat tgacatccct atcagtgata gagatactga gcac          54

<210> SEQ ID NO 11
<211> LENGTH: 717
<212> TYPE: DNA
<213> ORGANISM: Artificial Sequence
<220> FEATURE:
<223> OTHER INFORMATION: Synthetic Polynucleotide

<400> SEQUENCE: 11
atgagtaaag gagaagaact tttcactgga gttgtcccaa ttcttgttga attagatggt    60
gatgttaatg ggcacaaatt ttctgtcagt ggagagggtg aaggtgatgc aacatacgga   120
aaacttaccc ttaaatttat ttgcactact ggaaaactac ctgttccatg gccaacactt   180
gtcactactt tcggttatgg tgttcaatgc tttgcgagat acccagatca tatgaaacag   240
catgactttt tcaagagtgc catgcccgaa ggttatgtac aggaaagaac tatattttc    300 aaagatgacg ggaactacaa gacacgtgct gaagtcaagt ttgaaggtga taccttgtt    360 aatagaatcg agttaaaagg tattgatttt aagaagatg gaaacattct tggacacaaa    420
ttggaataca actataactc acacaatgta tacatcatgg cagacaaaca aaagaatgga   480
atcaaagtta acttcaaaat tagacacaac attgaagatg gaagcgttca actagcagac   540
cattatcaac aaaatactcc aattggcgat ggccctgtcc ttttaccaga caaccattac   600
ctgtccacac aatctgccct ttcgaaagat cccaacgaaa agagagacca catggtcctt   660
cttgagtttg taacagctgc tgggattaca catggcatgg atgatctcta caaataa      717

<210> SEQ ID NO 12
<211> LENGTH: 693
<212> TYPE: DNA
<213> ORGANISM: Artificial Sequence
<220> FEATURE:
<223> OTHER INFORMATION: Synthetic Polynucleotide

<400> SEQUENCE: 12
```

| | |
|---|---|
| atgagcgagc tgattaagga gaacatgcac atgaagctgt acatggaggg caccgtggac | 60 |
| aaccatcact tcaagtgcac atccgagggc gaaggcaagc cctacagggg cacccagacc | 120 |
| atgagaatca aggtggtcga gggcggccct ctccccttcg ccttcgacat cctggctact | 180 |
| agcttcctct acggcagcaa gaccttcatc aaccacaccc agggcatccc cgacttcttc | 240 |
| aagcagtcct ccctgaggg cttcacatgg gagagagtca ccacatacga agacggggc | 300 |
| gtgctgaccg ctacccagga caccagcctc caggacggct gcctcatcta caacgtcaag | 360 |
| atcagagggg tgaacttcac atccaacggc cctgtgatgc agaagaaaac actcggctgg | 420 |
| gaggccttca ccgagacgct gtaccccgct gacggcggcc tggaaggcag aaacgacatg | 480 |
| gccctgaagc tcgtgggcgg gagccatctg atcgcaaaca tcaagaccac atatagatcc | 540 |
| aagaaacccg ctaagaacct caagatgcct ggcgtctact atgtggacta cagactggaa | 600 |
| agaatcaagg aggccaacaa cgagacctac gtcgagcagc acgaggtggc agtggccaga | 660 |
| tactgcgacc tccctagcaa actggggcac taa | 693 |

<210> SEQ ID NO 13
<211> LENGTH: 705
<212> TYPE: DNA
<213> ORGANISM: Artificial Sequence
<220> FEATURE:
<223> OTHER INFORMATION: Synthetic Polynucleotide

<400> SEQUENCE: 13

| | |
|---|---|
| atgtccagat tagataaaag taaagttgcg agctctgaag acgttatcaa agagttcatg | 60 |
| cgtttcaaag ttcgtatgga aggttccgtt aacggtcacg agttcgaaat cgaaggtgaa | 120 |
| ggtgaaggtc gtccgtacga aggtacccag accgctaaac tgaaagttac caaaggtggt | 180 |
| ccgctgccgt tcgcttggga catcctgtcc ccgcagttcc agtacggttc caaagcttac | 240 |
| gttaaacacc cggctgacat cccggactac ctgaaactgt ccttcccgga aggtttcaaa | 300 |
| tgggaacgtg ttatgaactt cgaagacggt ggtgttgtta ccgttaccca ggactcctcc | 360 |
| ctgcaagacg gtgagttcat ctacaaagtt aaactgcgtg gtaccaactt cccgtccgac | 420 |
| ggtccggtta tgcagaaaaa aaccatgggt tgggaagctt ccaccgaacg tatgtacccg | 480 |
| gaagacggtg ctctgaaagg tgaaatcaaa atgcgtctaa aactgaaaga cggtggtcac | 540 |
| tacgacgctg aagttaaaac cacctacatg gctaaaaaac cggttcagct gccgggtgct | 600 |
| tacaaaaccg acatcaaact ggacatcacc tcccacaacg aagactacac catcgttgaa | 660 |
| cagtacgaac gtgctgaagg tcgtcactcc accggtgctt aataa | 705 |

<210> SEQ ID NO 14
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 14

| | |
|---|---|
| cggccggctt gtcgacgacg gcgcactccg tcgtcaggat catccgggc | 49 |

<210> SEQ ID NO 15
<211> LENGTH: 58
<212> TYPE: DNA
<213> ORGANISM: Artificial Sequence
<220> FEATURE:
<223> OTHER INFORMATION: Synthetic Polynucleotide

<400> SEQUENCE: 15

```
gtcgtggttt gtctggtcaa ccaccgcgca ctcagtggtg tacggtacaa accccgac      58
```

<210> SEQ ID NO 16
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 16

```
cggccggctt gtcgacgacg gcggtctccg tcgtcaggat catccgggc              49
```

<210> SEQ ID NO 17
<211> LENGTH: 58
<212> TYPE: DNA
<213> ORGANISM: Artificial Sequence
<220> FEATURE:
<223> OTHER INFORMATION: Synthetic Polynucleotide

<400> SEQUENCE: 17

```
gtcgtggttt gtctggtcaa ccaccgcggt ctcagtggtg tacggtacaa accccgac      58
```

<210> SEQ ID NO 18
<211> LENGTH: 53
<212> TYPE: DNA
<213> ORGANISM: Artificial Sequence
<220> FEATURE:
<223> OTHER INFORMATION: Synthetic Polynucleotide

<400> SEQUENCE: 18

```
atgccaacac aattaacatc agaatcaagg taaatgcttt ttgcttttttt tgc          53
```

<210> SEQ ID NO 19
<211> LENGTH: 50
<212> TYPE: DNA
<213> ORGANISM: Artificial Sequence
<220> FEATURE:
<223> OTHER INFORMATION: Synthetic Polynucleotide

<400> SEQUENCE: 19

```
gcgagttttt atttcgttta ttagaattaa ggtaactaaa aaactccttt              50
```

<210> SEQ ID NO 20
<211> LENGTH: 53
<212> TYPE: DNA
<213> ORGANISM: Artificial Sequence
<220> FEATURE:
<223> OTHER INFORMATION: Synthetic Polynucleotide

<400> SEQUENCE: 20

```
atgccaacac aattaacatc tcaatcaagg taaatgcttt ttgcttttttt tgc          53
```

<210> SEQ ID NO 21
<211> LENGTH: 50
<212> TYPE: DNA
<213> ORGANISM: Artificial Sequence
<220> FEATURE:
<223> OTHER INFORMATION: Synthetic Polynucleotide

<400> SEQUENCE: 21

```
gcgagttttt atttcgttta tttcaattaa ggtaactaaa aaactccttt              50
```

<210> SEQ ID NO 22
<211> LENGTH: 49
<212> TYPE: DNA

```
<213> ORGANISM: Artificial Sequence
<220> FEATURE:
<223> OTHER INFORMATION: Synthetic Polynucleotide

<400> SEQUENCE: 22 aactttcgg atcaagctat gaaaaacgca aagagggaac taaacactt        49

<210> SEQ ID NO 23
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 23
ttagttcctc gttttctctc gttaaaagaa gaagaaacga gaaactaaa        49

<210> SEQ ID NO 24
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 24 aactttcgg atcaagctat gaaggacgca aagagggaac taaacactt        49

<210> SEQ ID NO 25
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 25
ttagttcctc gttttctctc gttggaagaa gaagaaacga gaaactaaa        49

<210> SEQ ID NO 26
<211> LENGTH: 144
<212> TYPE: DNA
<213> ORGANISM: Artificial Sequence
<220> FEATURE:
<223> OTHER INFORMATION: Synthetic Polynucleotide

<400> SEQUENCE: 26
cacagctaac accacgtcgt ccctatctgc tgccctaggt ctatgagtgg ttgctggata    60
actttacggg catgcataag gctcgtataa tatattcagg gagaccacaa cggtttccct   120
ctacaaataa ttttgtttaa cttt                                          144

<210> SEQ ID NO 27
<211> LENGTH: 68
<212> TYPE: DNA
<213> ORGANISM: Artificial Sequence
<220> FEATURE:
<223> OTHER INFORMATION: Synthetic Polynucleotide

<400> SEQUENCE: 27
taacaccgtg cgtttgacta ttttacctct ggcggtgata atggttgcat atagtgaaca    60
aggattaa                                                             68

<210> SEQ ID NO 28
<211> LENGTH: 70
<212> TYPE: DNA
<213> ORGANISM: Artificial Sequence
```

```
<220> FEATURE:
<223> OTHER INFORMATION: Synthetic Polynucleotide

<400> SEQUENCE: 28
ccgtgacgga tcctggtgca aaacctttcg cggtatggca tgatagcgcc ataggttaaa    60
agccagacat                                                          70

<210> SEQ ID NO 29
<211> LENGTH: 41
<212> TYPE: DNA
<213> ORGANISM: Artificial Sequence
<220> FEATURE:
<223> OTHER INFORMATION: Synthetic Polynucleotide

<400> SEQUENCE: 29
cagataaaaa aaatccttag ctttcgctaa ggatgatttc t                       41

<210> SEQ ID NO 30
<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 30
agttaaccaa aaaggggga ttttatctcc cctttaattt ttcct                    45

<210> SEQ ID NO 31
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 31
atctcctttc acggcccatt cctcatggat gggccgttta tttccc                  46

<210> SEQ ID NO 32
<211> LENGTH: 36
<212> TYPE: DNA
<213> ORGANISM: Artificial Sequence
<220> FEATURE:
<223> OTHER INFORMATION: Synthetic Polynucleotide

<400> SEQUENCE: 32
cccgcactta acccgcttcg gcgggttttt gtttt                              36

<210> SEQ ID NO 33
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 33
gttatgagtc aggaaaaaag gcgacagagt aatctgtcgc cttttttctt tgcttgcttt   60

<210> SEQ ID NO 34
<211> LENGTH: 54
<212> TYPE: DNA
<213> ORGANISM: Artificial Sequence
<220> FEATURE:
<223> OTHER INFORMATION: Synthetic Polynucleotide

<400> SEQUENCE: 34
```

```
gtcagtttca cctgttttac gtaaaaaccc gcttcggcgg gttttttactt ttgg        54
```

<210> SEQ ID NO 35
<211> LENGTH: 57
<212> TYPE: DNA
<213> ORGANISM: Artificial Sequence
<220> FEATURE:
<223> OTHER INFORMATION: Synthetic Polynucleotide

<400> SEQUENCE: 35

```
ggaaacacag aaaaaagccc gcacctgaca gtgcgggctt tttttttcga ccaaagg      57
```

<210> SEQ ID NO 36
<211> LENGTH: 80
<212> TYPE: DNA
<213> ORGANISM: Artificial Sequence
<220> FEATURE:
<223> OTHER INFORMATION: Synthetic Polynucleotide

<400> SEQUENCE: 36

```
ccaggcatca aataaaacga aaggctcagt cgaaagactg ggcctttcgt tttatctgtt   60
gtttgtcggt gaacgctctc                                               80
```

<210> SEQ ID NO 37
<211> LENGTH: 90
<212> TYPE: DNA
<213> ORGANISM: Artificial Sequence
<220> FEATURE:
<223> OTHER INFORMATION: Synthetic Polynucleotide

<400> SEQUENCE: 37

```
ttcagccaaa aaacttaaga ccgccggtct tgtccactac cttgcagtaa tgcggtggac   60
aggatcggcg gttttctttt ctcttctcaa                                    90
```

<210> SEQ ID NO 38
<211> LENGTH: 53
<212> TYPE: DNA
<213> ORGANISM: Artificial Sequence
<220> FEATURE:
<223> OTHER INFORMATION: Synthetic Polynucleotide

<400> SEQUENCE: 38

```
aacgcatgag aaagcccccg gaagatcacc ttccgggggc tttttttattg cgc          53
```

<210> SEQ ID NO 39
<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 39

```
aagaacgagt aaaaggtcgg tttaaccggc cttttttattt tgtga                  45
```

<210> SEQ ID NO 40
<211> LENGTH: 36
<212> TYPE: DNA
<213> ORGANISM: Artificial Sequence
<220> FEATURE:
<223> OTHER INFORMATION: Synthetic Polynucleotide

<400> SEQUENCE: 40

```
aagaccccg caccgaaagg tccgggggtt tttttt                              36
```

<210> SEQ ID NO 41
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 41
acctgtaaaa aaggcagcca tctggctgcc ttagtctccc ca             42

<210> SEQ ID NO 42
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 42
tccggcaatt aaaaaagcgg ctaaccacgc cgcttttttt acgtctgca      49

<210> SEQ ID NO 43
<211> LENGTH: 55
<212> TYPE: DNA
<213> ORGANISM: Artificial Sequence
<220> FEATURE:
<223> OTHER INFORMATION: Synthetic Polynucleotide

<400> SEQUENCE: 43
taaggttgaa aaataaaaac ggcgctaaaa agcgccgttt ttttgacgg tggta    55

<210> SEQ ID NO 44
<211> LENGTH: 47
<212> TYPE: DNA
<213> ORGANISM: Artificial Sequence
<220> FEATURE:
<223> OTHER INFORMATION: Synthetic Polynucleotide

<400> SEQUENCE: 44
acaattttcg aaaaaacccg cttcggcggg ttttttata gctaaaa         47

<210> SEQ ID NO 45
<211> LENGTH: 29
<212> TYPE: DNA
<213> ORGANISM: Artificial Sequence
<220> FEATURE:
<223> OTHER INFORMATION: Synthetic Polynucleotide

<400> SEQUENCE: 45
agcccctcaa tcgagggget ttttttgc                            29

<210> SEQ ID NO 46
<211> LENGTH: 54
<212> TYPE: DNA
<213> ORGANISM: Artificial Sequence
<220> FEATURE:
<223> OTHER INFORMATION: Synthetic Polynucleotide

<400> SEQUENCE: 46
taccaccgtc aaaaaaaacg gcgcttttta gcgccgtttt tattttcaa cctt    54

<210> SEQ ID NO 47
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 47
acatttaata aaaaagggc ggtcgcaaga tcgcccttttt ttacgtatga ca         52

<210> SEQ ID NO 48
<211> LENGTH: 34
<212> TYPE: DNA
<213> ORGANISM: Artificial Sequence
<220> FEATURE:
<223> OTHER INFORMATION: Synthetic Polynucleotide

<400> SEQUENCE: 48
tgtgaaaaag cccgcgcaag cgggttttt tatg                              34

<210> SEQ ID NO 49
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 49
tcgtccgtga cattctgtgc g                                           21

<210> SEQ ID NO 50
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 50
cttctggcat agacagccgc tg                                          22

<210> SEQ ID NO 51
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 51
gagtgcggta ttcctctggg c                                           21

<210> SEQ ID NO 52
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 52
catagccagc ctgacagtag cc                                          22

<210> SEQ ID NO 53
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 53
cgccattccc tagtgagccc                                             20

<210> SEQ ID NO 54
<211> LENGTH: 20

<212> TYPE: DNA
<213> ORGANISM: Artificial Sequence
<220> FEATURE:
<223> OTHER INFORMATION: Synthetic Polynucleotide

<400> SEQUENCE: 54
catgtcatgt cgcgcgaacg                                              20

<210> SEQ ID NO 55
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 55
ccaatatgga caacttcttc gccc                                         24

<210> SEQ ID NO 56
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 56
atggaagcca tcacaaacgg c                                            21

<210> SEQ ID NO 57
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 57
actcgcgctt cgtcgacac                                               19

<210> SEQ ID NO 58
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 58
tgaactgcag cctcagggac g                                            21

<210> SEQ ID NO 59
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 59
catagccagc ctgacagtag cc                                           22

<210> SEQ ID NO 60
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 60
actgtgtcgc tctcagctgc                                              20

<210> SEQ ID NO 61
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 61
gtgcatggtt ggcgctattg c                                            21

<210> SEQ ID NO 62
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 62
atggcctacc tgcaccccaa g                                            21

<210> SEQ ID NO 63
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 63
ggtagctaga tccgcaccac g                                            21

<210> SEQ ID NO 64
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 64
cttctggcat agacagccgc tg                                           22

<210> SEQ ID NO 65
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 65
tcggtcaggt cggagtccta g                                            21

<210> SEQ ID NO 66
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 66
catgtcatgt cgcgcgaacg                                              20

<210> SEQ ID NO 67
<211> LENGTH: 25
<212> TYPE: DNA
<213> ORGANISM: Artificial Sequence

```
<220> FEATURE:
<223> OTHER INFORMATION: Synthetic Polynucleotide

<400> SEQUENCE: 67
cggaacctac actaaggaga tccgg                                          25

<210> SEQ ID NO 68
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 68
cacctggtct acctgtcgat ctg                                            23

<210> SEQ ID NO 69
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 69
ccaatatgga caacttcttc gccc                                           24

<210> SEQ ID NO 70
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 70
atggaagcca tcacaaacgg c                                              21
```

BIOLOGICAL STATE MACHINES

RELATED APPLICATIONS

This application claims the benefit under 35 U.S.C. § 119(e) of U.S. provisional application No. 62/348,601, filed Jun. 10, 2016, U.S. provisional application No. 62/256,829, filed Nov. 18, 2015, and U.S. provisional application No. 62/235,776, filed Oct. 1, 2015, each of which is herein incorporated by reference in its entirety.

FEDERALLY SPONSORED RESEARCH

This invention was made with Government support under Grant No. MCB-1350625 awarded by the National Science Foundation and under Contract No. N66001-12-C-4016 awarded by the Space and Naval Warfare Systems Center. The Government has certain rights in the invention.

REFERENCE TO A COMPUTER PROGRAM LISTING APPENDIX SUBMITTED AS A TEXT FILE VIA COMPACT DISC

The instant application contains a Computer Program Listing Appendix which has been submitted in ASCII format on a compact disc in compliance with 1.52(e) and is hereby incorporated by reference in its entirety. Said ASCII copy, created on Aug. 13, 2019, is named M0656.70377US03-Computer_Program_Listing_Appendix-ZJG, is 49 kilobytes in size, and is submitted in duplicate.

BACKGROUND

State machines are systems that exist in any of a number of states, in which transitions between states are controlled by inputs (1). The next state of a state machine is determined not only by a particular input, but also by its current state. This state-dependent logic can be used to produce outputs that are dependent on the order of inputs, unlike in combinational logic circuits wherein the outputs are solely dependent on the current combination of inputs.

SUMMARY

State machines underlie the sophisticated functionality behind man-made and natural computing systems that perform order-dependent information processing. Recombinases can be used to implement state machines in living cells that record the identities and orders of gene regulatory events, and execute sophisticated input-output functions. FIG. 1 depicts a state machine that enters a different state for each "permuted substring" of the two inputs "A" and "B", by which we refer to each distinct combination and ordering of those two inputs: {no input, A only, B only, A followed by B (A→B), B followed by A (B→A)}.

Provided herein is recombinase-based framework for building state machines in living cells by using chemically controlled DNA excision and inversion operations to encode state in DNA sequence. This strategy enables convenient read-out of states by sequencing and/or PCR, as well as complex regulation of gene expression. The framework was validated by engineering state machines in *Escherichia coli* that used 3 chemical inputs to control 16 DNA states. These state machines were capable of recording the temporal order of all inputs and performing multi-input, multi-output control of gene expression. Also provided herein are computational tools for the automated design of gene regulation programs using recombinase-based state machines. The scalable framework of the present disclosure should enable new strategies for recording and studying how combinational and temporal events regulate complex cell functions and for programming sophisticated cell behaviors.

Some embodiments provide systems, comprising (a) n serine recombinases, wherein n is greater than 2, and (b) an engineered nucleic acid comprising n−1 pairs of cognate recombination recognition sites (RRSs) for each of the n serine recombinases, wherein n(n−1) pairs of RRSs of (b) are arranged in an overlapping configuration such that the two RRSs of each pair of the n(n−1) pairs of RRSs are separated from each other by at least one RRS of another pair of the n(n−1) pairs of RRSs, and wherein recombination between the two RRSs of each pair of the n(n−1) pairs of RRSs either inverts or excises at least one RRS of another pair of the n(n−1) pairs of RRSs.

In some embodiments, n is greater than or equals 3, 4, 5, 6, 7, 8, 9, 10, 11, 12, 13, 14, 15, 16, 17, 18, 19 or 20.

In some embodiments, the n serine recombinase is selected from Bxb1, Tp901, A118, PhIF and AraC.

In some embodiments, the RRSs are selected from an attB site, an attP site, an attB site modified to include a CA dinucleotide, an attP site modified to include a CA dinucleotide, an attB site modified to include a GT dinucleotide, an attP site modified to include a GT dinucleotide, an attB site modified to include a AG dinucleotide, an attP site modified to include a AG dinucleotide, an attB site modified to include a TC dinucleotide, an attP site modified to include a TC dinucleotide, an attB site modified to include a AA dinucleotide, an attP site modified to include a AA dinucleotide, an attB site modified to include a GG dinucleotide, and an attP site modified to include a GG dinucleotide.

In some embodiments, the system further comprises at least one engineered nucleic acid comprising at least one promoter operably linked to a nucleotide sequence encoding at least one of the n serine recombinases.

In some embodiments, the at least one promoter is inducible.

In some embodiments, the at least one promoter is selected from $P_{PhlF}$, $P_{BAD}$ and $P_{LtetO}$.

In some embodiments, the engineered nucleic acid of (b) further comprises a nucleotide sequence encoding a detectable molecule. In some embodiments, the detectable molecule is a fluorescent molecule (e.g., GFP, RFP, BFP, YFP, etc.).

Some embodiments provide systems, comprising (a) three serine recombinases, and (b) an engineered nucleic acid comprising two pairs of cognate recombinase recognition sites (RRSs) for each of the three serine recombinase, wherein six pairs of RRSs of (b) are arranged in an overlapping configuration such that the two RRSs of each pair of the six pairs of RRSs are separated from each other by at least one RRS of another pair of the six pairs of RRSs, and wherein recombination between the two RRSs of each pair of the six pairs of RRSs either inverts or excises at least one RRS of another pair of the six pairs of RRSs.

Some embodiments provide systems, comprising (a) four serine recombinases, and (b) an engineered nucleic acid comprising three pairs of cognate recombinase recognition sites (RRSs) for each of the four serine recombinase, wherein twelve pairs of RRSs of (b) are arranged in an overlapping configuration such that the two RRSs of each pair of the twelve pairs of RRSs are separated from each other by at least one RRS of another pair of the twelve pairs of RRSs, and wherein recombination between the two RRSs of each pair of the twelve pairs of RRSs either inverts or excises at least one RRS of another pair of the twelve pairs of RRSs.

Also provided herein are cells comprising the system of the present disclosure.

In some embodiments, a cell is a bacterial cell or a mammalian cell. In some embodiments, a cell is a stem cell.

Further provided herein are methods of using the system of the present disclosure or a cell of the present disclosure as a therapeutic device or as a diagnostic device.

Some embodiments provide methods of using the system of the present disclosure to control differentiation of a cell.

Some embodiments provide methods of using the system of the present disclosure to detect chemical signals in a cell.

BRIEF DESCRIPTION OF THE DRAWINGS

FIGS. 9A-9C gives more detail on the recombination reactions shown here.

FIGS. 6A-6E. Implementing 2-input, 5-state GRSMs. We built GRSMs (one for each panel A-E) in E. coli to implement the gene regulation programs depicted on the left, with each node containing stripes of different colors corresponding to which gene products (green=GFP, red=RFP, blue=BFP) are expressed in that state (no stripes implies no expression of any gene). The corresponding GRSM state diagrams are depicted in the middle column, with expressed (ON) fluorescent reporters represented by shaded genes and non-expressed (OFF) fluorescent reporters represented by outlined genes. In the right column, nodes represent populations of cells induced with all permuted substrings of the inputs ATc (orange arrow) and Ara (blue arrow). Cultures were treated with saturating concentrations of each input (250 ng/mL ATc or 1% w/v Ara) at 30° C. for 24 hours in three biological replicates. The nodes are shaded according to the percent of cells with different gene expression profiles (ON/OFF combinations of the fluorescent reporters) as measured by flow cytometry. Node labels show the percent of cells with the expected gene expression profile (averaged over all three biological replicates).

Distributions are placed on a biexponential scale. Each induced and non-induced replicate is labeled with the percent of cells expressing GFP, as determined by a threshold (dashed vertical line) set by a control population with no GFP.

Figures 9A, 9B:
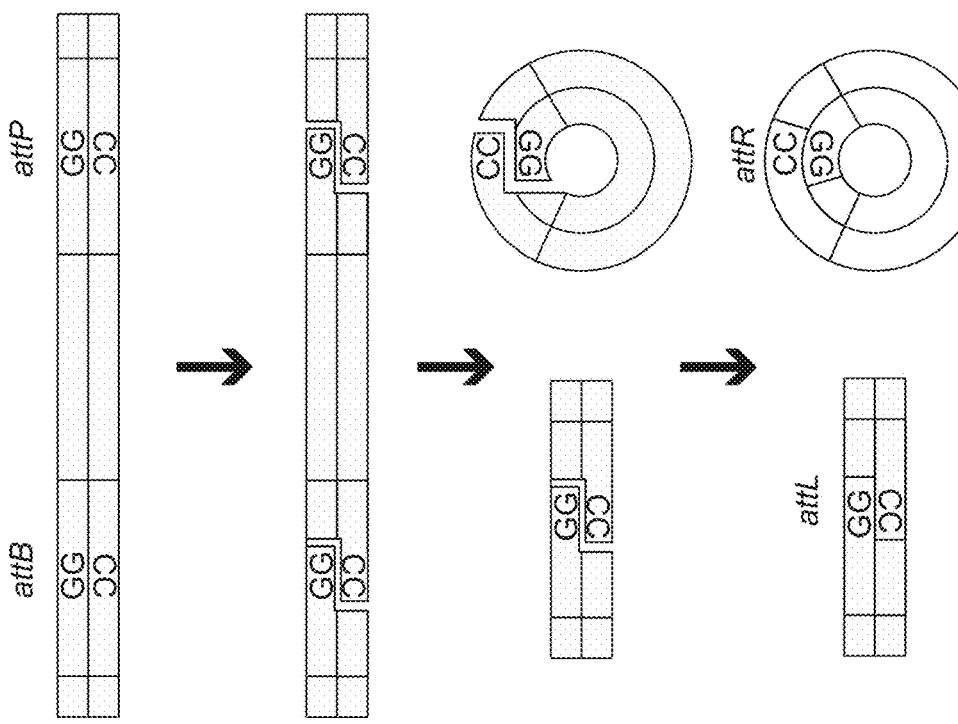

FIGS. 9A-9C. Detailed recombination mechanism. (A) If sites in an attB-attP pair are anti-aligned, then the DNA between them is inverted during recombination. (B) If sites in an attB-attP pair are aligned, then the DNA between them is excised during recombination. The excised fragment circularizes and is assumed to be lost. (C) A recombinase can target multiple attB-attP pairs. If those pairs have mismatched central dinucleotides, then they will only recombine within themselves. Here, two orthogonal inversion operations are shown.

Figure 10:
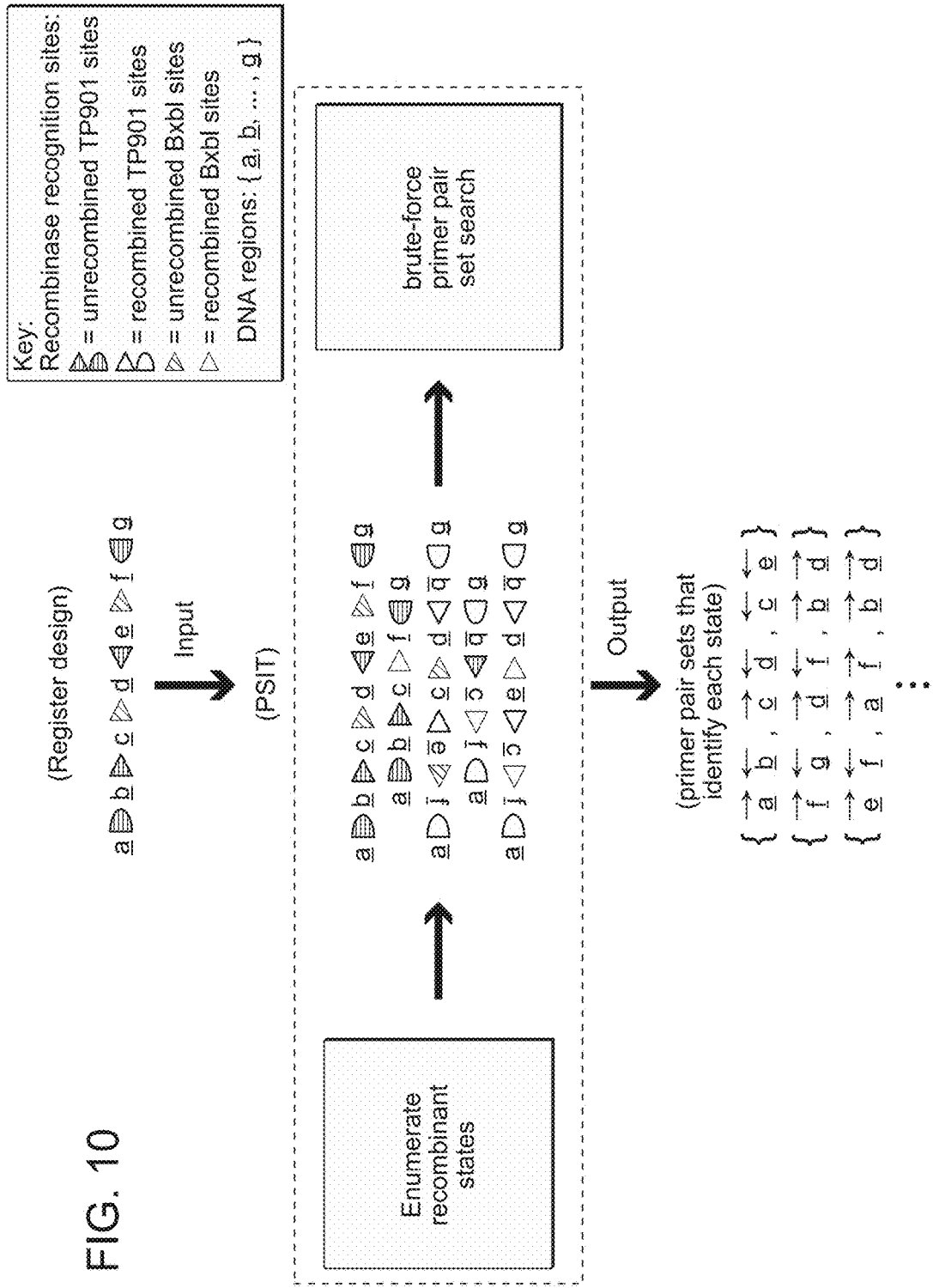

FIG. 10. PCR-based State Interrogation Tool (PSIT). The flowchart gives an overview of the PSIT algorithm and user interface. PSIT accepts a DNA register design as an input and outputs a list of all possible primer pair sets that can be used for state interrogation with qPCR. Primers are specified by the DNA region and direction to which they bind.

Figure 11:
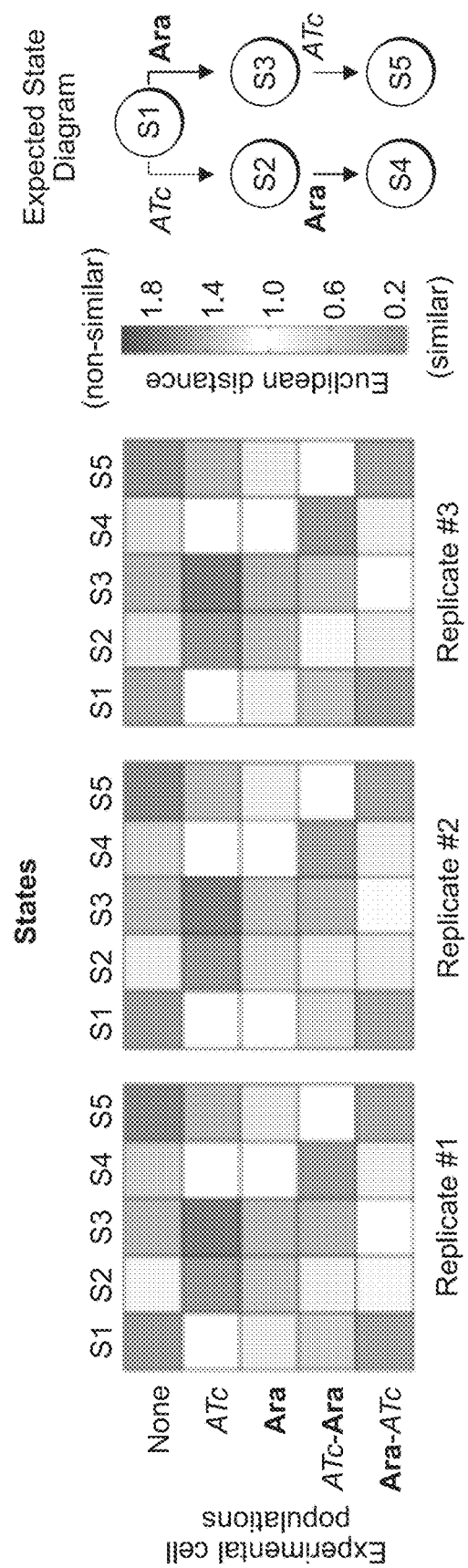

FIG. 11. Quantitative-PCR-based interrogation of the 2-input, 5-state RSM from FIG. 3A. Euclidean distance measured as a metric for similarity. qPCR measurements (with 3 primer pairs designed by our PSIT program) of different experimental E. coli populations containing the RSM were compared to the expected results if all cells adopted one of 5 possible states (S1-S5). Each experimental population was exposed to the inputs indicated along the vertical axis of the heatmap. Cultures were treated with saturating concentrations of each input (250 ng/mL ATc or 1% w/v Ara) at 30° C. for 18 hours. Data is shown for three biological replicates. Every experimental population matched most closely to its predicted state (according to the expected state diagram on the right).

Figure 12:
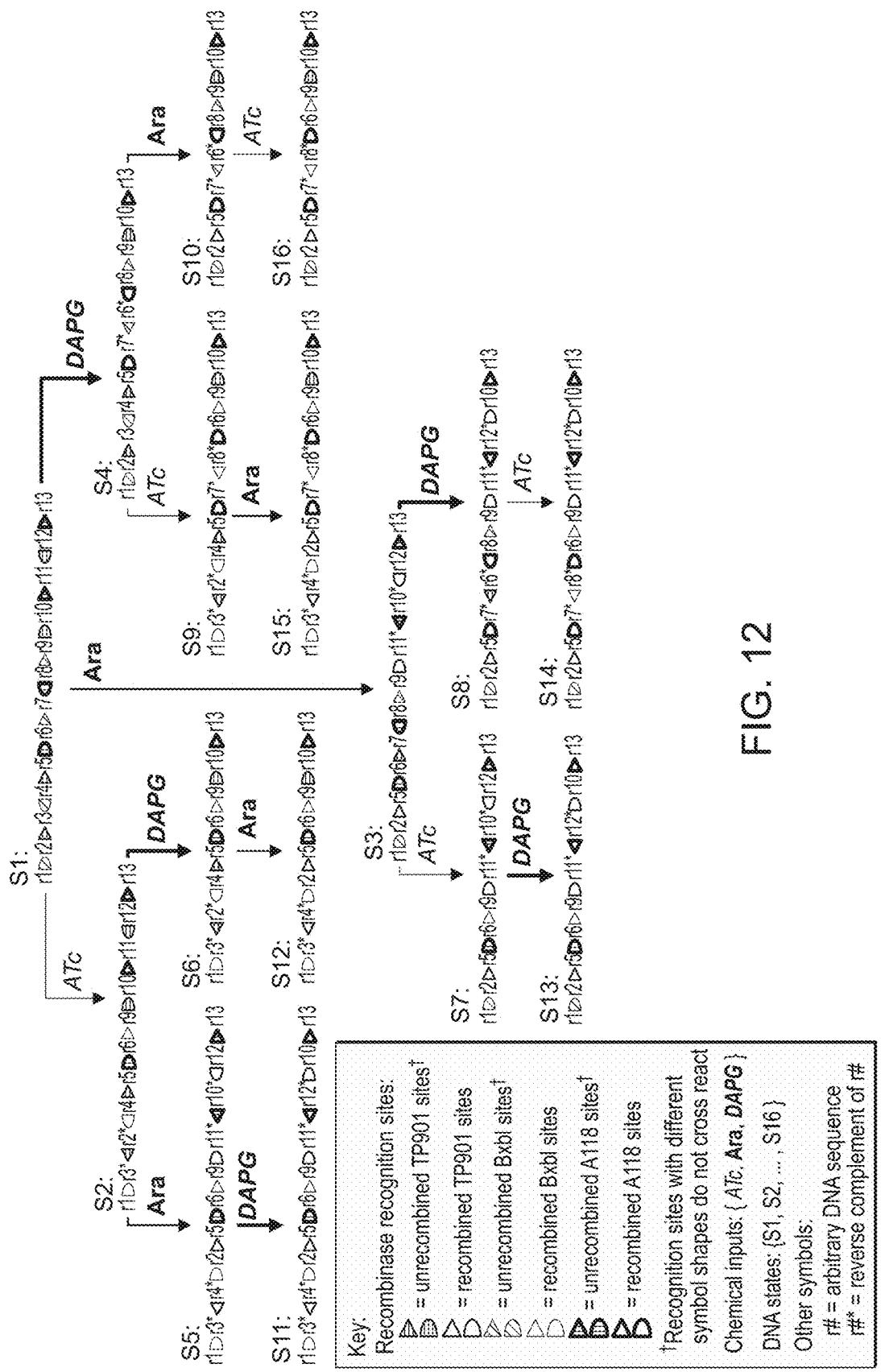

FIG. 12. Detailed state diagram for the register in the 3-input, 16-state RSM from FIG. 4A. We show the different recombinant states of the register in response to different permuted substrings of the inputs ATc (orange), Ara (blue), and DAPG (purple), which activate BxbI, TP901, and A118, respectively.

Figure 13:
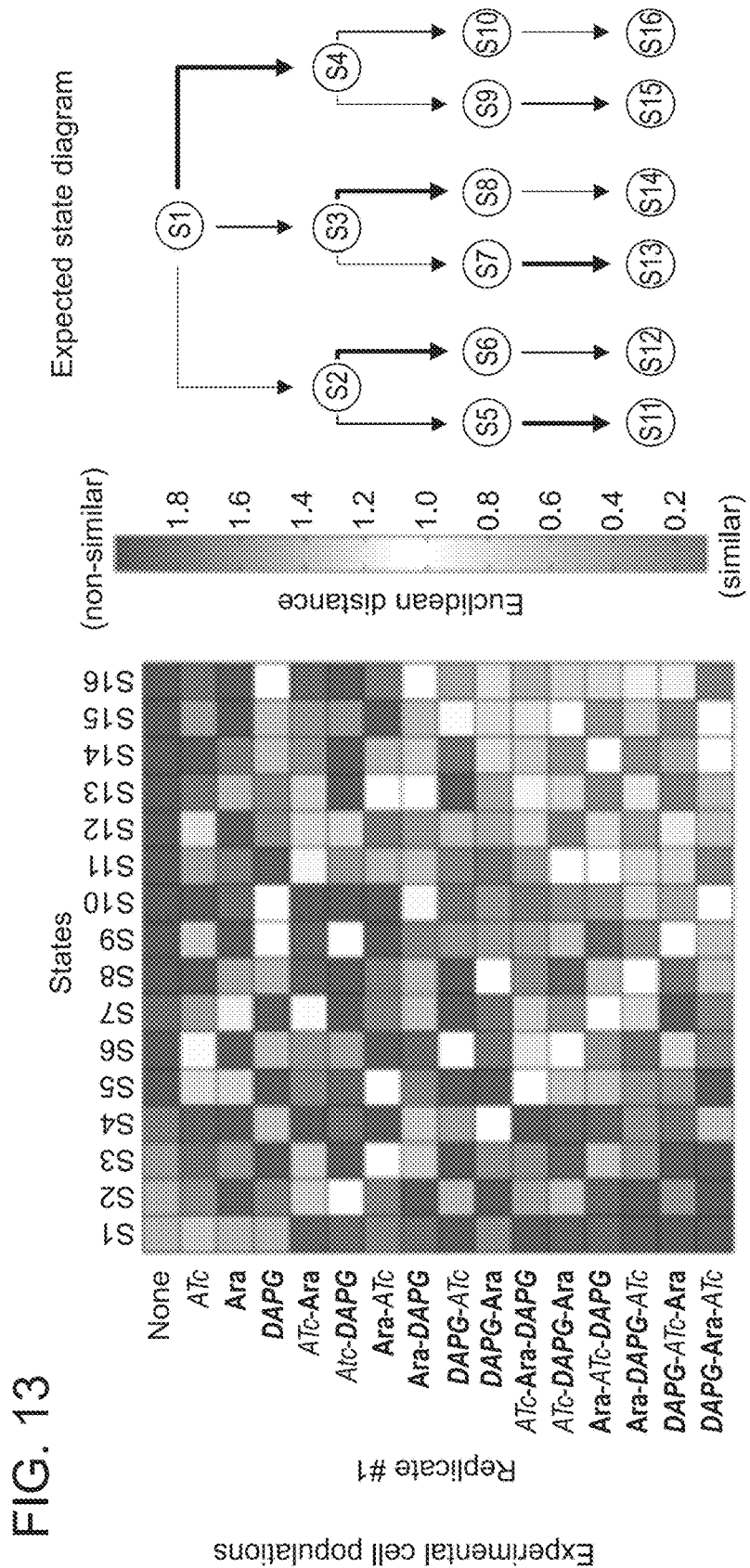
Figure 13:
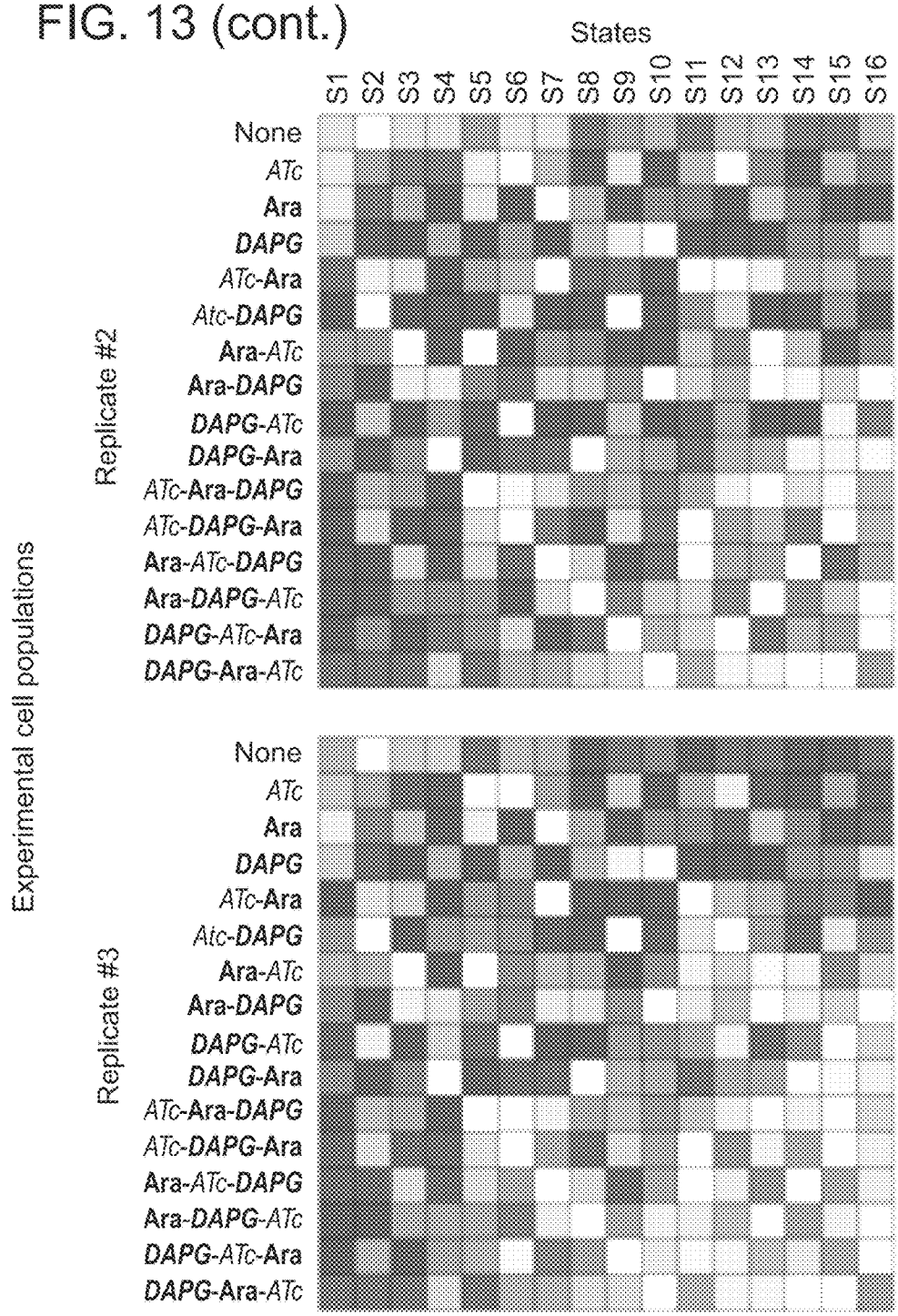

FIG. 13. Quantitative-PCR-based interrogation of the 3-input, 16-state RSM from FIG. 4A. Euclidean distance as a metric for similarity. qPCR measurements (with 6 primer pairs designed by our PSIT program) of different experimental E. coli populations containing the RSM were compared to the expected results if all cells adopted one of 16 possible states (S1-S16). Each population was exposed to the inputs indicated along the vertical axis of the heatmaps. Cultures were treated with saturating concentrations of each input (250 ng/mL ATc, 1% w/v Ara, or 25 µM DAPG) at 30° C. for 24 hours in three biological replicates. Every experimental population matched most closely to its expected state (according to the expected state diagram on the right).

Figure 14A:
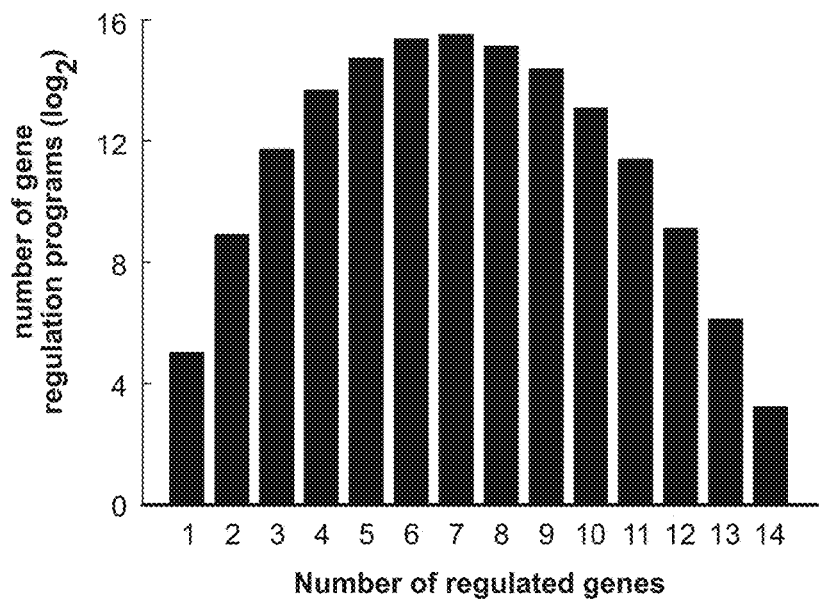
Figure 14B:
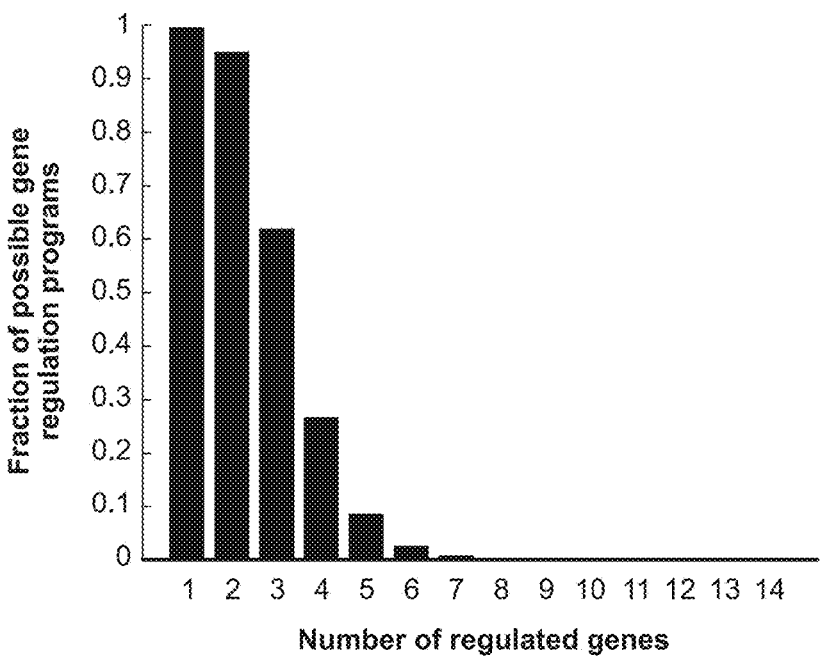

FIGS. 14A-14B. GRSM database coverage. (A) The number of gene regulation programs represented in the database as a function of the number of genes they regulate. (B) The fraction of possible gene regulation programs represented in the database as a function of the number of genes they regulate. To calculate this fraction, we used the formula derived in Example 12 for the total number of gene regulation programs as a function of the number of regulated genes.

Figure 15:
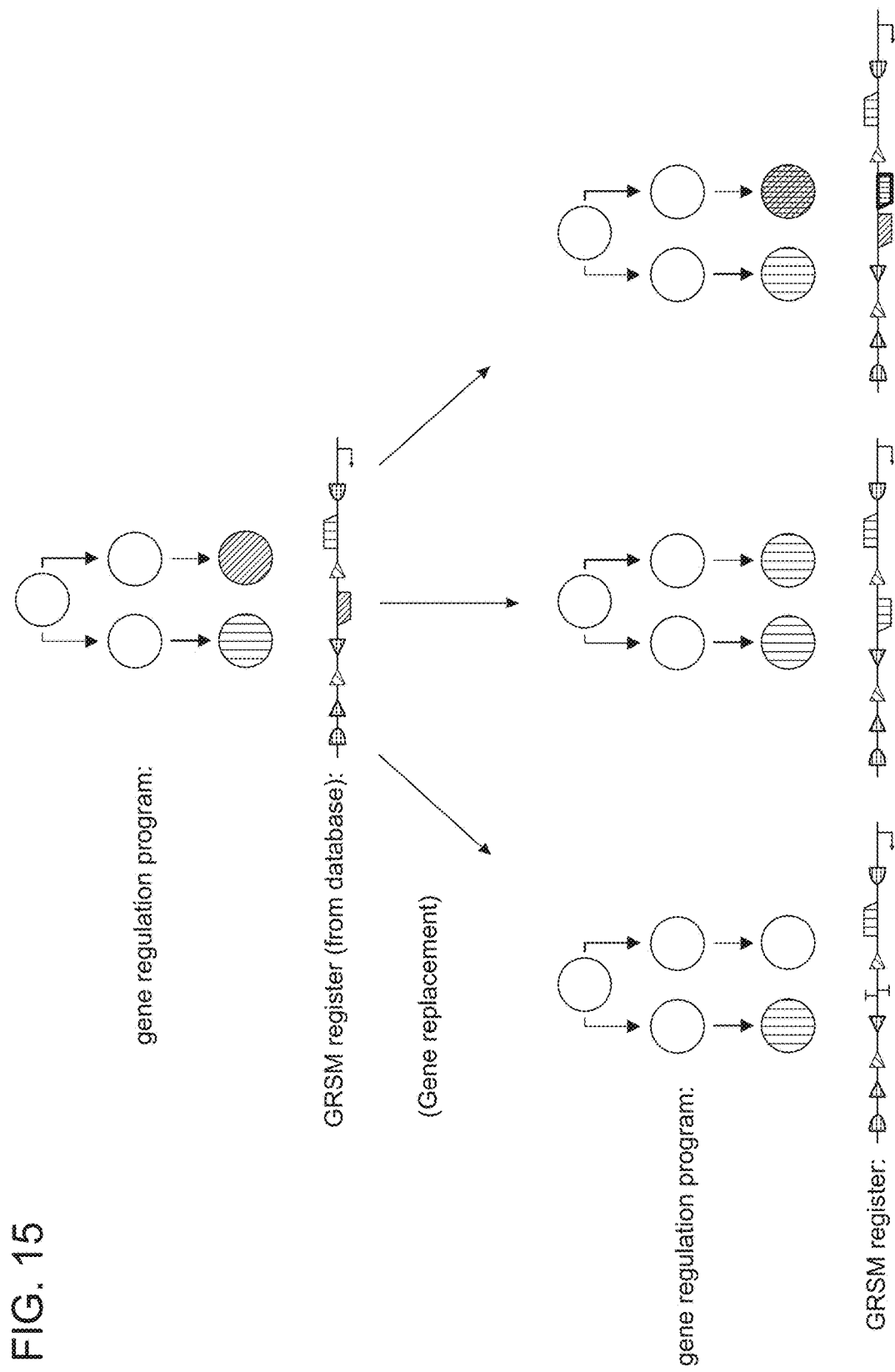
Figure 16A:
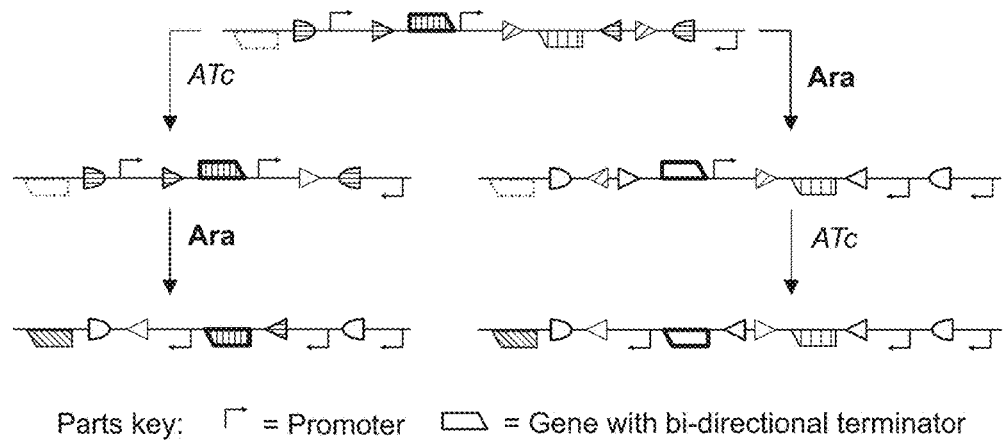
Figure 16B:
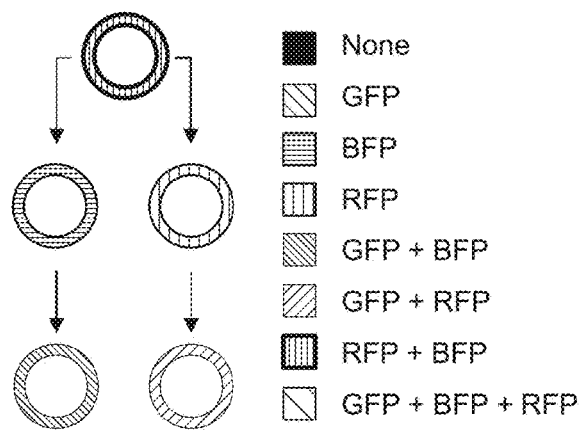
Figure 16E:
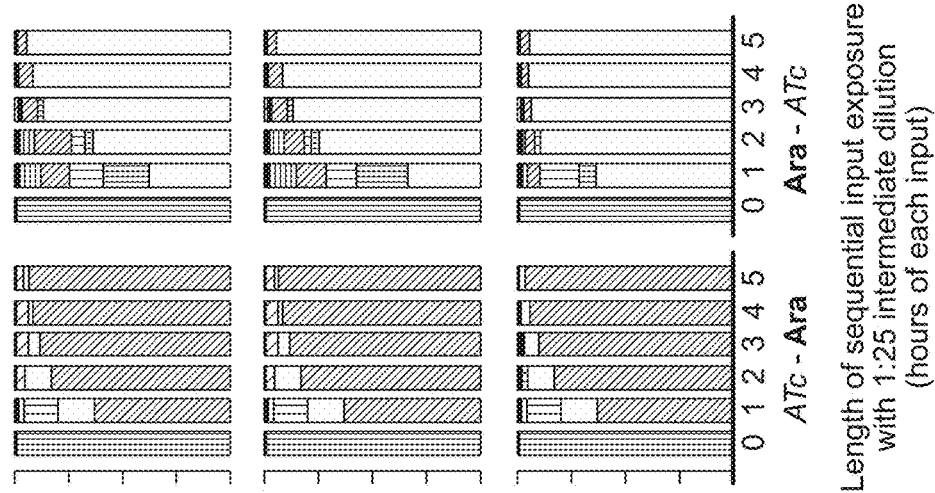
Figure 16D:
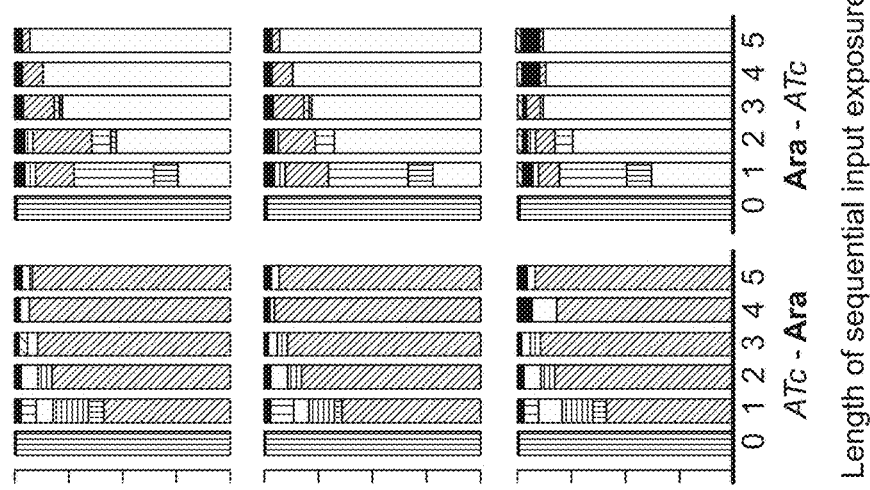
Figure 16C:
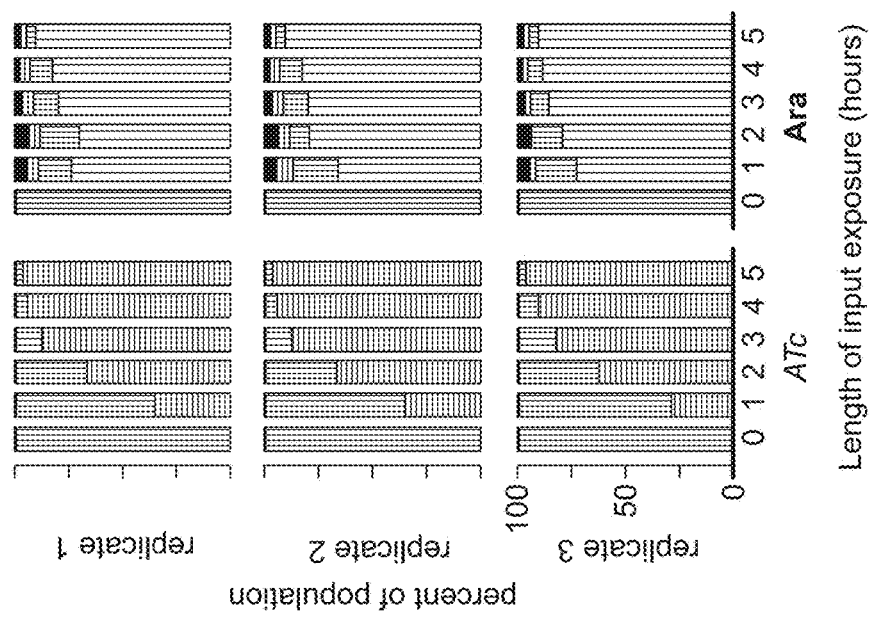

FIG. 15. Examples of how one can replace the gene(s) of a register from the GRSM database to derive registers that implement other gene regulation programs. On the left, one gene is replaced with a bidirectional terminator. In the middle, both distinct genes are replaced with copies of the same gene. On the right, one gene is replaced with a bicistronic operon made up of two distinct genes (in this case, the first gene in the bicistron does not have an implicit terminator on the 3' end). Stripes on the state diagrams for each gene regulation program indicate which genes should be expressed in which state, with different colored stripes representing different genes.

FIGS. 16A-16E. Testing a 2-input, 5-state RSM at different input time durations. (A) The GRSM (from FIG. 6E) that we implemented in E. coli. FP genes in the GRSM (green=GFP, red=RFP, blue=BFP) are shaded or outlined depending on whether or not they are expressed in each state, respectively. (B) There are 8 possible FP expression profiles. Each state of the GRSM adopts a unique FP expression profile. Data from FIG. 6E confirms this. (C-E) The FP expression profile distribution of cells treated with inputs of increasing time duration (with 1-hour steps). Data for three biological replicates is shown. All input exposures were performed with saturating concentrations of the inputs (250 ng/mL ATc or 1% w/v Ara) at 30° C. Columns are shaded according to the percent of cells with different FP expression profiles (corresponding to panel B) as measured by flow cytometry. For the sequential inductions, after the first input exposure period we applied the second input using two different strategies: by directly adding the second input to the culture (panel D), and by diluting the culture 1:25 into new media containing the second input (panel E). Notably for the former strategy, the first input was not diluted out prior to the second input exposure period.

Figure 17A:
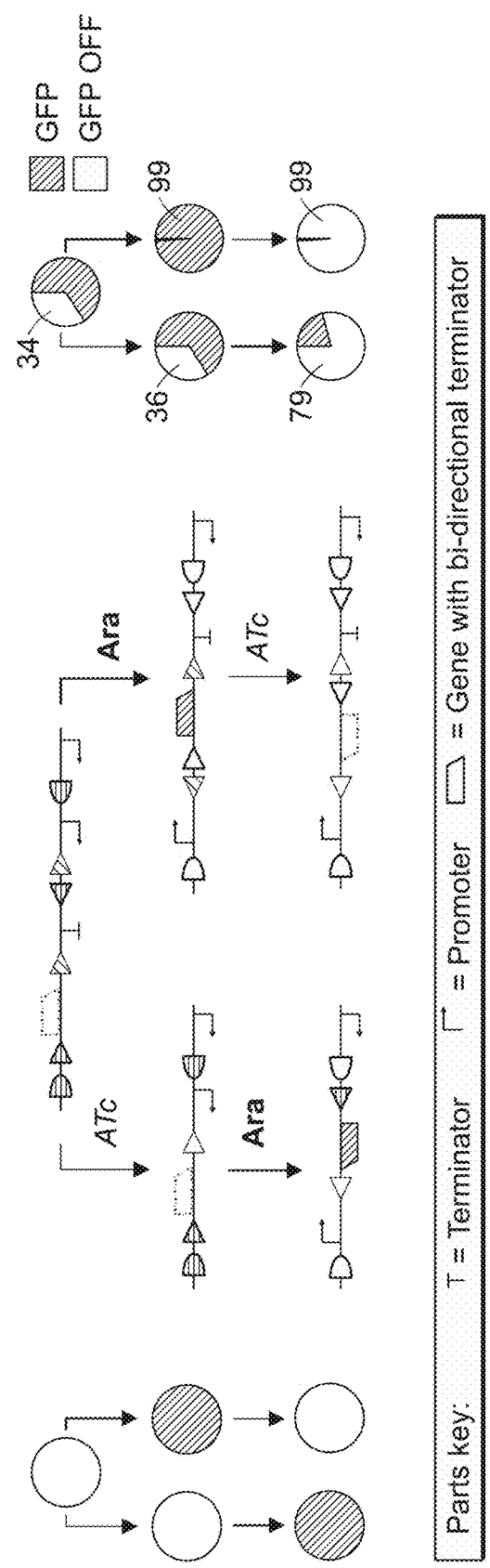
Figure 17B:
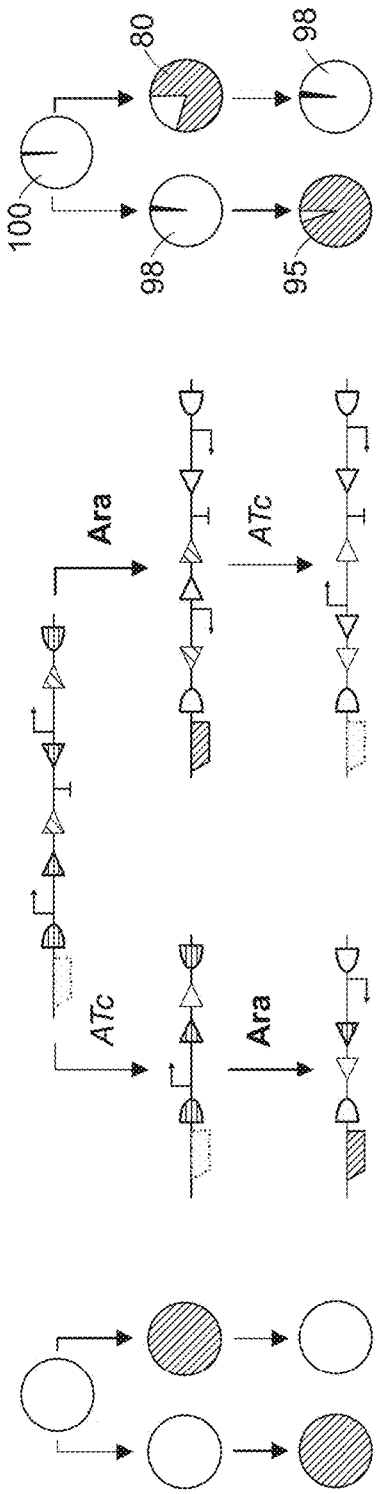
Figure 17C:
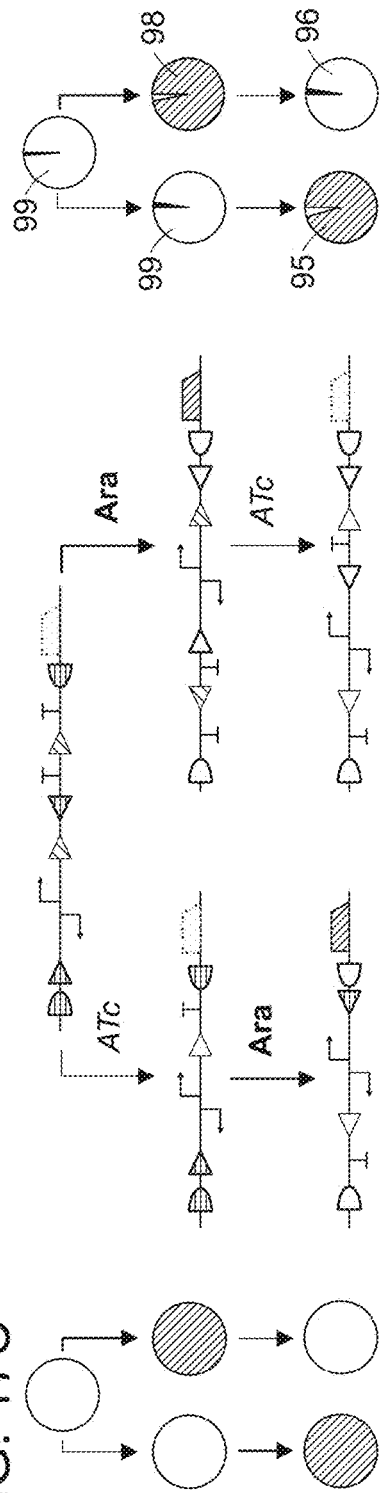

FIGS. 17A-17C. Implementing different GRSMs for the same gene regulation program. We built GRSMs (one for each panel A-C) in E. coli to implement the gene regulation program depicted on the left, with each node containing either green stripes to indicate GFP expression or no stripes to indicate no GFP expression. The corresponding GRSM state diagrams are depicted in the middle column, with expressed (ON) GFP represented by a shaded gfp gene, and non-expressed (OFF) GFP represented by an outlined gfp gene. In the right column, nodes represent populations of cells induced with all permuted substrings of the inputs ATc (orange arrow) and Ara (blue arrow). Cultures were treated with saturating concentrations of each input (250 ng/mL ATc or 1% w/v Ara) at 30° C. for 24 hours in three biological replicates. The nodes are shaded according to the percent of cells with GFP ON versus GFP OFF, as measured by flow cytometry (averaged over all 3 biological replicates). Node labels show the percent of cells with the expected gene expression profile.

Figure 18:
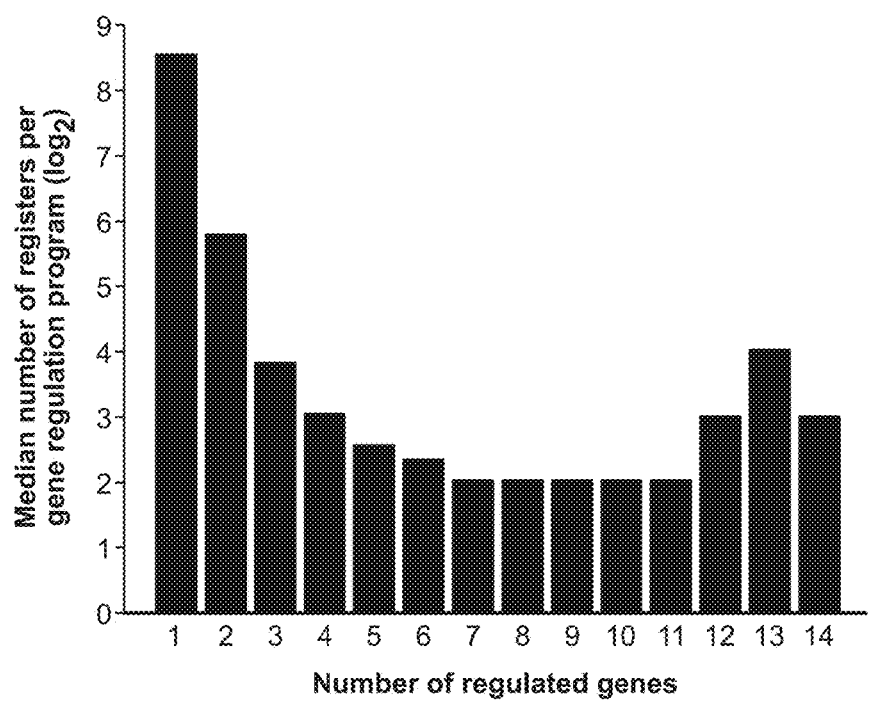

FIG. 18. The design space for gene regulation programs in the GRSM database is highly degenerate. The plot shows the median number of registers per gene regulation program in the GRSM database as a function of how many genes they regulate.

Figure 19:
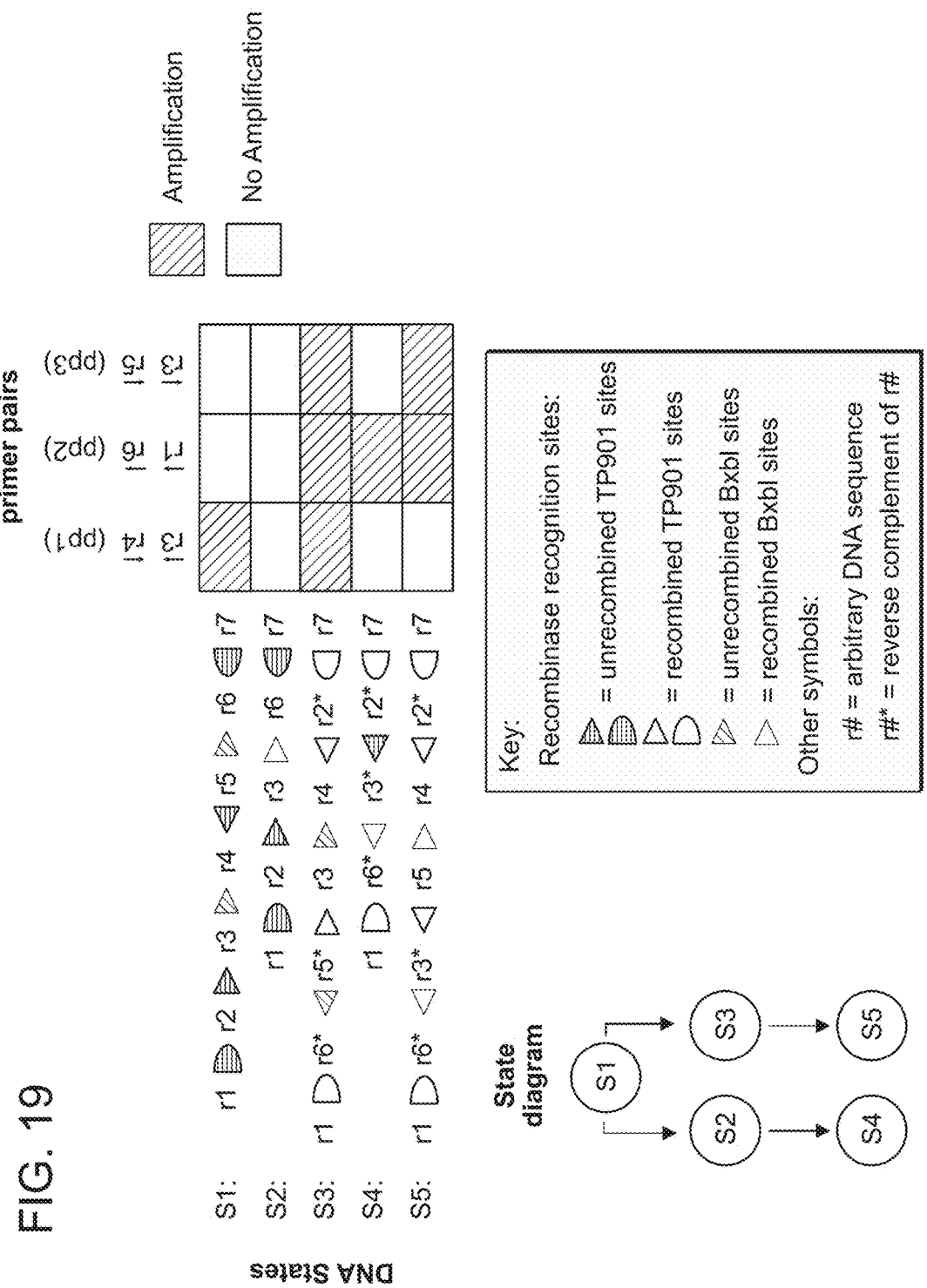

FIG. 19. Quantitative-PCR primer pairs used to interrogate the 2-input, 5-state RSM from FIG. 3A. Each primer binds to the indicated register region in the indicated direction. Actual primer sequences are given in Table 5. The map indicates which primer pairs should amplify in which states, where states are related to each other as shown in the state diagram.

Figure 20:
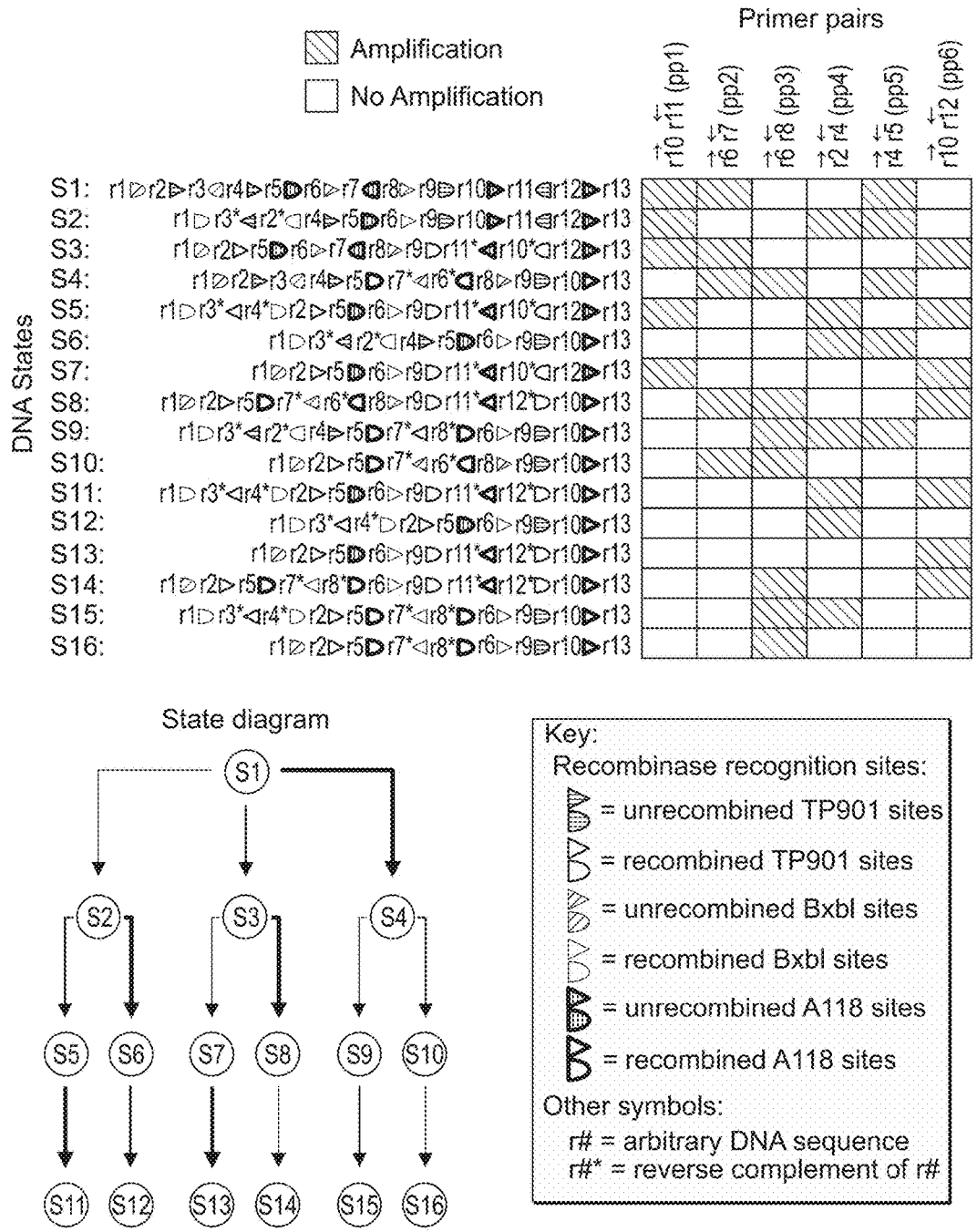

FIG. 20. Quantitative-PCR primer pairs used to interrogate the 3-input, 16-state RSM from FIG. 4A. Each primer binds to the indicated register region in the indicated direction. Actual primer sequences are given in Table 6. The map indicates which primer pairs should amplify in which states, where states are related to each other as shown in the state diagram.

Figure 21:
Figure 21:
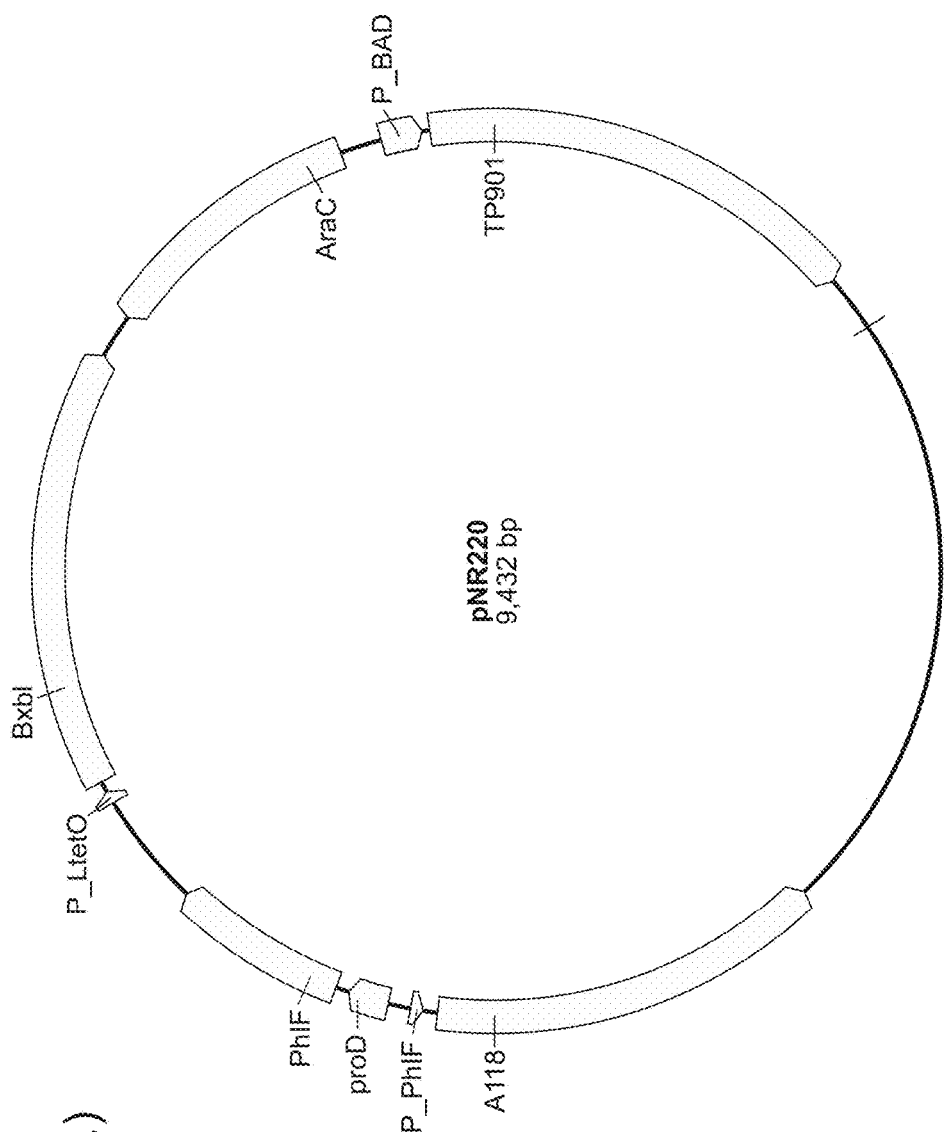
Figure 21:
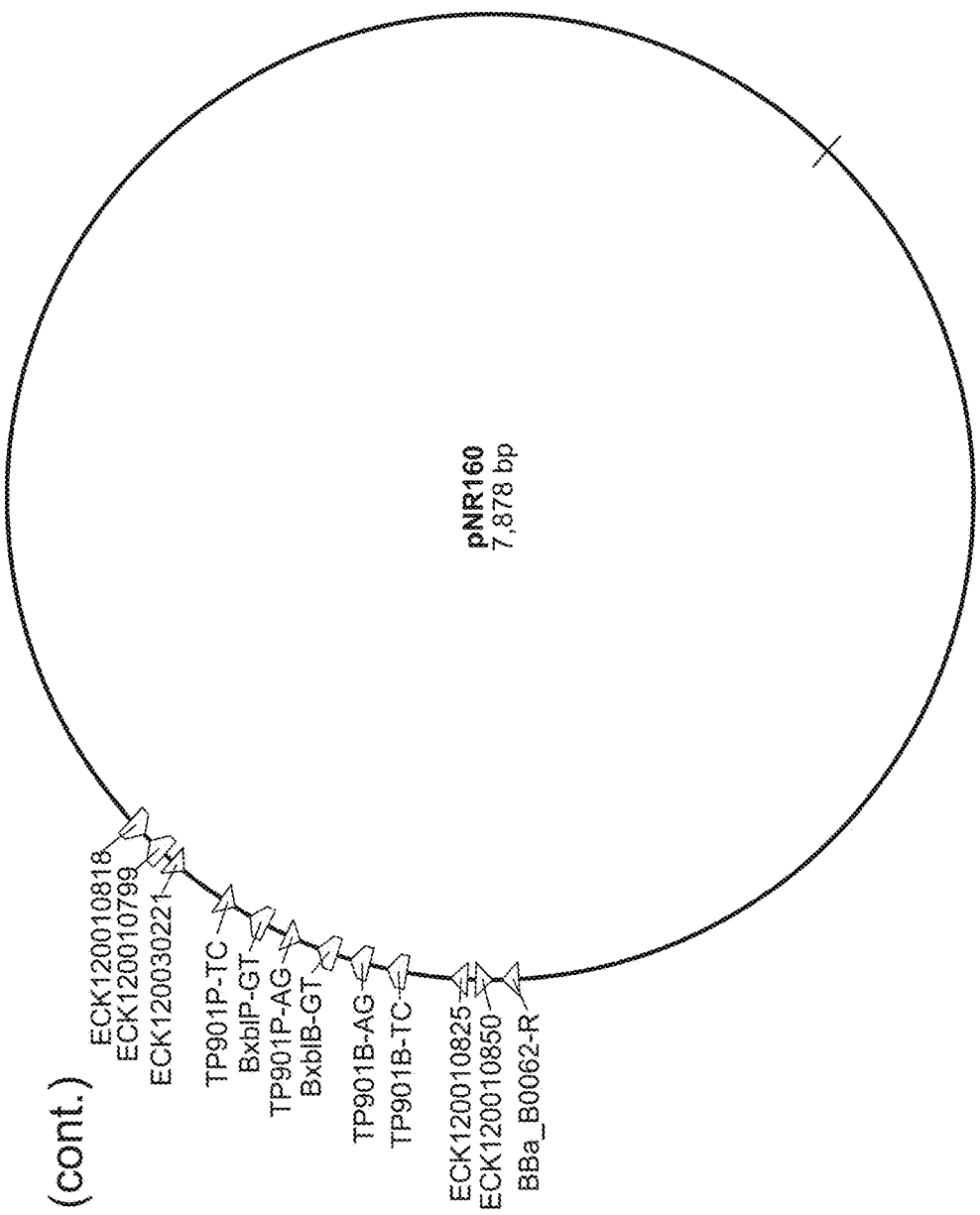
Figure 21:
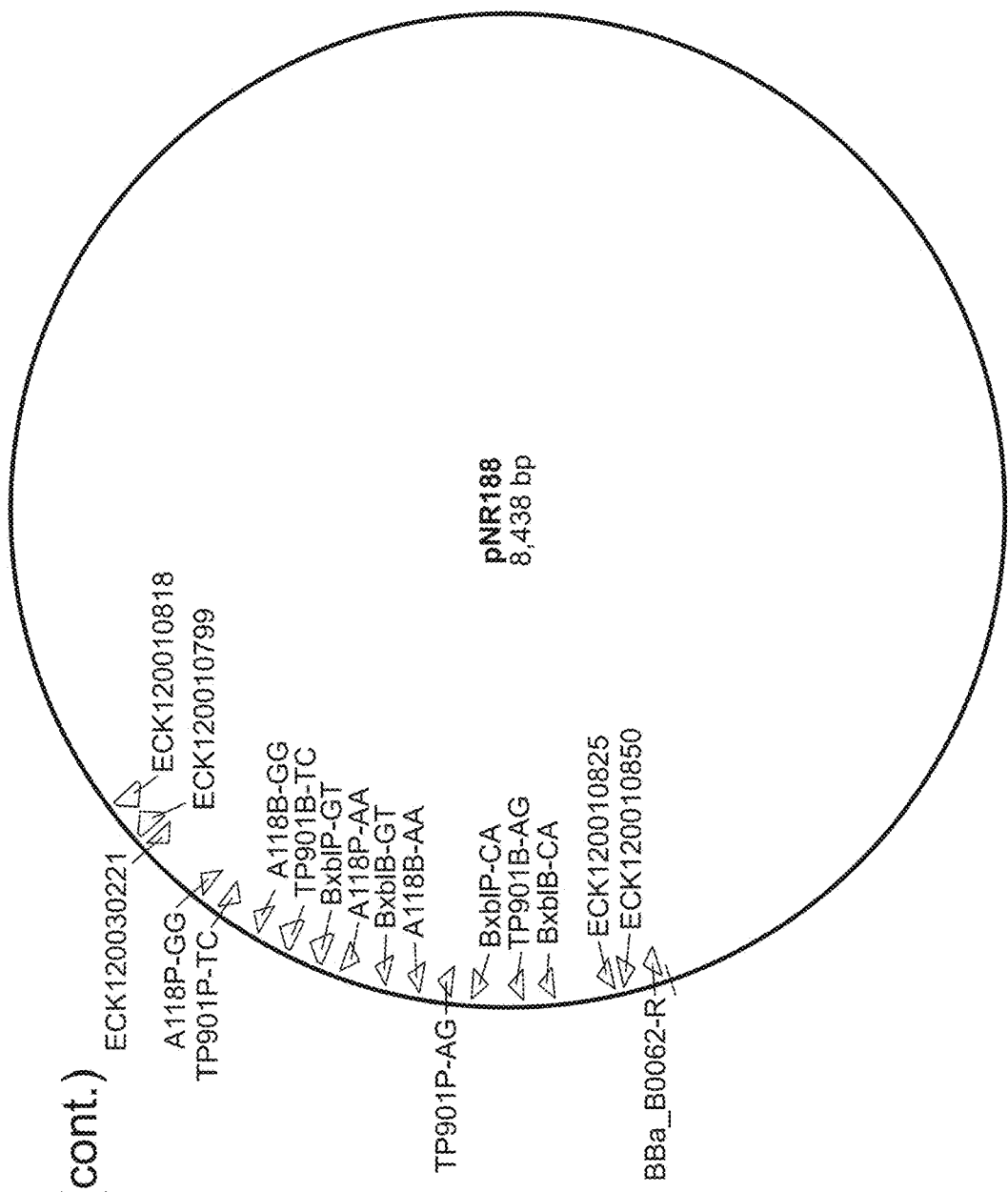
Figure 21:
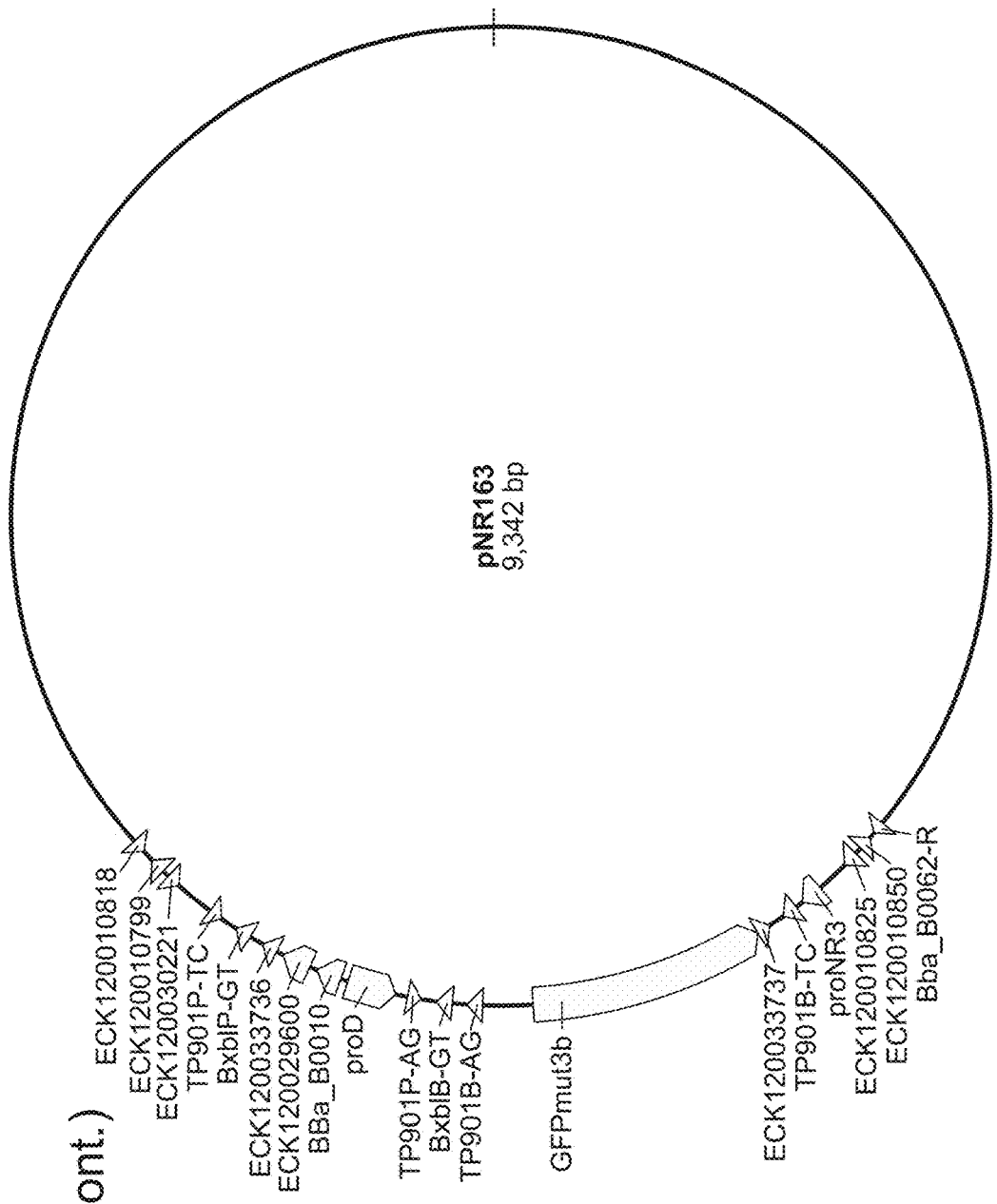
Figure 21:
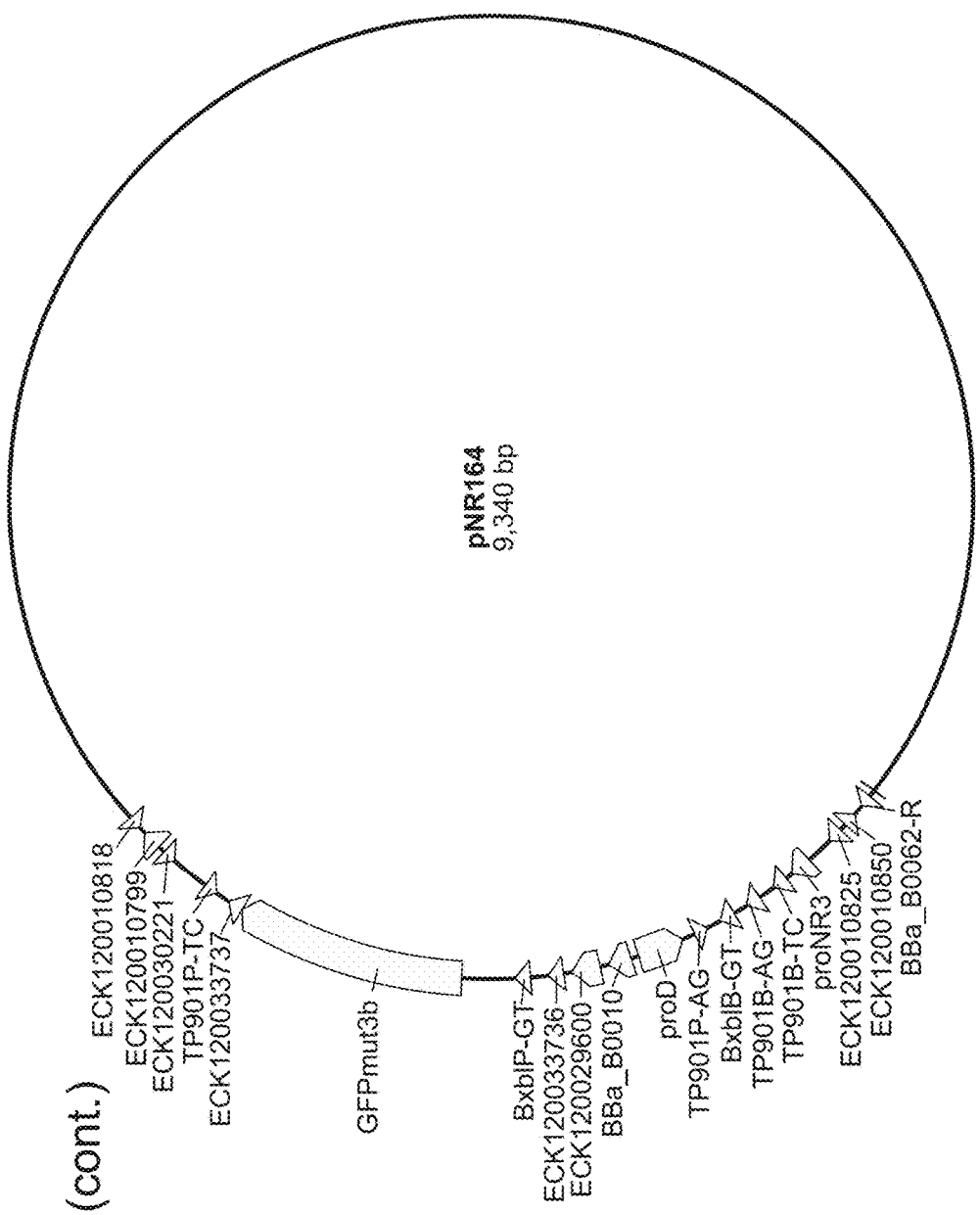
Figure 21:
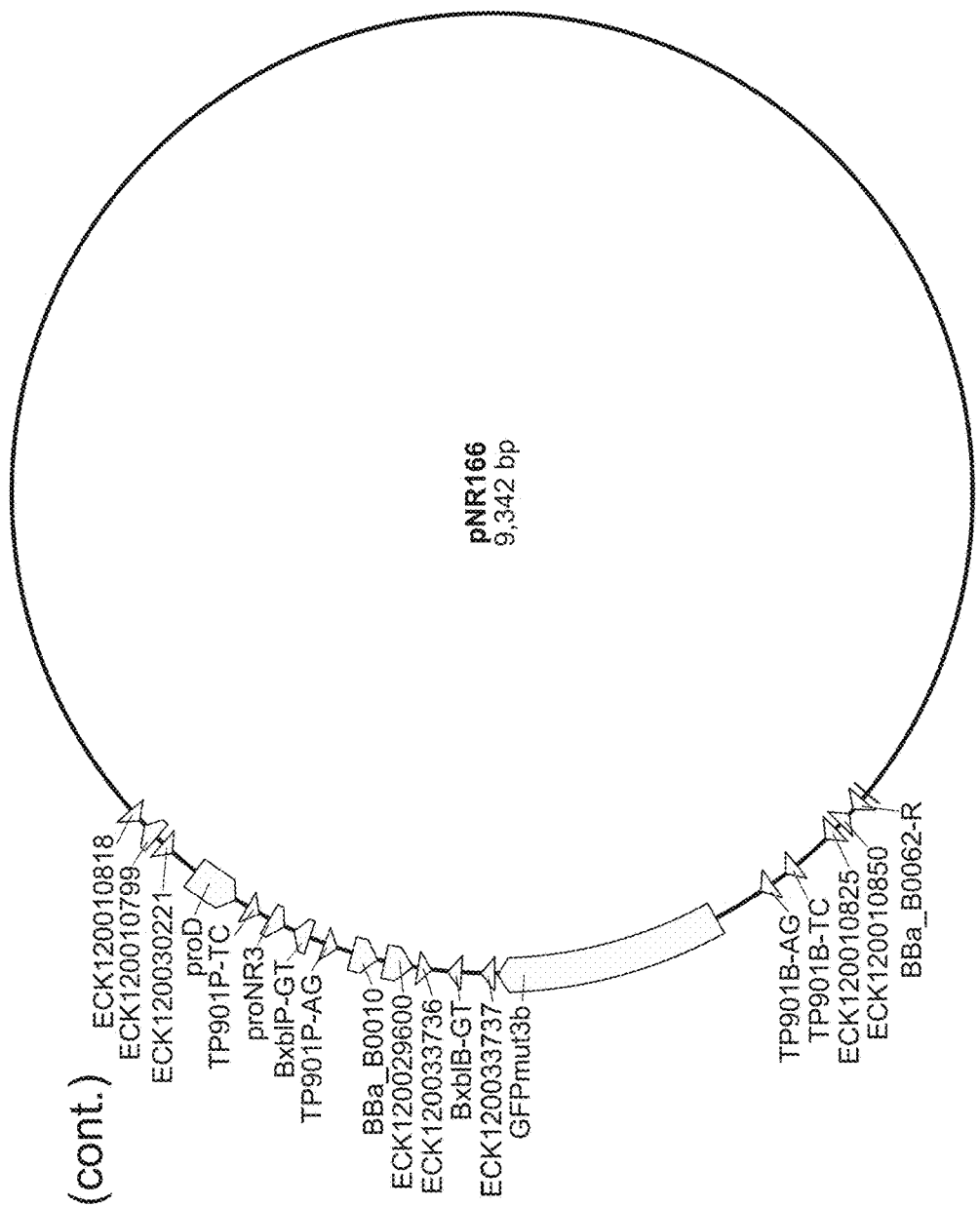
Figure 21:
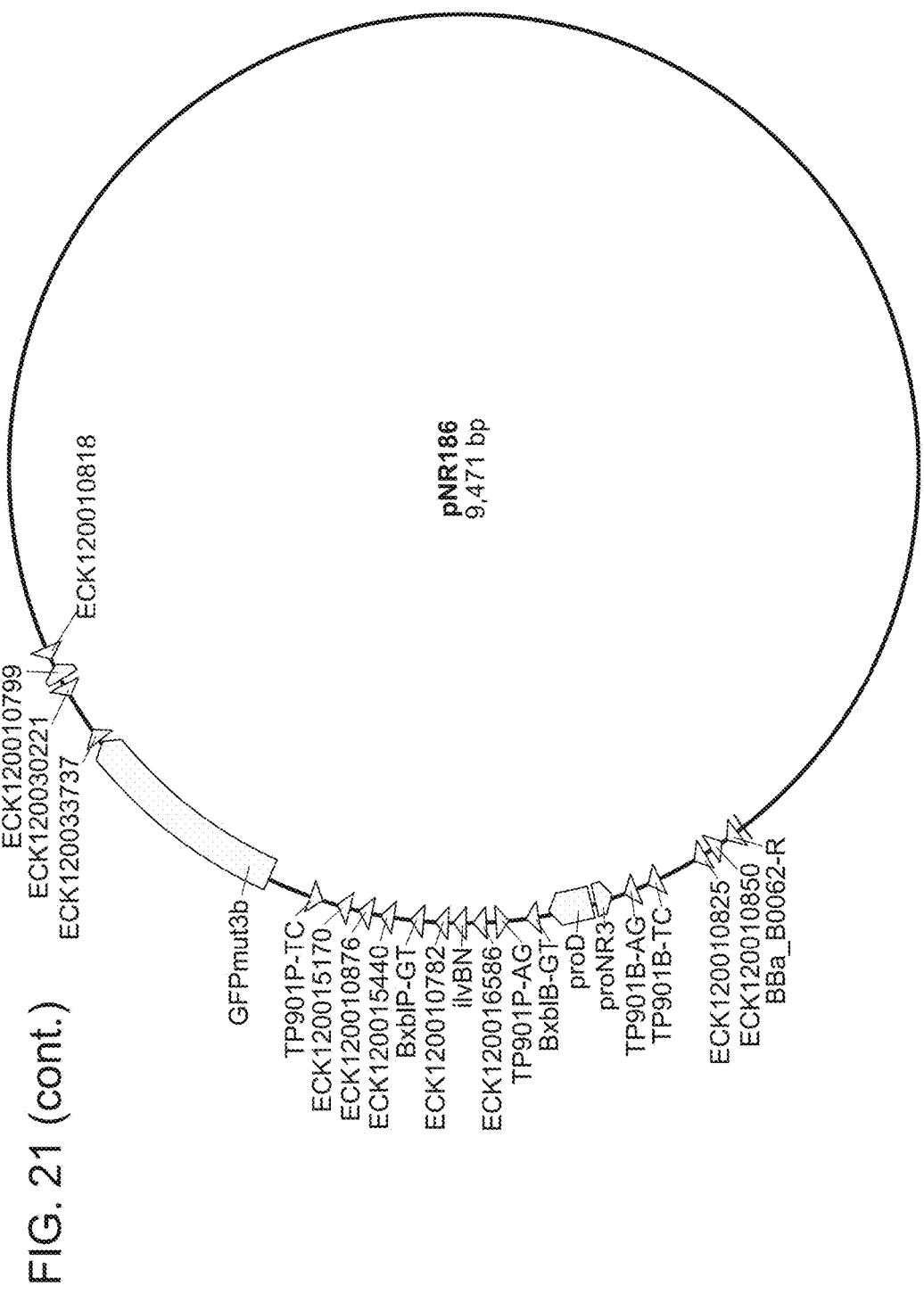
Figure 21:
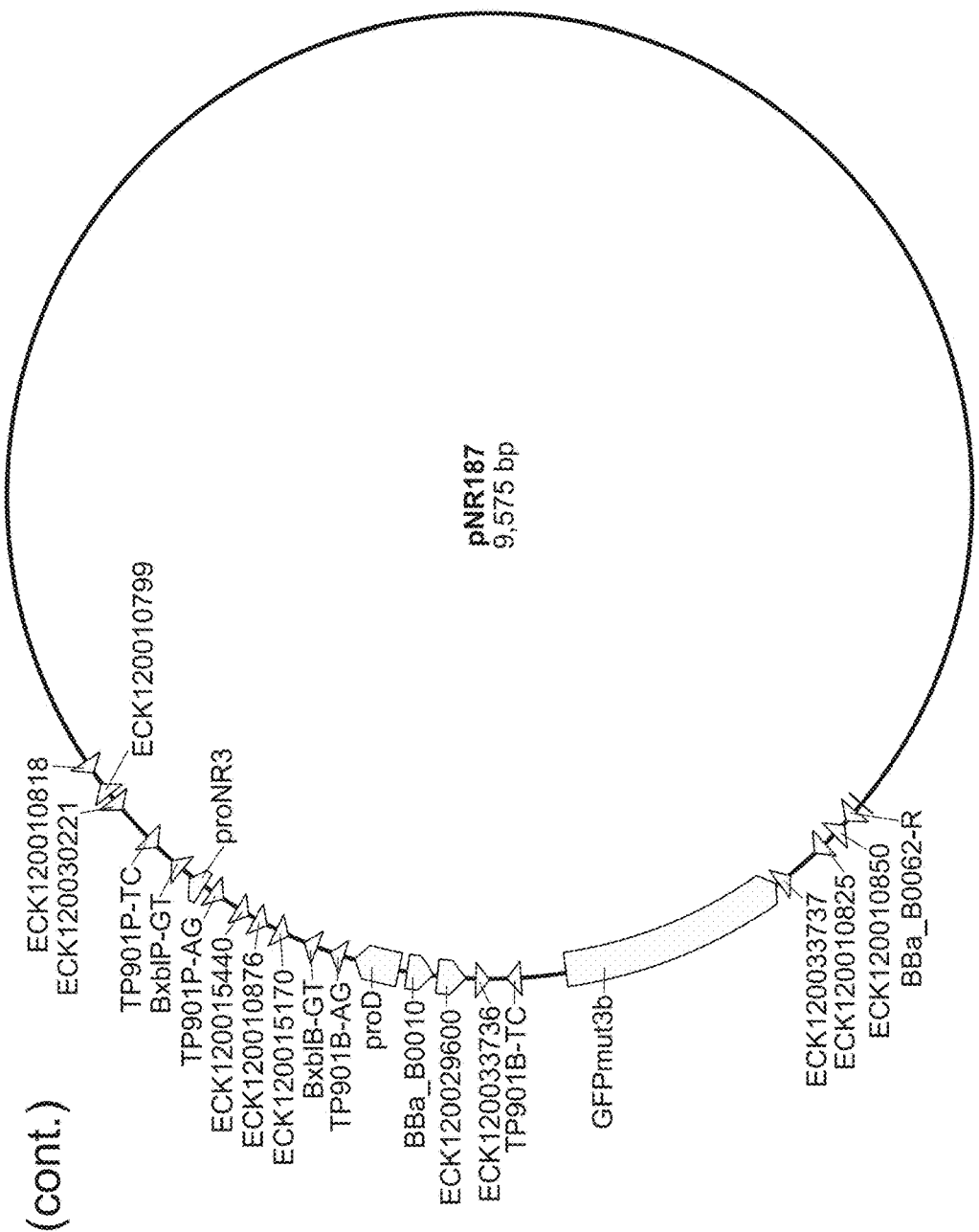
Figure 21:
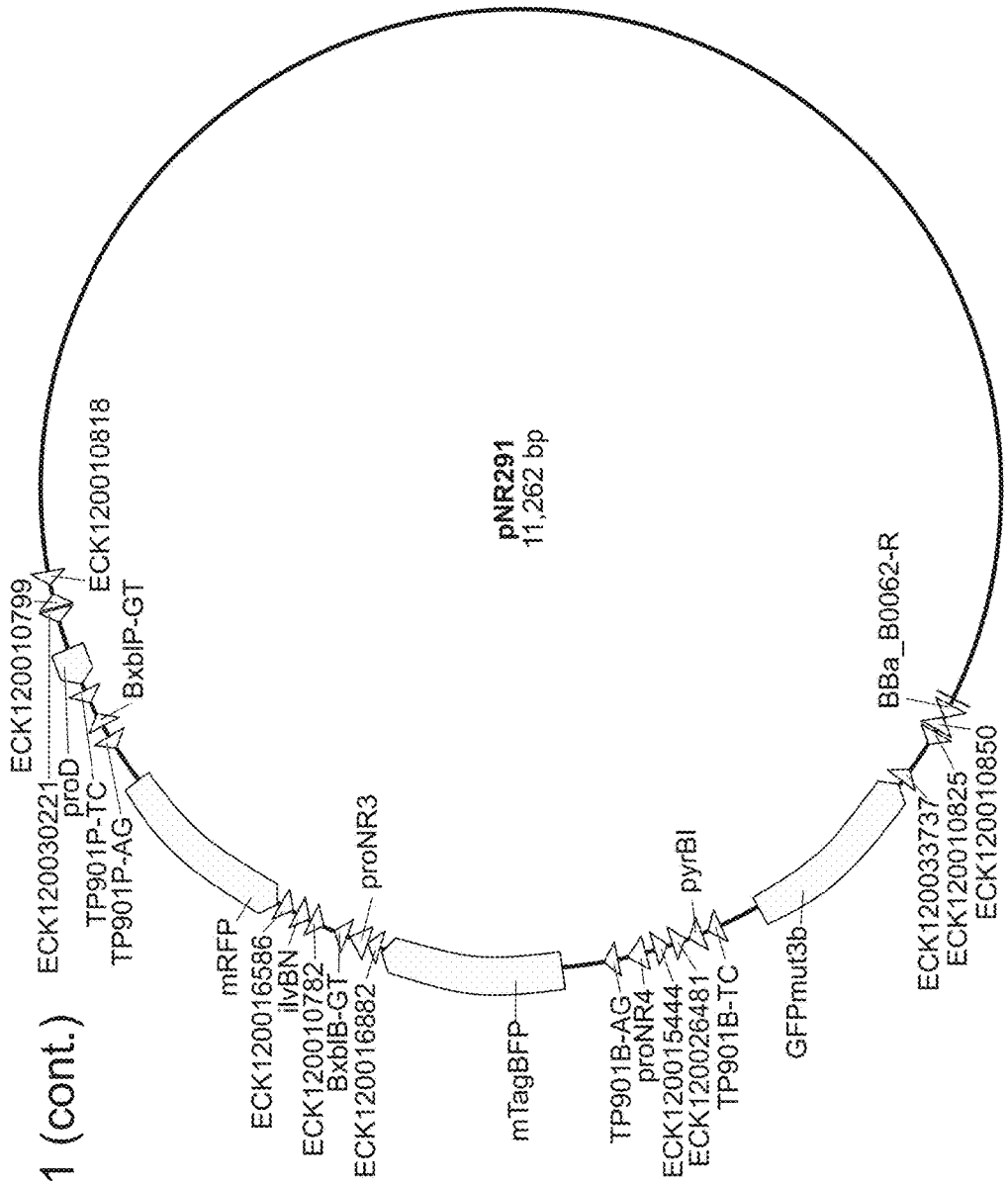
Figure 21:
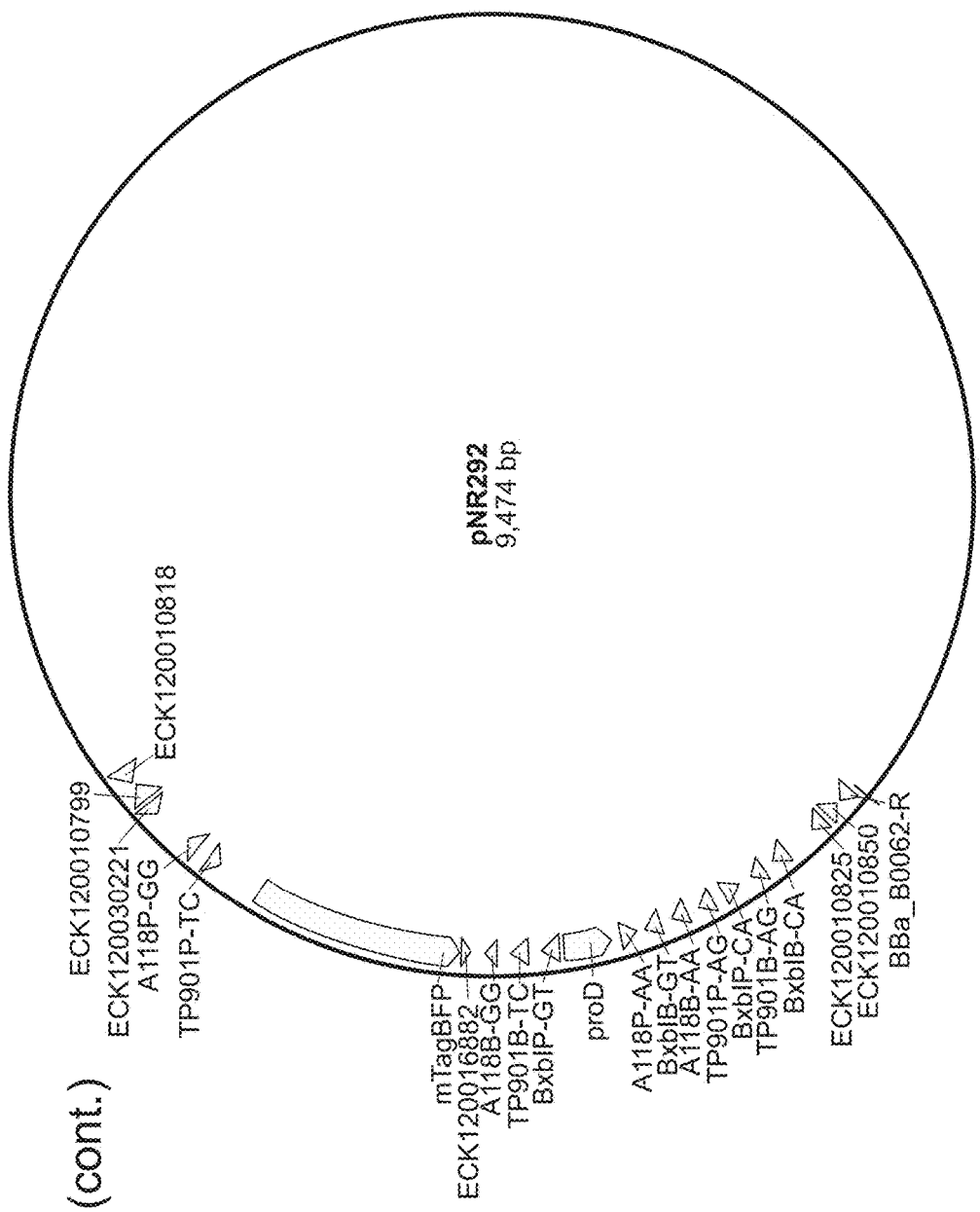
Figure 21:
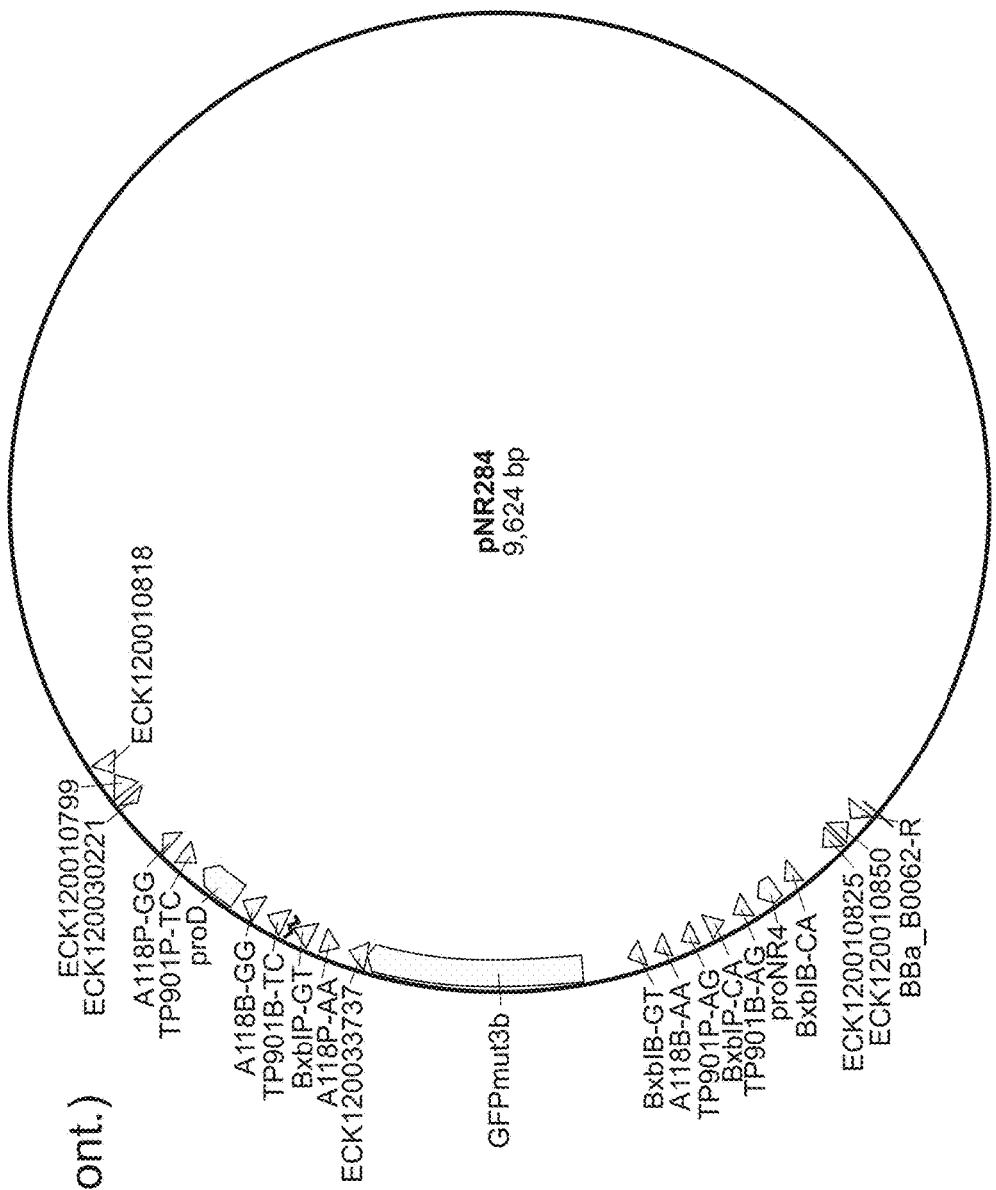
Figure 21:
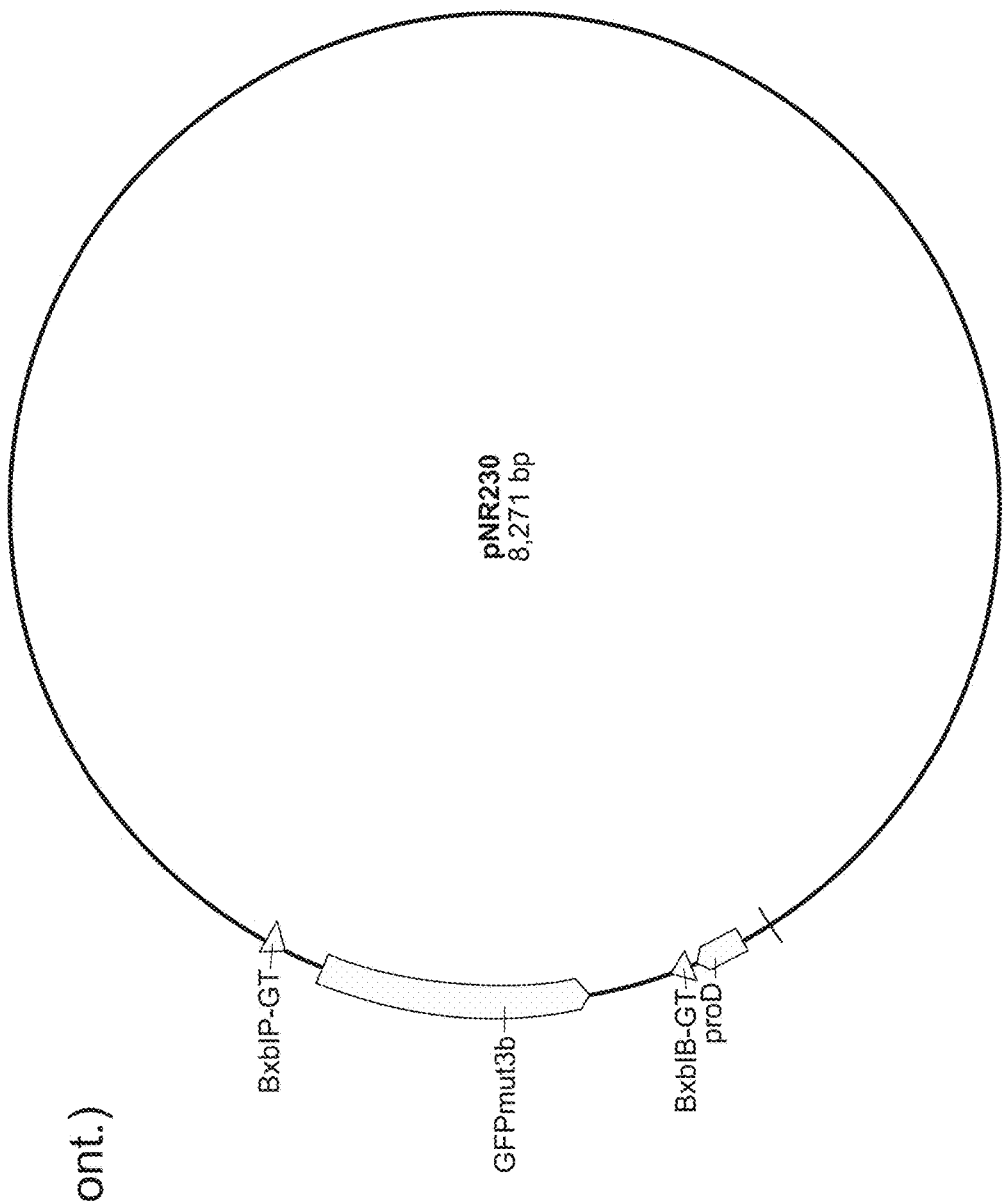
Figure 21:
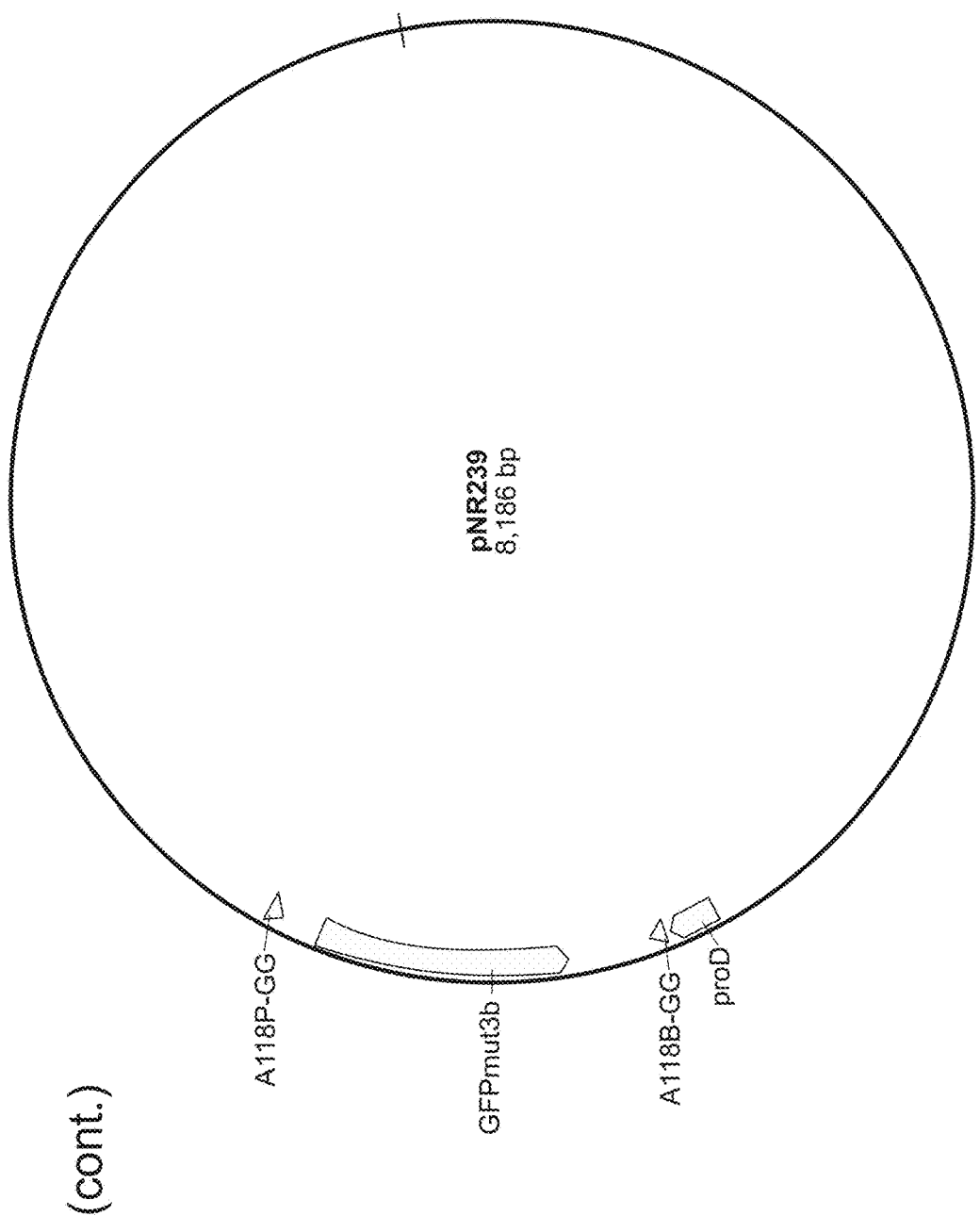
Figure 21:
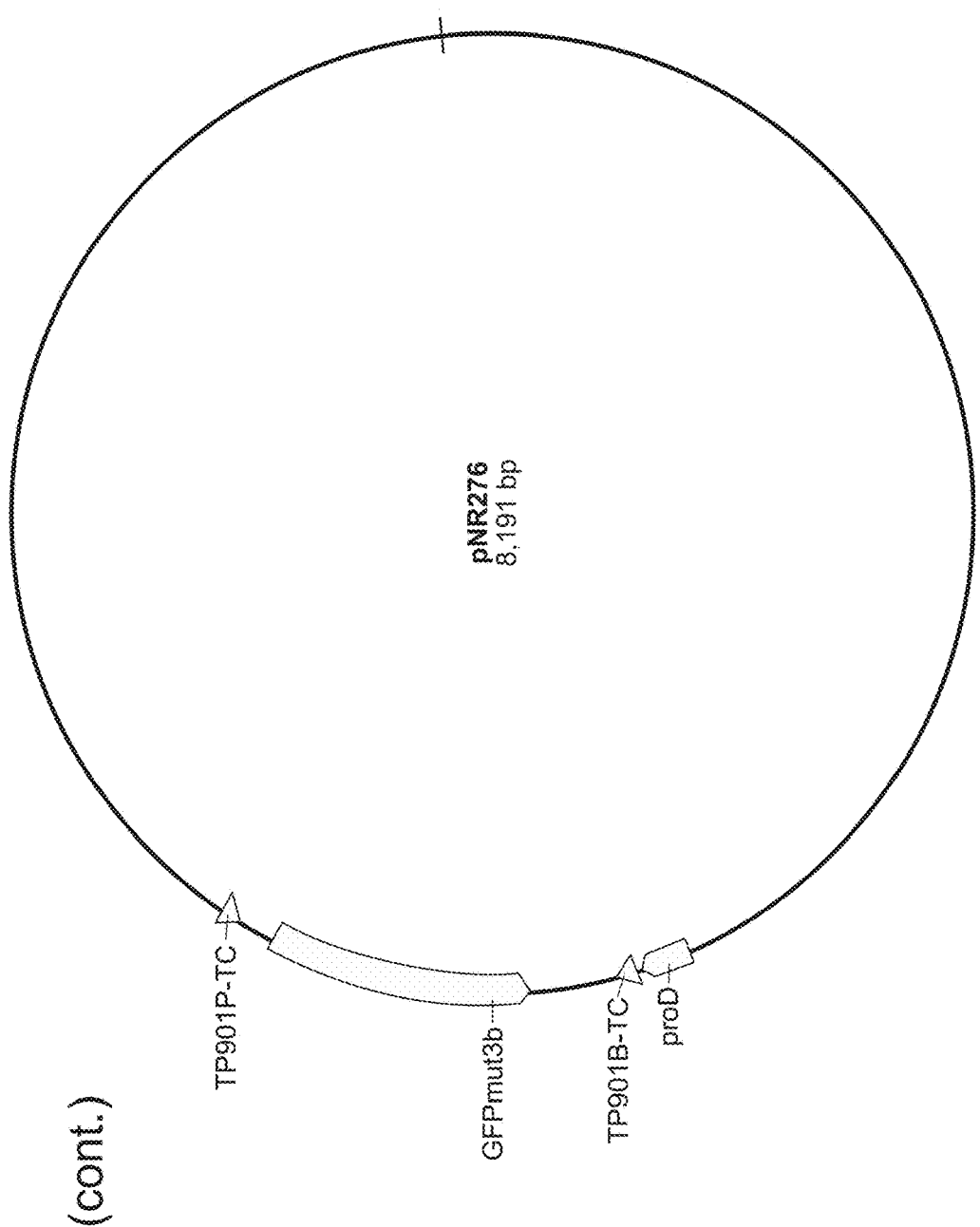
Figure 21:
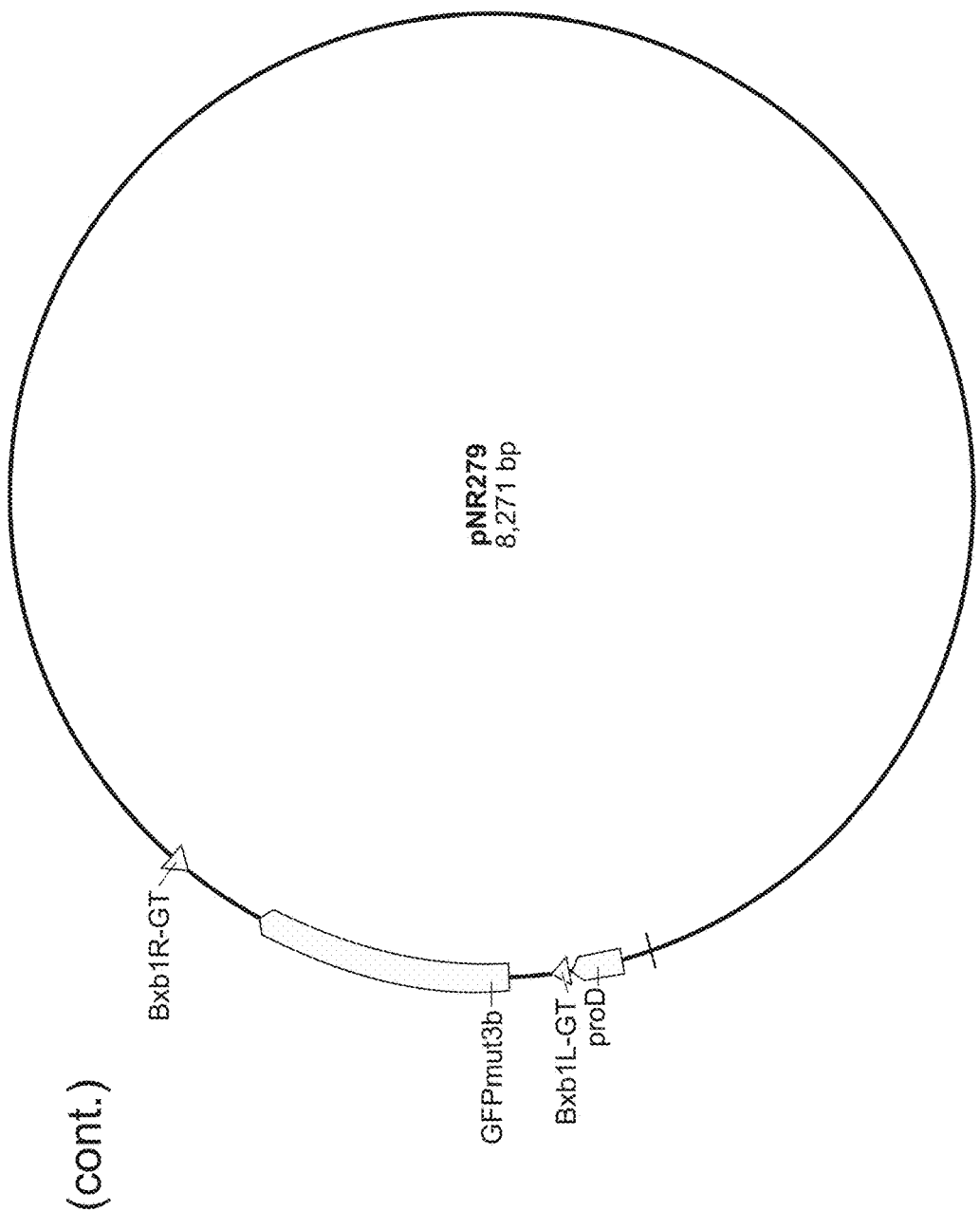
Figure 21:
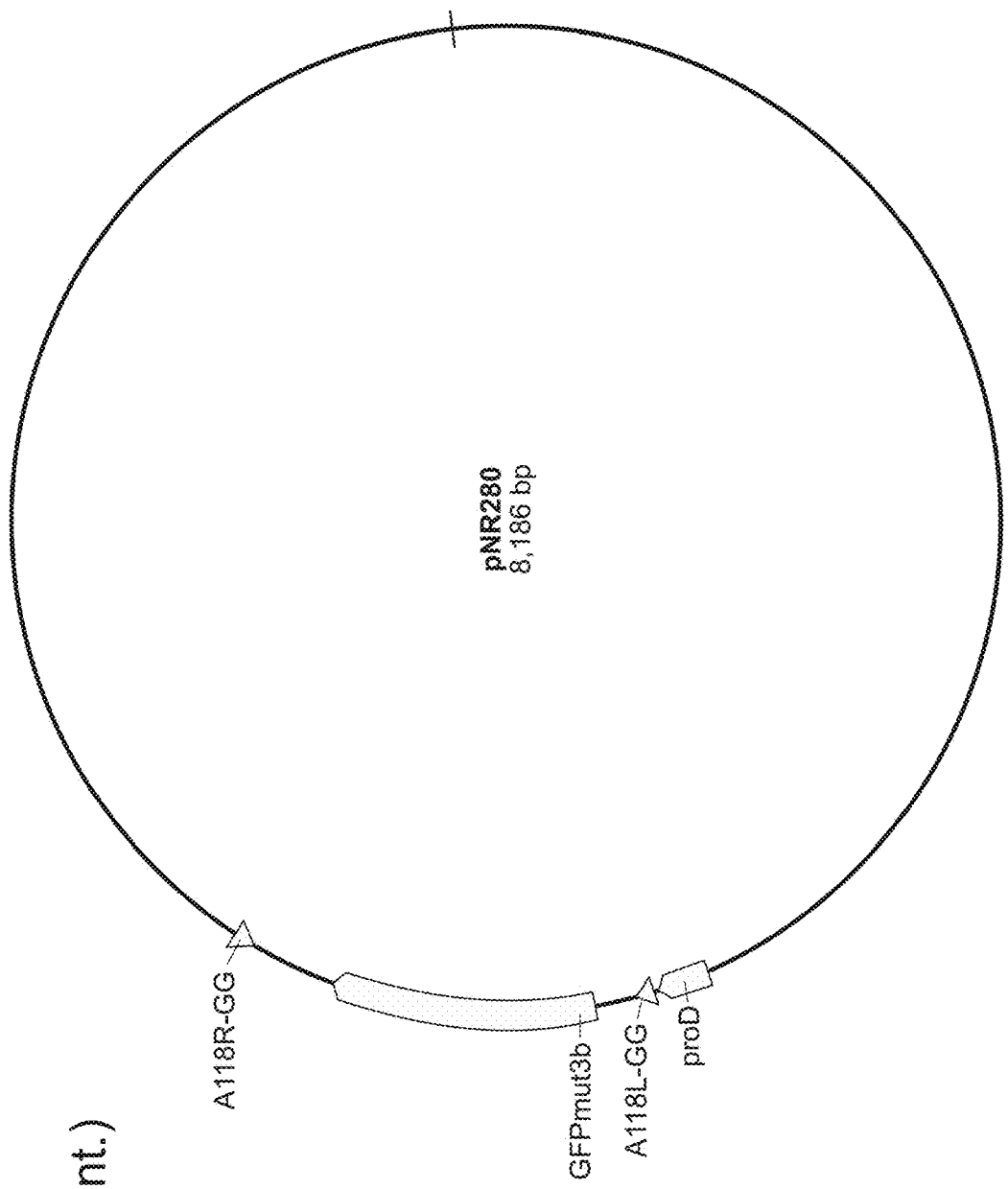
Figure 21:
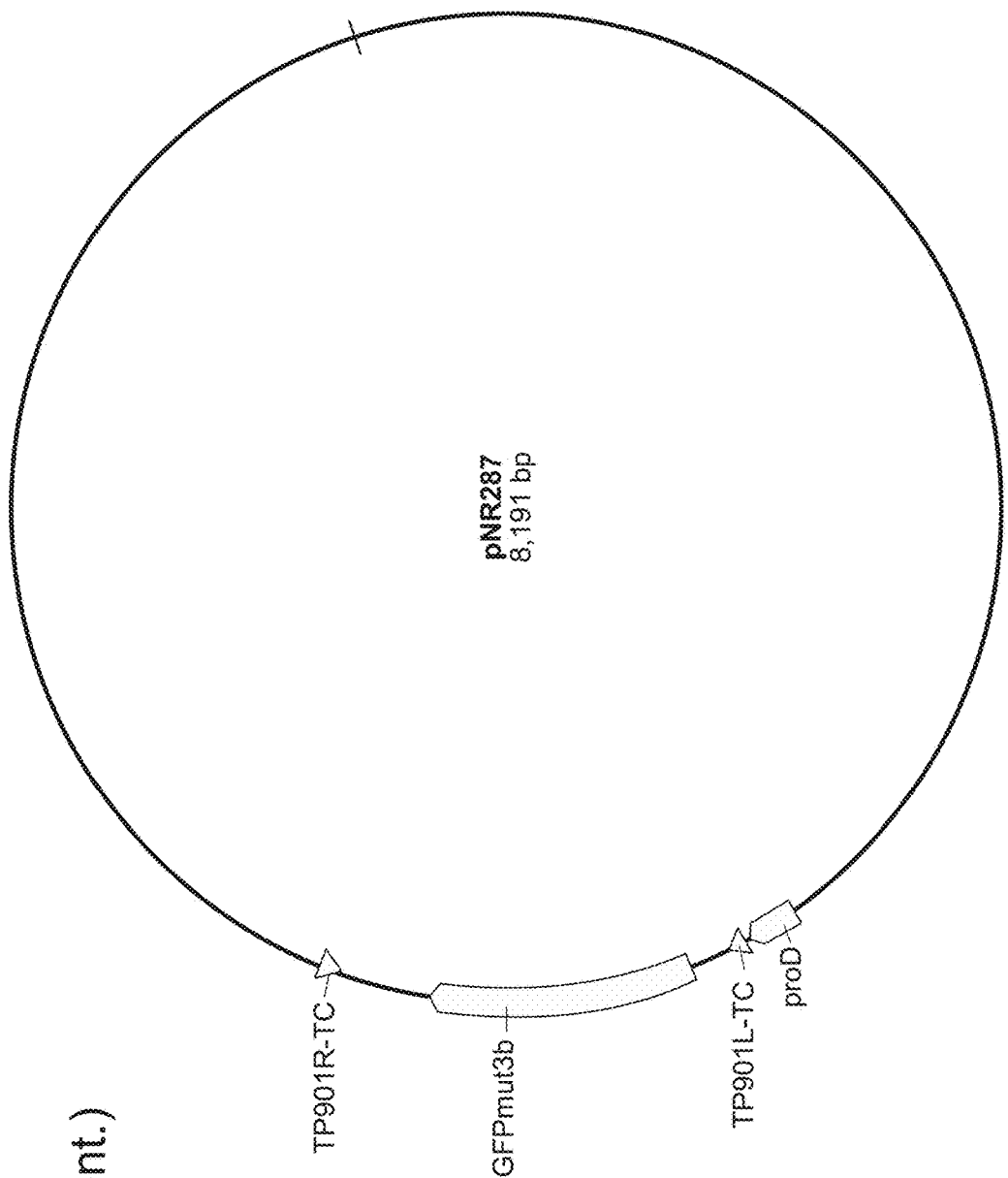

FIG. 21. All plasmids used herein and their relevant parts. pNR64 and pNR220 are input plasmids built on a vector backbone with kanR and ColE1. All other plasmids are built on a BAC vector with camR. Promoters are light green, genes are dark green, terminators are red, attB sites are blue, attP sites are grey, attL sites are black, and attR sites are magenta. The two letters succeeding every recombinase recognition site label are dinucleotide sequences. For input plasmids (pNR64 and pNR220) and recombinase reaction test plasmids (pNR230, pNR239, pNR276, pNR279, pNR280, and pNR287), only the genes and promoters are shown, for the output plasmids (pNR160, pNR188, pNR163, pNR164, pNR165, pNR166, pNR186, pNR187, pNR291, pNR292, and pNR284), only parts on the register are shown. Note that every output plasmid has the same three terminators flanking the register region. These terminators are constructed to keep the register well-insulated and are not actually part of any register design. The plasmid images were generated using the commercial software Geneious R8.

FIG. 22. Register designs that can access a distinct state for every permuted substring of inputs up to N=7 inputs. Each pattern represents a recognition site of a distinct recombinase, so recognition sites of different patterns are orthogonal. Recognition sites of the same pattern but different shapes represent dinucleotide variants and they are also orthogonal. Recognition sites of the same pattern and same shape are an attB-attP pair.

FIG. 23. GRSM database parts. All parts are made up of terminators, promoters, and genes (with 3' end bi-directional terminators). Red terminators are optional—their inclusion will not affect the gene regulation program of the register in which the part is contained. Column 2 gives the identity (ID) of each part as it appears in the database. Not "palindromic" parts (column 3) can also appear in the database in their reverse complement form (identified in the database by a negative sign "−" preceding the part ID). Columns 4 and 5 indicate whether or not ("Y" or "N") each part necessitates terminator read-through (transcription through its terminator in the opposite direction) or promoter read-through (transcription through its promoter(s) in the opposite direction) for the gene regulation program of the register in which the part is contained.

DETAILED DESCRIPTION

Synthetic state machines that record and respond to sequences of signaling and gene regulatory events within a cell could be transformative tools in the study and engineering of complex living systems. For example, in human development, progenitor cells differentiate into specific cell types with disparate functions determined by the timing and order of transcription factor (TF) activation (2, 3). This information has allowed researchers to program human stem cells into differentiated cells (4, 5), and conversely, re-program differentiated cells into stem cells using exogenous, sequential TF activation (6, 7). However, the temporal organization of TF cascades that drive different cell lineages remains largely unknown. State machines that record and actuate gene expression in response to the order of TF activation in individual cells is useful for understanding and modulating these differentiation processes.

Such state machines may also improve our understanding of disease progression, which can also depend on the appearance and order of extracellular and intracellular factors. For example, in cancer, the temporal order of genetic mutations in a tumor can determine its phenotype (8). Similarly, in both somatic diseases and pathogenic infections, pre-adaptation of disease cells to different environmental conditions may affect the way the cells behave and respond to drug treatments (9-12). Integrating state machines into disease models and subsequently analyzing the history of cells that survive treatment is useful for understanding how disease progression affects therapeutic response.

Despite their potential to transform the understanding and engineering of biological systems, complex functional state machines have yet to be implemented in living cells due to a lack of scalable and generalizable frameworks (13). Provided herein is a scalable recombinase-based strategy for implementing state machines in living cells, in which state is encoded in DNA sequence. The direct storage of state information in the DNA sequence ensures that it is maintained stably and with minimal burden to the cell. Recombinases have been used to implement switches (15-19), chemical pulse counters (20), Boolean logic gates integrated with memory (21, 22), and temporal logic (23). Recombinases are used as provided herein to implement scalable state machines, such as those that can distinguish between all possible permuted substrings of a set of inputs with unique gene expression outputs. The state machine implementations of the present disclosure are referred to as "recombinase-based state machines" (RSMs).

Recombinases and Recombination Recognition Sequences

A "recombinase," as used herein, is a site-specific enzyme that recognizes short DNA sequence(s), which sequence(s) are typically between about 30 base pairs (bp) and 40 bp, and that mediates the recombination between these recombinase recognition sequences, which results in the excision, integration, inversion, or exchange of DNA fragments between the recombinase recognition sequences. A "genetic element," as used herein, refers to a sequence of DNA that has a role in gene expression. For example, a promoter, a transcriptional terminator, and a nucleic acid encoding a product (e.g., a protein product) is each considered to be a genetic element.

Recombinases can be classified into two distinct families: serine recombinases (e.g., resolvases and invertases) and tyrosine recombinases (e.g., integrases), based on distinct biochemical properties. Serine recombinases and tyrosine recombinases are further divided into bidirectional recombinases and unidirectional recombinases. Examples of bidirectional serine recombinases include, without limitation, β-six, CinH, ParA and γδ; and examples of unidirectional serine recombinases include, without limitation, Bxb1, φC31, TP901, TG1, φBT1, R4, φRV1, φFC1, MR11, A118, U153 and gp29. Examples of bidirectional tyrosine recombinases include, without limitation, Cre, FLP, and R; and unidirectional tyrosine recombinases include, without limitation, Lambda, HK101, HK022 and pSAM2. The serine and tyrosine recombinase names stem from the conserved nucleophilic amino acid residue that the recombinase uses to attack the DNA and which becomes covalently linked to the DNA during strand exchange. Recombinases have been used for numerous standard biological applications, including the creation of gene knockouts and the solving of sorting problems. In some embodiments, only serine recombinases are used.

The outcome of recombination depends, in part, on the location and orientation of two short repeated DNA sequences that are to be recombined, typically less than 30 bp long. Recombinases bind to these repeated sequences, which are specific to each recombinase, and are herein referred to as "recombinase recognition sequences" or "recombinase recognition sites." Thus, as used herein, a recombinase is "specific for" a recombinase recognition site when the recombinase can mediate inversion or excision between the repeat DNA sequences. As used herein, a recombinase may also be said to recognize its "cognate recombinase recognition sites," which flank an intervening genetic element (e.g., promoter, terminator, or output nucleic acid sequence). A genetic element is said to be "flanked" by recombinase recognition sites when the element is located between and immediately adjacent to two repeated DNA sequences. In some embodiments, the recombinase recognition sites do not overlap each other. However, in other embodiments, recombinase recognition sites do overlap each other, such as described below, which permits greatly increased combinatorial complexity.

Inversion recombination happens between two short, inverted, repeated DNA sequences. A DNA loop formation, assisted by DNA bending proteins, brings the two repeat sequences together, at which point DNA cleavage and ligation occur. This reaction is ATP independent and requires supercoiled DNA. The end result of such an inversion recombination event is that the stretch of DNA between the repeated site inverts (i.e., the stretch of DNA reverses orientation) such that what was the coding strand is now the non-coding strand and vice versa. In such reactions, the DNA is conserved with no net gain or no loss of DNA.

Conversely, integration (excision) recombination occurs between two short, repeated DNA sequences that are oriented in the same direction. In this case, the intervening DNA is excised/removed.

Recombinases can also be classified as irreversible or reversible. As used herein, an "irreversible recombinase" refers to a recombinase that can catalyze recombination between two complementary recombination sites, but cannot catalyze recombination between the hybrid sites that are formed by this recombination without the assistance of an additional factor. Thus, an "irreversible recognition site" refers to a recombinase recognition site that can serve as the first of two DNA recognition sequences for an irreversible recombinase and that is modified to a hybrid recognition site following recombination at that site. A "complementary irreversible recognition site" refers to a recombinase recognition site that can serve as the second of two DNA recognition sequences for an irreversible recombinase and that is modified to a hybrid recombination site following homologous recombination at that site. For example, attB and attP, are the irreversible recombination sites for Bxb1 and phiC31 recombinases—attB is the complementary irreversible recombination site of attP, and vice versa. Recently, it was shown that the attB/attP sites can be mutated to create orthogonal B/P pairs that only interact with each other but not the other mutants. This allows a single recombinase to control the excision or integration or inversion of multiple orthogonal B/P pairs.

The phiC31 (φC31) integrase, for example, catalyzes only the attB×attP the absence of an additional factor not found in eukaryotic cells. The recombinase cannot mediate recombination between the attL and attR hybrid recombination sites that are formed upon recombination between attB and attP. Because recombinases such as the phiC31 integrase cannot alone catalyze the reverse reaction, the phiC31 attB×attP recombination is stable.

Irreversible recombinases, and nucleic acids that encode the irreversible recombinases, are described in the art and can be obtained using routine methods. Examples of irreversible recombinases include, without limitation, phiC31 (φC31) recombinase, coliphage P4 recombinase, coliphage lambda integrase, *Listeria* A118 phage recombinase, and actinophage R4 Sre recombinase, HK101, HK022, pSAM2, Bxb1, TP901, TG1, φBT1, φRV1, φFC1, MR11, U153 and gp29.

Conversely, a "reversible recombinase" refers to a recombinase that can catalyze recombination between two complementary recombinase recognition sites and, without the assistance of an additional factor, can catalyze recombination between the sites that are formed by the initial recombination event, thereby reversing it. The product-sites generated by recombination are themselves substrates for subsequent recombination. Examples of reversible recombinase systems include, without limitation, the Cre-lox and the Flp-frt systems, R, β-six, CinH, ParA and γδ.

The recombinases provided herein are not meant to be exclusive examples of recombinases that can be used in embodiments of the present disclosure. The complexity of logic and memory systems of the present disclosure can be expanded by mining databases for new orthogonal recombinases or designing synthetic recombinases with defined DNA specificities. Other examples of recombinases that are useful are known to those of skill in the art, and any new recombinase that is discovered or generated is expected to be able to be used in the different embodiments of the present disclosure.

In some embodiments, the recombinase is serine recombinase. Thus, in some embodiments, the recombinase is considered to be irreversible. In some embodiments, the recombinase is a tyrosine recombinase. Thus, in some embodiments, the recombinase is considered to be reversible.

Promoters

As used herein, a "promoter" refers to a control region of a nucleic acid sequence at which initiation and rate of transcription of the remainder of a nucleic acid sequence are controlled. A promoter may also contain subregions at which regulatory proteins and molecules may bind, such as RNA polymerase and other transcription factors. Promoters may be constitutive, inducible, activatable, repressible, tissue-specific or any combination thereof.

A promoter drives expression or drives transcription of the nucleic acid sequence that it regulates. As used herein, "operably linked" and "under control" indicate that a promoter is in a correct functional location and/or orientation in relation to a nucleic acid sequence it regulates to control transcriptional initiation and/or expression of that sequence. An "inverted promoter," as described above, is a promoter in which the nucleic acid sequence is in the reverse orientation, such that what was the coding strand is now the non-coding strand, and vice versa. Inverted promoter sequences can be used in various embodiments of the present disclosure to regulate a particular state. Thus, in some embodiments, the promoter is an inverted promoter, flanked by complementary recombinase recognition sites that, upon recombination of the sites, inverts to the correct orientation (e.g., and drives expression of an operably linked nucleic acid sequence). In some embodiments of the present disclosure, a promoter may or may not be used in conjunction with an "enhancer," which refers to a cis-acting regulatory sequence involved in the transcriptional activation of a nucleic acid sequence downstream of the promoter. The enhancer may be located at any functional location before or after the promoter and/or the encoded nucleic acid.

A promoter is classified as strong or weak according to its affinity for RNA polymerase (and/or sigma factor); this is related to how closely the promoter sequence resembles the ideal consensus sequence for the polymerase. The strength of a promoter may depend on whether initiation of transcription occurs at that promoter with high or low frequency. Different promoters with different strengths may be used to construct logic gates with different digitally settable levels of gene output expression (e.g., the level of gene expression initiated from a weak promoter is lower than the level of gene expression initiated from a strong promoter). For example, the data shown in FIGS. 26A-26C demonstrate that various digital combinations of the input inducers result in multiple levels of analog gene expression outputs based on the varying strengths of the promoters used and the sum of their respective outputs.

A promoter may be one naturally associated with a gene or sequence, as may be obtained by isolating the 5' non-coding sequences located upstream of the coding segment and/or exon of a given gene or sequence. Such a promoter can be referred to as "endogenous." Similarly, an enhancer may be one naturally associated with a nucleic acid sequence, located either downstream or upstream of that sequence.

In some embodiments, a coding nucleic acid segment may be positioned under the control of a recombinant or heterologous promoter, which refers to a promoter that is not normally associated with the encoded nucleic acid sequence in its natural environment. A recombinant or heterologous enhancer refers to an enhancer not normally associated with a nucleic acid sequence in its natural environment. Such promoters or enhancers may include promoters or enhancers of other genes; promoters or enhancers isolated from any other prokaryotic, viral or eukaryotic cell; and synthetic promoters or enhancers that are not "naturally occurring" such as, for example, those that contain different elements of different transcriptional regulatory regions and/or mutations that alter expression through methods of genetic engineering that are known in the art. In addition to producing nucleic acid sequences of promoters and enhancers synthetically, sequences may be produced using recombinant cloning and/or nucleic acid amplification technology, including PCR, in connection with the present disclosure (see U.S. Pat. Nos. 4,683,202 and 5,928,906). Furthermore, control sequences that direct transcription and/or expression of sequences within non-nuclear organelles such as mitochondria, chloroplasts and the like, may be used in accordance with the present disclosure.

Inducible Promoters

As used herein, an "inducible promoter" is one that is characterized by initiating or enhancing transcriptional activity when in the presence of, influenced by or contacted by an inducer or inducing agent. An "inducer" or "inducing agent" may be endogenous or a normally exogenous compound or protein that is administered in such a way as to be active in inducing transcriptional activity from the inducible promoter.

Inducible promoters for use in accordance with the present disclosure may function in both prokaryotic and eukaryotic host organisms. In some embodiments, mammalian inducible promoters are used. Examples of mammalian inducible promoters for use herein include, without limitation, promoter type $P_{Act}$:$P_{AIR}$, $P_{ART}$, $P_{BIT}$, $P_{CR5}$, $P_{CTA}$, $P_{ETR}$, $P_{NIC}$, $P_{PIP}$, $P_{ROP}$, $P_{SPA}$/$P_{SCA}$, $P_{TET}$, $P_{TtgR}$, promoter type $P_{Rep}$:$P_{CuO}$, $P_{ETR}$ ON8, $P_{NIC}$, $P_{PIR}$ ON, $P_{SCA}$ ON8, $P_{TetO}$, $P_{UREX8}$, promoter type $P_{Hyb}$:tetO$_7$-ETR$_8$-$P_{hCMVmin}$, tetO$_7$-PIR$_3$-ETR$_8$-$P_{hCMVmin}$, and scbR$_8$-PIR$_3$-$P_{hCMVmin}$. In some embodiments, inducible promoters from other organisms, as well as synthetic promoters designed to function in a prokaryotic (e.g., $P_{PhlF}$, $P_{BAD}$ and $P_{LetO}$) or eukaryotic host may be used. Examples of non-mammalian inducible promoters for use herein include, without limitation, Lentivirus promoters (e.g., EFα, CMV, Human SynapsinI (hSynI), CaMKIIα, hGFAP and TPH-2) and Adeno-Associated Virus promoters (e.g., CaMKIIα (AAV5), hSynI (AAV2), hThy1 (AAV5), fSST (AAV1), hGFAP (AAV5, AAV8), MBP (AAV8), SST (AAV2)). One important functional characteristic of the inducible promoters of the present disclosure is their inducibility by exposure to an externally applied inducer.

The administration or removal of an inducer results in a switch between the "ON" or "OFF" states of the transcription of the operably linked nucleic acid sequence (e.g., nucleic acid encoding a recombinase). Thus, as used herein, the "ON" state of a promoter operably linked to a nucleic acid sequence refers to the state when the promoter is actively driving transcription of the nucleic acid sequence (i.e., the linked nucleic acid sequence is expressed). Conversely, the "OFF" state of a promoter operably linked, or conditionally operably linked, to a nucleic acid sequence refers to the state when the promoter is not actively driving transcription of the nucleic acid sequence (i.e., the linked nucleic acid sequence is not expressed).

An inducible promoter for use in accordance with the present disclosure may be induced by (or repressed by) one or more physiological condition(s), such as changes in pH, temperature, radiation, osmotic pressure, saline gradients, cell surface binding, and the concentration of one or more extrinsic or intrinsic inducing agent(s). The extrinsic inducer or inducing agent may comprise, without limitation, amino acids and amino acid analogs, saccharides and polysaccharides, nucleic acids, protein transcriptional activators and repressors, cytokines, toxins, petroleum-based compounds, metal containing compounds, salts, ions, enzyme substrate analogs, hormones or combinations thereof. The condition(s) and/or agent(s) that induce or repress an inducible promoter can be input(s) of the logic gates described herein.

Inducible promoters for use in accordance with the present disclosure include any inducible promoter described herein or known to one of ordinary skill in the art. Examples of inducible promoters include, without limitation, chemically/biochemically-regulated and physically-regulated promoters such as alcohol-regulated promoters, tetracycline-regulated promoters (e.g., anhydrotetracycline (aTc)-responsive promoters and other tetracycline-responsive promoter systems, which include a tetracycline repressor protein (tetR), a tetracycline operator sequence (tetO) and a tetracycline transactivator fusion protein (tTA)), steroid-regulated promoters (e.g., promoters based on the rat glucocorticoid receptor, human estrogen receptor, moth ecdysone receptors, and promoters from the steroid/retinoid/thyroid receptor superfamily), metal-regulated promoters (e.g., promoters derived from metallothionein (proteins that bind and sequester metal ions) genes from yeast, mouse and human), pathogenesis-regulated promoters (e.g., induced by salicylic acid, ethylene or benzothiadiazole (BTH)), temperature/heat-inducible promoters (e.g., heat shock promoters), and light-regulated promoters (e.g., light responsive promoters from plant cells).

In some embodiments, the inducer used in accordance with the present disclosure is an N-acyl homoserine lactone (AHL), which is a class of signaling molecules involved in bacterial quorum sensing. Quorum sensing is a method of communication between bacteria that enables the coordination of group based behavior based on population density. AHL can diffuse across cell membranes and is stable in growth media over a range of pH values. AHL can bind to transcriptional activators such as LuxR and stimulate transcription from cognate promoters.

In some embodiments, the inducer used in accordance with the present disclosure is anhydrotetracycline (aTc), which is a derivative of tetracycline that exhibits no antibiotic activity and is designed for use with tetracycline-controlled gene expression systems, for example, in bacteria.

Other inducible promoter systems may be used in accordance with the present disclosure.

Terminators

Provided herein are terminator sequences for use in some embodiments of the present disclosure. A "terminator" or "terminator sequence," as used herein, is a nucleic acid sequence that causes transcription to stop. A terminator may be unidirectional or bidirectional. It is comprised of a DNA sequence involved in specific termination of an RNA transcript by an RNA polymerase. A terminator sequence prevents transcriptional activation of downstream nucleic acid sequences by upstream promoters. Thus, in certain embodiments, a terminator that ends the production of an RNA transcript is contemplated. A terminator may be necessary in vivo to achieve desirable output expression levels (e.g., low output levels).

The most commonly used type of terminator is a forward terminator. When placed downstream of a nucleic acid sequence that is usually transcribed, a forward transcriptional terminator will cause transcription to abort. In some embodiments, bidirectional transcriptional terminators are provided, which usually cause transcription to terminate on both the forward and reverse strand. In some embodiments, reverse transcriptional terminators are provided, which usually terminate transcription on the reverse strand only.

In prokaryotic systems, terminators usually fall into two categories (1) rho-independent terminators and (2) rho-dependent terminators. Rho-independent terminators are generally composed of palindromic sequence that forms a stem loop rich in G-C base pairs followed by several T bases. Without wishing to be bound by theory, the conventional model of transcriptional termination is that the stem loop causes RNA polymerase to pause, and transcription of the poly-A tail causes the RNA:DNA duplex to unwind and dissociate from RNA polymerase.

In eukaryotic systems, the terminator region may comprise specific DNA sequences that permit site-specific cleavage of the new transcript so as to expose a polyadenylation site. This signals a specialized endogenous polymerase to add a stretch of about 200 A residues (polyA) to the 3' end of the transcript. RNA molecules modified with this polyA tail appear to more stable and are translated more efficiently. Thus, in some embodiments involving eukaryotes, a terminator may comprise a signal for the cleavage of the RNA. In some embodiments, the terminator signal promotes polyadenylation of the message. The terminator and/or polyadenylation site elements may serve to enhance output nucleic acid levels and/or to minimize read through between nucleic acids.

Terminators for use in accordance with the present disclosure include any terminator of transcription described herein or known to one of ordinary skill in the art. Examples of terminators include, without limitation, the termination sequences of genes such as, for example, the bovine growth hormone terminator, and viral termination sequences such as, for example, the SV40 terminator, spy, yejM, secG-leuU, thrLABC, rrnB T1, hisLGDCBHAFI, metZWV, rrnC, xapR, aspA and arcA terminator. In some embodiments, the termination signal may be a sequence that cannot be transcribed or translated, such as those resulting from a sequence truncation.

Other inducible promoter systems may be used in accordance with the present disclosure.

Cells

A cell to be engineered for use as provided herein may be any cell or host cell. As defined herein, a "cell" or "cellular system" is the basic structural and functional unit of all known independently living organisms. It is the smallest unit of life that is classified as a living thing. Some organisms, such as most bacteria, are unicellular (consist of a single cell). Other organisms, such as humans, are multicellular.

In some embodiments, a cell for use in accordance with the invention is a prokaryotic cell, which may comprise a cell envelope and a cytoplasmic region that contains the cell genome (DNA) and ribosomes and various sorts of inclusions. In some embodiments, the cells are bacterial cells. As used herein, the term "bacteria" encompasses all variants of bacteria, for example, prokaryotic organisms and cyanobacteria. Bacteria are small (typical linear dimensions of around 1 micron), non-compartmentalized, with circular DNA and ribosomes of 70S. The term bacteria also includes bacterial subdivisions of Eubacteria and Archaebacteria. Eubacteria can be further subdivided into gram-positive and gram-negative Eubacteria, which depend upon a difference in cell wall structure. Also included herein are those classified based on gross morphology alone (e.g., cocci, bacilli). In some embodiments, the bacterial cells are gram-negative cells, and in some embodiments, the bacterial cells are gram-positive cells. Examples of bacterial cells that may be used in accordance with the invention include, without limitation, cells from *Yersinia* spp., *Escherichia* spp., *Klebsiella* spp., *Bordetella* spp., *Neisseria* spp., *Aeromonas* spp., *Franciesella* spp., *Corynebacterium* spp., *Citrobacter* spp., *Chlamydia* spp., *Hemophilus* spp., *Brucella* spp., *Mycobacterium* spp., *Legionella* spp., *Rhodococcus* spp., *Pseudomonas* spp., *Helicobacter* spp., *Salmonella* spp., *Vibrio* spp., *Bacillus* spp., *Erysipelothrix* spp., *Salmonella* spp., *Stremtomyces* spp. In some embodiments, the bacterial cells are from *Staphylococcus aureus, Bacillus subtilis, Clostridium butyricum, Brevibacterium lactofermentum, Streptococcus agalactiae, Lactococcus lactis, Leuconostoc lactis, Streptomyces, Actinobacillus actinobycetemcomitans, Bacteroides, cyanobacteria, Escherichia coli, Helobacter pylori, Selnomonas ruminatium, Shigella sonnei, Zymomonas mobilis, Mycoplasma mycoides, Treponema denticola, Bacillus thuringiensis, Staphylococcus lugdunensis, Leuconostoc oenos, Corynebacterium xerosis, Lactobacillus planta rum, Streptococcus faecalis, Bacillus coagulans, Bacillus ceretus, Bacillus popillae, Synechocystis* strain PCC6803, *Bacillus liquefaciens, Pyrococcus abyssi, Selenomonas nominantium, Lactobacillus hilgardii, Streptococcus ferus, Lactobacillus pentosus, Bacteroides fragilis, Staphylococcus epidermidis, Zymomonas mobilis, Streptomyces phaechromogenes, Streptomyces ghanaenis, Halobacterium* strain GRB, or *Halobaferax* sp. strain Aa2.2.

In some embodiments, a cell for use in accordance with the present disclosure is a eukaryotic cell, which comprises membrane-bound compartments in which specific metabolic activities take place, such as a nucleus. Examples of eukaryotic cells for use in accordance with the invention include, without limitation, mammalian cells, insect cells, yeast cells (e.g., *Saccharomyces cerevisiae*) and plant cells. In some embodiments, the eukaryotic cells are from a vertebrate animal. Examples of vertebrate cells for use in accordance with the invention include, without limitation, reproductive cells including sperm, ova and embryonic cells, and non-reproductive cells, including kidney, lung, spleen, lymphoid, cardiac, gastric, intestinal, pancreatic, muscle, bone, neural, brain and epithelial cells. Stem cells, including embryonic stem cells, can also be used.

As detailed in the following Examples, state machines were created by using recombinases to manipulate DNA registers assembled out of overlapping and orthogonal recombinase recognition sites. A mathematical framework was used to analyze the information capacity and scalability of the state machines and understand their limits. For a fixed number of inputs, the information capacity enabled by RSMs is much greater than that of traditional combinational circuits. Furthermore, a rich database accessible to the scientific community (in Example 14 and Example 15) was created to enable the automatic design of GRSM registers that implement 2-input, 5-state gene regulation programs.

The RSM framework was validated by building 2-input, 5-state and 3-input, 16-state RSMs, testing them with Sanger sequencing and qPCR, and applying them to build state-dependent gene regulation programs. The state machines of the present disclosure differ from other strategies for genetic programming, such as combinational Boolean logic gates that are stateless (33-44), cell counters that do not integrate multiple inputs (20), temporal logic circuits that are unable to report on all possible input identities and permutations in a single circuit (23), and other multi-input recombinase-based circuits that do not use overlapping recombinase recognition sites and thus cannot perform order-dependent input processing (21, 22).

Though RSMs were implemented in bacteria, the framework provided herein will be extensible to other organisms in which recombinases are functional. For example, the large-serine recombinases used here (BxbI, TP901, and A118), as well as φC31, φFC1, φRV1, U153, and R4 catalyze recombination in mammalian cells (45-48) may be used.

Identification of additional recombinases that function in different organisms should expand the applicability of our framework. The incorporation of reversible recombination events through proteins such as Recombination Directionality Factors should also enable reversible transitions between gene regulatory states (15). Depending on desired applications, the prototypical inducible promoters used here to drive the RSMs may be replaced by sensors that correspond to the desired signals to be recorded. Such sensors do not necessarily have to be based on transcriptional regulation, as long as they can control recombinase activity.

The integration of RSMs into complex systems will enable researchers to investigate temporally distributed events without the need for continual monitoring and/or sampling. For example, by incorporating RSMs into tumor models, scientists may record the identity and order of oncogene activation and tumor suppressor deactivation events in individual cancer cells, and further correlate this information to phenotypic data from transcriptomic analysis or drug assays. In a recent study of myeloproliferative neoplasms containing mutations in both TET2 (a tumor suppressor) and JAK2 (a proto-oncogene), it was discovered that the order in which the mutations occurred played a role in determining disease phenotype, including sensitivity to therapy (8). This research underscores the potential impact of order-dependencies in other malignancies and the importance of studying them. Cell sorting based on reporter gene expression from GRSMs could be used to separate cells exposed to different identities and orders of gene regulatory perturbations, which could then be further studied to determine functional cellular differences.

Aside from recording and responding to naturally occurring signals, RSMs have applications when the signals that control them are applied by a user. For example, RSMs can generate gene expression not based on simultaneous combinations of inputs, but also by orders of inputs. Thus, they may be useful to bioengineers for programming multiple functions in cell strains for which there are limited numbers of control signals. For example, they may be used to program cell differentiation down many different cell fate paths based on the order and identities of just a few inputs.

Beyond applications to biological research and engineering, the work described herein has also revealed an interesting mathematical structure to recombinase systems. At first glance, the non-commutative behavior of recombinase operations suggests that there might be a super exponential relationship between the number of possible states in a RSM and the number of recombinases it incorporates. Instead our results show that the number of states is bound exponentially (Box 1, Example 7 and Example 8).

EXAMPLES

Example 1. Recombinase-Based State Machine Parts and Operations

Figure 1:
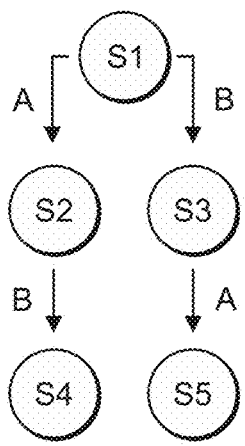
FIG. 1. Example of a state machine. Nodes represent states and arrows represent transitions between states mediated by inputs. Each of the possible permuted substrings of the two inputs "A" and "B" generates a unique state.
Figure 2A:
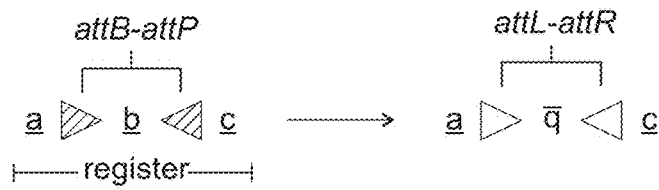
FIGS. 2A-2D. Rules of recombination on a register. The register is depicted as an array of underscored alphabet symbols (arbitrary DNA) and shape symbols (recognition sites). (A) If sites in an attB-attP pair are anti-aligned, then the DNA between them is inverted during recombination. (B) If sites in an attB-attP pair are aligned, then the DNA between them is excised during recombination. (C) Multiple inputs can drive distinct recombinases that operate on their own attB-attP pairs. In this example, input "A" drives the orange recombinase and input "B" drives the blue recombinase. (D) Multiple, orthogonal attB-attP pairs for a given recombinase can be placed on a register. Here distinct shapes denote two pairs of attB-attP. Up to 6 orthogonal and directional attB-attP pairs can be created per recombinase (31).
Figure 2B:

In a RSM, chemical signals serve as inputs and state is defined by the DNA sequence within a prescribed region of DNA, termed the "register". Chemical signals mediate state transitions by inducing the expression of large serine recombinases that catalyze recombination events on the register, thereby changing the state. Specifically, each recombinase recognizes a cognate pair of DNA recognition sites on the register, attP (derived from a phage) and attB (derived from its bacterial host), and carries out a recombination reaction between them, yielding attL and attR sites (made up of conjoined halves of attB and attP) (24, 25). In the absence of extra co-factors, this reaction is irreversible (Example 6 and FIGS. 8A-8B) (26-28). Each site in a cognate attB-attP (attB with attP) pair has a matching central dinucleotide that determines its polarity (29, 30). If the two sites are anti-aligned (oriented with opposite polarity) on the register, then the result of their recombination is the inversion of the DNA between them (FIG. 2A; FIG. S2A). Alternatively, if the two sites are aligned (oriented with the same polarity) on the register, then the result of their recombination is the excision of the DNA between them (FIG. 2A; FIG. S2B). DNA segments that are excised from the register are assumed to be lost due to a lack of origin of replication.

Figure 2C:
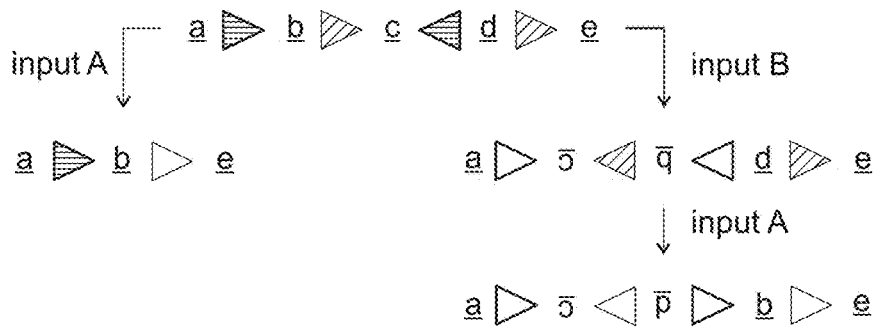

When there are multiple inputs to a RSM, they can each drive distinct recombinases that only operate on their own attB-attP pairs. At least 25 (putatively orthogonal) large-serine recombinases have been described and tested in the literature (18, 25), and bioinformatics mining can be used to discover even more (18). Recognition sites for multiple recombinases may be arranged in several different ways on the register. If attB-attP pairs from different recombinases are nested or overlapping, then the operation of one recombinase can affect the operation of subsequent recombinases—either by rearranging the relative orientation of their attB and attP sites, or excising one or both sites in a pair from the register, thereby precluding any type of downstream operation on these sites. For example, if we consider the initial register design in FIG. 2C, applying input "B→A" leads to a unique DNA sequence, but applying "A→B" leads to the same DNA sequence we would expect if we only applied "A", since the "A"-driven recombinase excises a site for the "B"-driven recombinase.

Figure 2D:

We measure the "information capacity" of a RSM by the number of distinct states it can access, and hence the number of permuted substrings of inputs it can distinguish. Given the non-commutative nature of recombinase operations on a register, one might naively believe that the information capacity of RSMs would behave like N! for N inputs. But, if a RSM is designed such that each input-driven recombinase only has one attB-attP pair on the register, the information capacity of the RSM never exceeds $2^N$—the result we would expect if recombinase operations were commutative (Box 1, Example 7). To circumvent this information bottleneck, registers must be designed with multiple pairs of orthogonal attB-attP per recombinase. Orthogonal attB-attP pairs for a recombinase can be engineered by mutating the central dinucleotide of each site in the native attB-attP pair (29-31). Pairs of sites with the same central dinucleotide sequence should recombine, but should not recombine if the central dinucleotide sequences do not match (FIG. 2D, FIG. S2C).

Example 2. Building a 2-Input, 5-State Recombinase-Based State Machine

To implement a RSM that enters a different state (5 in total) for every permuted substring of 2 inputs, it was sufficient to use two orthogonal attB-attP pairs for one recombinase and one attB-attP pair for the other recombinase. The RSM design and a detailed representation of its state diagram is shown in FIG. 3A. This RSM is composed of two plasmids: an input plasmid and an output plasmid. The input plasmid, at a high copy number, expresses two large-serine recombinases, BxbI and TP901, from the Anhydrotetracycline (ATc)-inducible $P_{LetO}$ promoter and the Arabinose (Ara)-inducible $P_{BAD}$ promoter, respectively. The output plasmid, at a single copy number, contains the register that is modified by the recombinases expressed from the input plasmid.

The register is initially composed of an aligned BxbI attB-attP pair and two anti-aligned and orthogonal TP901 attB-attP pairs. If ATc is introduced first to the system, then BxbI is expressed and excises the DNA inside of its cognate recognition site pair, which includes a recognition site for TP901. Subsequent introduction of Ara to the system induces the expression of TP901, which recombines its cognate recognition sites on the outer edge of the register, thus inverting everything in between. Conversely, if Ara is introduced first to the system, then the outer TP901 sites invert everything between the edges of the register and the inner TP901 sites invert an inner portion of the register, thus setting the BxbI recognition sites into an anti-aligned configuration. Subsequent application of ATc to the system inverts the sequence of DNA between the BxbI sites. As a result, each permuted substring of the inputs yields a distinct DNA sequence on the register.

To evaluate the performance of the RSM in *Escherichia coli* (*E. coli*), we grew 5 populations of cells that were treated with all 5 permuted substrings of the inputs ATc and Ara (no input, ATc only, Ara only, ATc→Ara, and Ara→ATc). We Sanger sequenced the register in colonies of at least 22 cells from each population in each of three biological replicates to determine the percent of cells with the expected DNA sequence (FIG. 3B) (32). At least 97% of all cells treated with each permuted substring of inputs adopted the expected state, thus confirming the fidelity of our RSM. Table 1 provides information for the sequenced registers that were not in the expected state.

Because our Sanger sequencing read-out of state was low-throughput, we also developed a quantitative-PCR (qPCR)-based method to conveniently interrogate state on a population-wide level. The excision and inversion of DNA segments in our register permit the design of primer pairs that amplify in some states but not others. We created a computer program, the PCR-based State Interrogation Tool (PSIT), to identify all possible sets of primer pairs that uniquely identify each state of a given register (FIG. 10, Example 16). For our 2-input, 5-state RSM, we chose a set of 3 primer pairs and performed qPCR on DNA that was isolated from each population of cells treated with all possible permuted substrings of the ATc and Ara inputs. The fractional amount of register DNA amplified was calculated for each primer pair in our set and compared to what we would expect if all cells in each population adopted just one of the 5 possible states (32). In agreement with our sequencing results, the qPCR measurements of all experimental populations were most similar to what we would expect if all cells in each population adopted their expected state (FIG. 11).

Example 3. Scaling Recombinase-Based State Machines

We developed a modular register design strategy for building RSMs that enter a distinct state for every permuted substring of inputs (approximately eN! states for N inputs, see Example 9; Example 10; FIG. 22). For N inputs, the design strategy uses N−1 recognition sites per recombinase, and hence is limited to register designs for up to 7 inputs (13700 states) since only 6 orthogonal and directional attB-attP pairs can be created per large-serine recombinase (31).

Figure 3B:
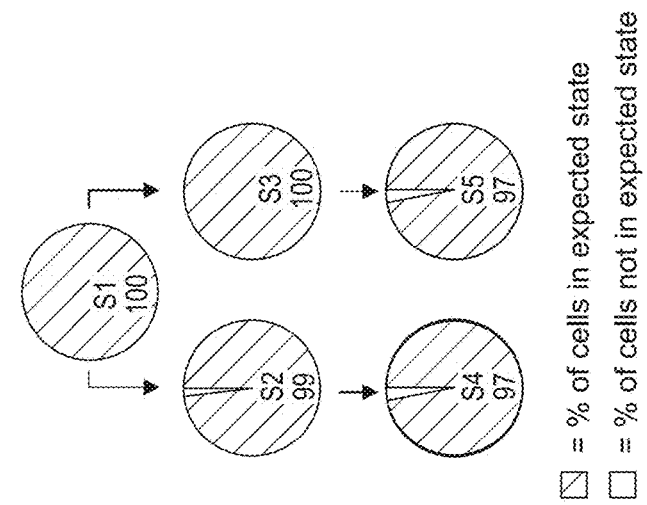
FIGS. 3A-3B. Designing and validating a 2-input, 5-state RSM. (A) Depicted are the two plasmids used to implement the RSM (top) and a detailed state diagram demonstrating the resulting register for each permuted substring of the two inputs (aTc and Ara; bottom). (B) The performance of the RSM in E. coli. Nodes represent populations of cells induced with permuted substrings of the inputs ATc (orange arrow) and Ara (blue arrow). Cultures were treated with saturating concentrations of each input (250 ng/mL ATc or 1% w/v Ara) at 30° C. for 18 hours in three biological replicates. Node labels indicate the expected state (corresponding to panel A) and the percent of cells in that state as determined by Sanger sequencing of colonies from individual cells in each population (at least 66 cells totaled over all three biological replicates).
Figure 3A:
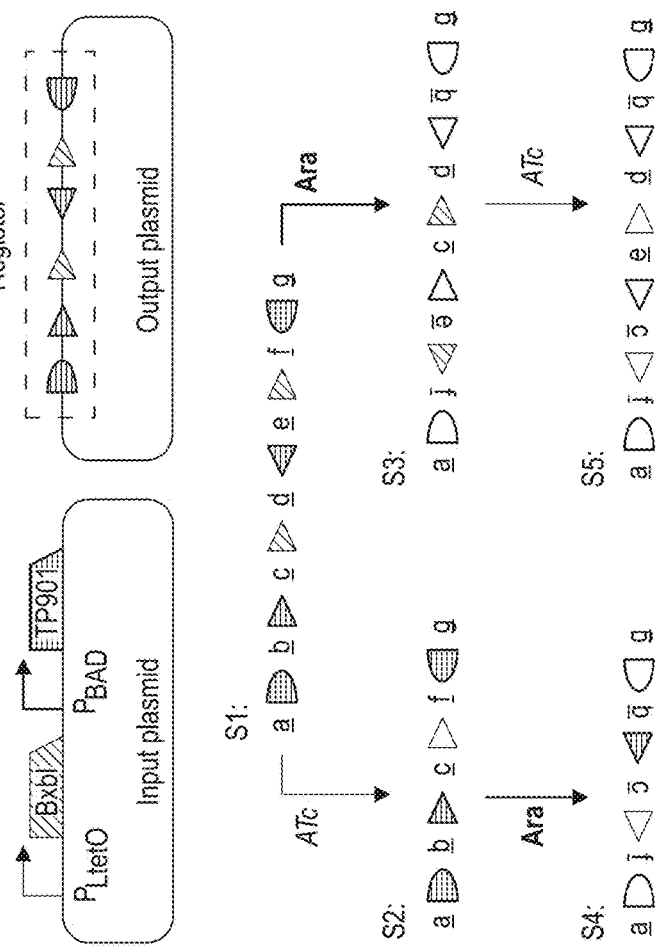
Figures 4A, 4B:
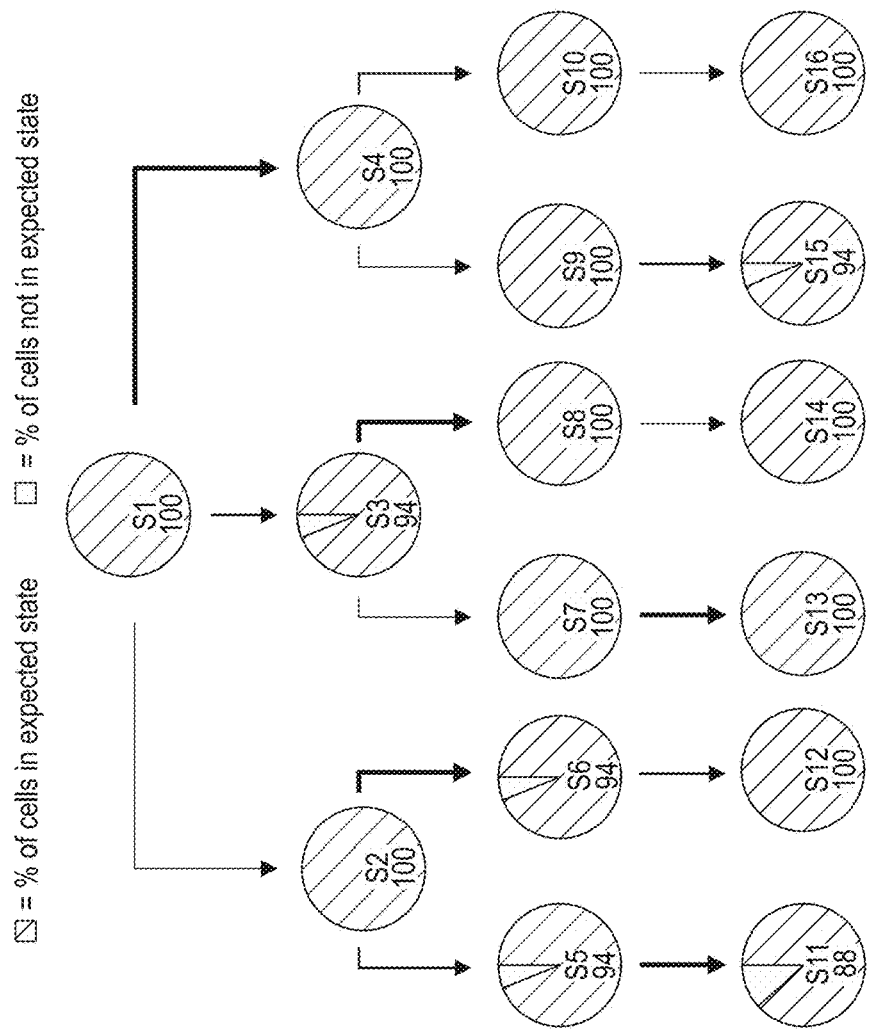
FIGS. 4A-4B. Scaling to a 3-input, 16-state RSM. (A) The two plasmids used to implement the RSM. aTc, Ara, and DAPG induce expression of BxbI, TP901, and A118 recombinases, respectively. A detailed state diagram of the register on the output plasmid is shown in FIG. 12. (B) The performance of the RSM in E. coli. Nodes represent populations of cells induced with all permuted substrings of the inputs ATc (orange arrow), Ara (blue arrow), and DAPG (purple arrow). Cultures were treated with saturating concentrations of each input (250 ng/mL ATc, 1% w/v Ara, or 25 µM DAPG) at 30° C. for 24 hours in three biological replicates. Node labels indicate the expected state (corresponding to FIG. 12) and the percent of cells in that state as determined by Sanger sequencing of colonies from individual cells in each population (at least 17 cells totaled over all three biological replicates).

Because the 2-input, 5-state RSM shown in FIG. 3A only represents a marginal improvement in information capacity over 2-input, 4-state systems achievable by combinational computation, we sought to further demonstrate the information capacity enabled by our RSM framework by scaling to a 3-input, 16-state RSM (FIG. 4A and FIG. 12). The input plasmid for this state machine expresses an additional recombinase, A118, under a 2,4-diacetylphloroglucinol (DAPG)-inducible $P_{PhlF}$ promoter system, and its register uses two orthogonal attB-attP pairs for each of the 3 recombinases (following the design strategy in Example 10).

To evaluate the performance of this RSM in *E. coli*, we grew 16 populations of cells that were treated with all 16 permuted substrings of the inputs ATc, Ara, and DAPG. We sequenced the register in colonies of 5-6 cells from each population in each of three biological replicates to determine the percent of cells with the expected DNA sequence (FIG. 4B) (32). In most populations, 100% of the cells adopted their expected state, and even in the worst-performing population (ATc→Ara→DAPG), 88% of cells adopted their expected state. Table 1 provides information for the sequenced registers that were not in the expected state. We also measured the predominant state of each population by qPCR with a set of 6 primer pairs elucidated by PSIT (32). In agreement with the sequencing results, the qPCR measurements for all experimental populations were most similar to what we would expect if all cells in each population adopted their expected state (FIG. 13).

Example 4. Gene-Regulatory Recombinase-Based State Machines

Our state machine framework enables the creation of state-dependent gene regulation programs that specify which genes should be expressed or not expressed in each state. This could be useful for a wide range of biological applications, such as programming synthetic differentiation cascades, encoding the identities and order of biological events into selectable or sortable reporters, or targeting genetic perturbations to cells that experience a particular order of biological events. Gene regulation programs can be implemented by incorporating genetic regulatory elements, such as promoters, terminators, and genes, into the registers of our RSMs. The re-arrangement of these elements in each state should then alter gene expression in a predictable manner. Such RSMs are a biological realization of Moore Machines from automata theory, where each state is associated with a set of outputs (1). Here we refer to them as gene-regulatory recombinase-based state machines (GRSMs).

To help researchers design circuits for desired gene regulation programs, we created a large, searchable database of 2-input, 5-state GRSM registers. To compile this "GRSM database" (FIG. 5), we first enumerated all possible registers that could result from interleaving functionally distinct parts (made from terminators, constitutive promoters, and genes; see Example 11 for more details) before and after each recombinase recognition site in our validated 5-state register from FIG. 3A. We evaluated each state of each register for gene transcription, and aggregated registers that implement the same gene regulation program. During this evaluation step, we assumed that all genes had bi-directional terminators on their 3' ends, thus disallowing the possibility of an RNA polymerase traversing a gene (in either direction) to transcribe another gene. We also assumed that each gene in a register was distinct. These assumptions were made to simplify register designs and keep the database at a manageable size for fast computational search.

To avoid redundancy in the database, any register with superfluous parts (containing terminators, promoters, or genes that do not affect gene regulation in any state) was removed from the database if its "parent" register [the same register except without the superfluous part(s)] was also represented in the database. Moreover, all registers that transcribed either no gene or the same gene in every state were removed from the database, as this gene regulation is trivial to implement.

Figure 5:
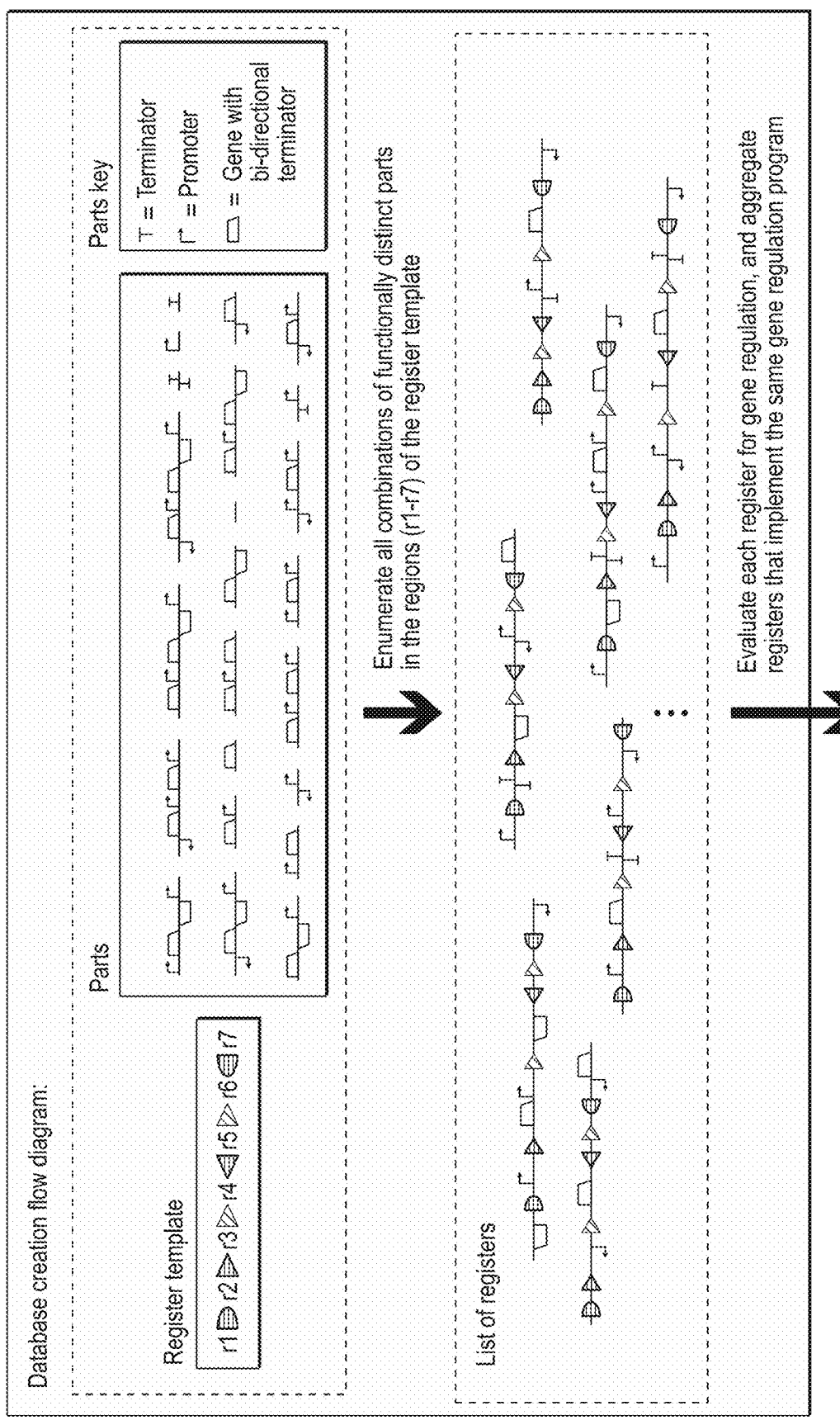
FIG. 5. The GRSM database. A flow diagram depicting how the database was created (top). The database has a pre-compiled list of GRSM registers for distinct gene regulation programs (middle). State diagrams represent gene regulation programs, with each node containing stripes of different colors corresponding to which genes are expressed in that state (no stripes implies no expression of any gene). A search function accepts a user-specified gene regulation program and returns registers from the database capable of implementing it (bottom).
Figure 5:
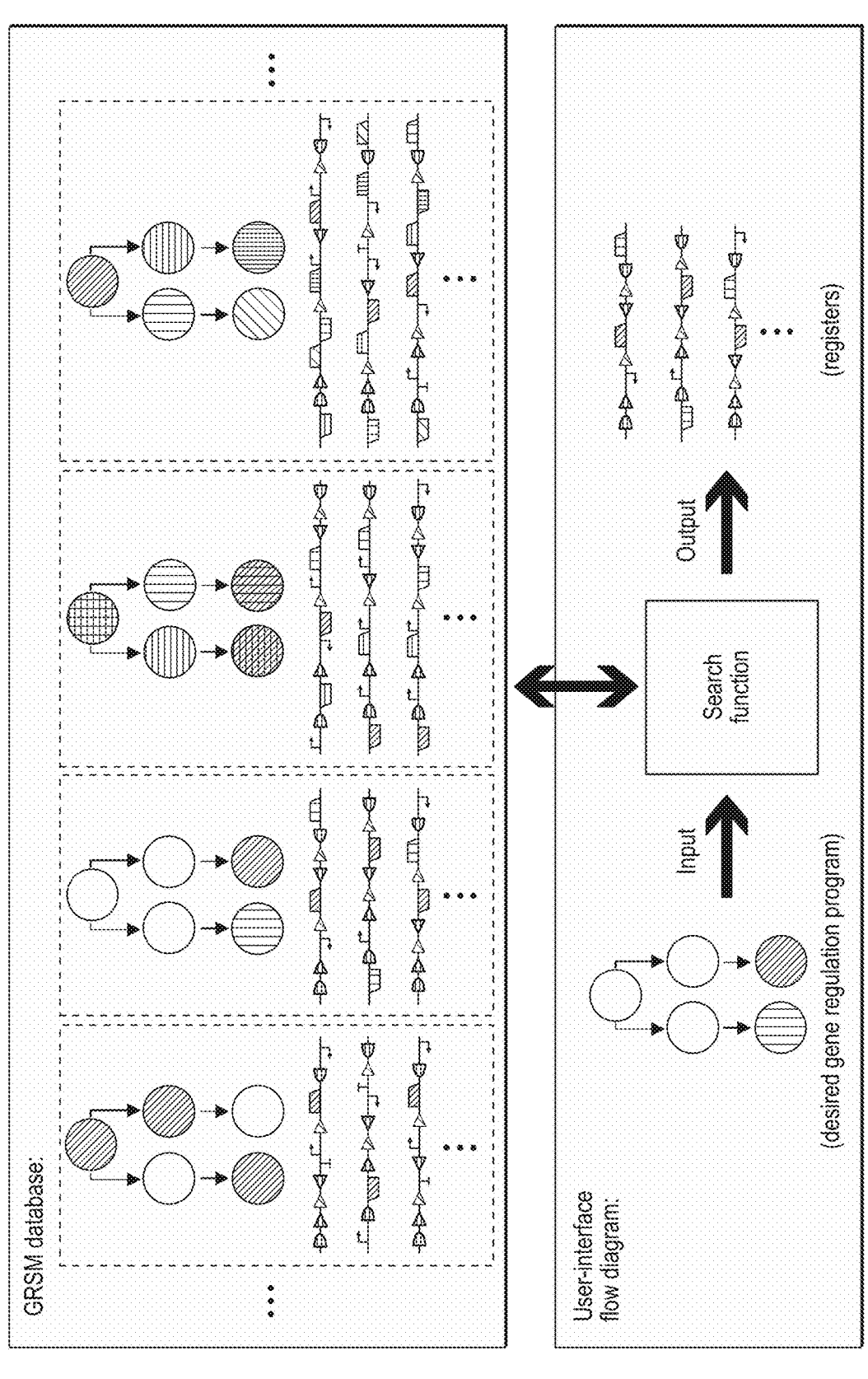

The resulting database (Example 14) contains a total of 5,192,819 GRSM registers that implement 174,264 gene regulation programs. Each register is different in the sense that no two registers have all of the same parts in all of the same positions. Registers in the database regulate transcription of anywhere from 1 to 14 genes (FIG. 14A). A register for any desired program that regulates up to 3 genes is likely to be in the database—which comprises 100% of possible 1-gene regulation programs, 95% of possible 2-gene regulation programs, and 61% of possible 3-gene regulation programs (FIG. 14B). Moreover, 27% of possible 4-gene regulation programs are represented in the database, but the percentage drops off steeply beyond that, as the number of possible gene regulation programs grows exponentially with each additional gene (Example 12). One could apply straightforward gene replacement principles to go beyond the scope of regulation programs represented in the database, for example, by replacing multiple distinct genes on a register with copies of the same gene, or replacing a gene with a multi-cistronic operon (FIG. 15). To conveniently utilize the GRSM database for design or exploration, we created a search function that accepts a user-specified gene regulation program and returns all registers from the database that may be used to implement it (FIG. 5, Example 15).

To create functional GRSMs in $E.\ coli$, we implemented the same input-output plasmid scheme as our 2-input, 5-state RSM (FIG. 3A), except we substituted in registers from our database on the output plasmid. Fluorescent protein (FP) genes were built on the registers to evaluate gene regulation performance. We grew populations of cells treated with all 5 permuted substrings of the inputs ATc and Ara, and then used flow cytometry on each population to measure the percent of cells with distinct FP expression profiles (32). We successfully implemented four single-gene regulation programs (FIG. 6A-D) and one multi-gene regulation program (in which unique subsets of three distinct FPs were expressed in each state, FIG. 6E), with at least 94% of cells from each experimental population adopting the expected FP expression profile. These GRSMs enable convenient fluorescent-based reporting on the identity and order of cellular events. For example, the GRSM from FIG. 6E allowed us to evaluate the performance of the underlying RSM with increasing input time durations (by 1 hour steps) using flow cytometry (FIGS. 16A-16E). Our findings demonstrated that input durations of 2 hours were sufficient for a majority of cells to adopt their expected state.

Because unpredictable behaviors can result when gene regulatory parts are assembled into specific arrangements, certain GRSMs may not implement gene regulation programs as expected. Indeed, this was the case when we initially tested a GRSM that was expected to express green fluorescent protein (GFP) after being exposed to the inputs Ara only or ATc→Ara (FIG. 17A) (32). Rather than debugging, we constructed two alternative GRSMs using different registers from our database (FIG. 17B-C) that performed better than the initial GRSM, one of which had at least 95% of cells with the expected gene expression profile for each experimental population (FIG. 17C). In general, many gene regulation programs represented in our database have multiple possible registers that can implement them (FIG. 18). For example, most 1-gene regulation programs have at least 373 possible registers, most 2-gene regulation programs have at least 55 possible registers, and most 3-gene regulation programs have at least 14 possible registers. Even for programs in the database that regulate up to 14 genes, most have at least 4 possible registers that can implement them. This highly degenerate design space offers a range of GRSM registers that can act as alternatives for one another in the event that a particular register fails to perform to a certain standard. Additional computationally and experimentally derived rules might enable ranking of candidate registers for their likelihood of successful gene regulation function.

Figure 7A:
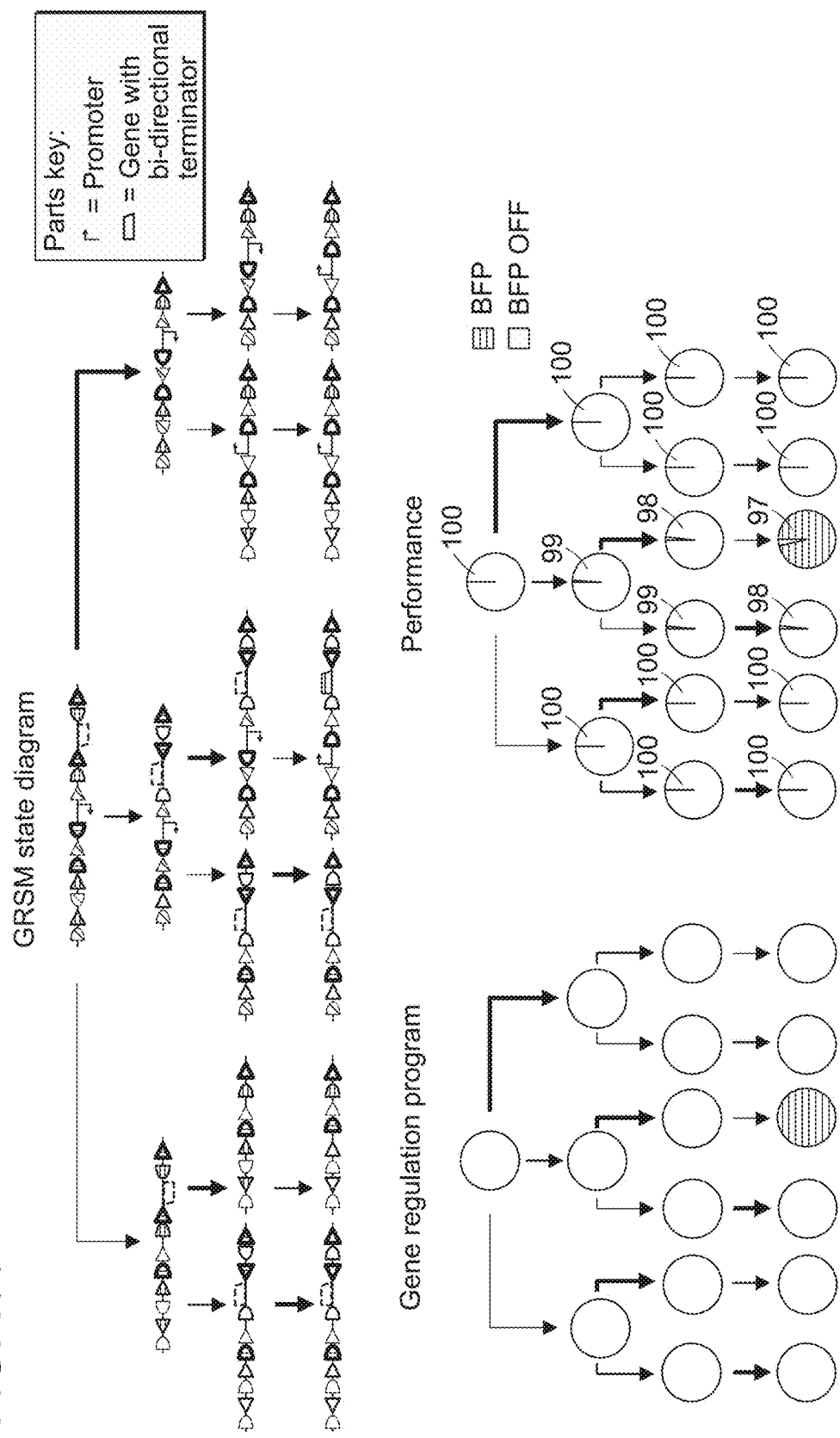
FIGS. 7A-7B. Implementing 3-input, 16-state GRSMs. We built GRSMs in E. coli to implement the gene regulation programs depicted on the bottom left of panel A and panel B, with each node containing stripes of different colors corresponding to which gene products (blue=BFP, green=GFP) are expressed in that state (no stripes implies no expression of any gene). The corresponding GRSM state diagrams are depicted on the top of each panel, with expressed (ON) fluorescent reporters represented by shaded genes and non-expressed (OFF) fluorescent reporters represented by outlined genes. In the bottom right of each panel, nodes represent populations of cells induced with all permuted substrings of the inputs ATc (orange arrow), Ara (blue arrow), and DAPG (purple arrow). Cultures were treated with saturating concentrations of each input (250 ng/mL ATc, 1% w/v Ara, or 25 µM DAPG) at 30° C. for 24 hours in three biological replicates. The nodes are shaded according to the percent of cells with or without gene expression as measured by flow cytometry. Node labels show the percent of cells with the expected gene expression profile (averaged over all three biological replicates).
Figure 7B:
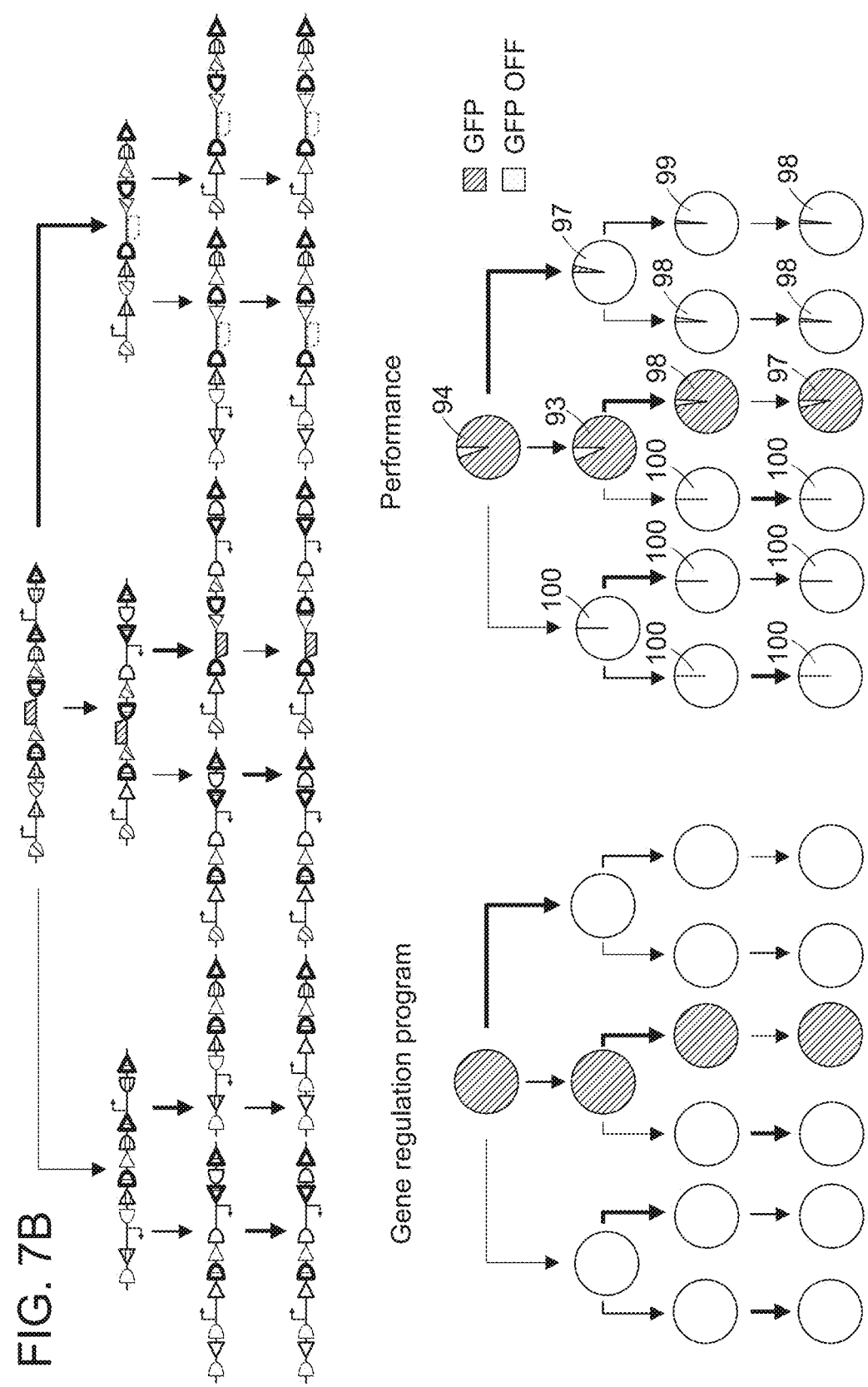

To demonstrate the scalability of GRSMs, we built two 3-input, 16-state GRSMs by interleaving genetic parts into the register from FIG. 4A. One GRSM functions as a 3-input passcode switch that only turns on the expression of a gene (blue fluorescent protein) when it receives the input Ara→DAPG→ATc (FIG. 7A). The other GRSM expresses a gene (GFP) by default and turns it off if it receives any input that is not along the Ara→DAPG→ATc trajectory (FIG. 7B). Both GRSMs were implemented in $E.\ coli$ and tested with all 16 permuted substrings of the inputs ATc, Ara, and DAPG (32). Flow cytometry revealed that at least 93% of cells from each experimental population adopted the expected gene expression profile. Thus, scalable GRSMs that function efficiently can be implemented using our design framework.

Materials and Methods (for Examples 1-4)
Strains, Media, Antibiotics, and Inducers All plasmids were implemented and tested in $E.\ coli$ strain DH5αPRO (F-Φ80lacZΔM15 Δ(lacZYA-argF)U169 deoR recA1 endA1 hsdR17(rk⁻, mk⁺) phoA supE44 thi-1 gyrA96 relA1 λ⁻, $P_{N25}$/tet$^R$, $P_{laciq}$/lacI Sp$^r$). All experiments were performed in Azure Hi-Def media (Teknova, Hollister, USA) supplemented with 0.4% glycerol. For cloning, we used E. coli strains DH5αPRO or EPI300 (F-mcrA Δ(mrr-hsdRMS-mcrBC) Φ80lacZM15 ΔlacX74 recA1 endA1 araD139 Δ(ara, leu)7697 galU galK λ⁻ rpsL (Str$^R$) nupG trfA dhfr), as indicated in the "Plasmid construction and cloning" section. All cloning was done in Luria-Bertani (LB)-Miller media (BD Difco) or Azure Hi-Def media, as indicated in the "Plasmid construction and cloning" section. LB plates were made by mixing LB with 1.5% w/v Agar (Apex). For both cloning and experiments, antibiotics were used at the following concentrations: chloramphenicol (25 μg/ml) and kanamycin (30 μg/ml). For experiments, inducers were used at the following concentrations: ATc (250 ng/ml), Ara (1% w/v), and DAPG (25 μM).

Plasmid Construction and Cloning

All plasmids were constructed using basic molecular cloning techniques and Gibson assembly (49, 50). Tables 3 and 4 give a list of relevant parts, their sequences, and the sources from which they were derived.

All input plasmids (pNR64 and pNR220) have a kanamycin resistance cassette (kanR) and a ColE1 (high copy) origin of replication. The input plasmid pNR64 was adapted from the Dual Recombinase Controller from Bonnet et al. (2013) (Addgene #44456). We replaced the chloramphenicol resistance cassette in this Dual Recombinase Controller with kanR to make pNR64. To make pNR220 we inserted the PhlF promoter system from Nielsen et al. (36) onto pNR64 to drive the expression of the A118 recombinase, gifted to us from Dr. James Thomson (USDA-ARS WRRC, Albany, Calif.). In order to control A118 tightly in the absence of any input, we expressed the phlF gene (responsible for suppressing transcription from $P_{PhlF}$) from the strong constitutive proD promoter (51). All input plasmids were transformed into chemically competent E. coli strain DH5αPRO, and subsequently isolated using the QIAEGN® QIAprep Spin Miniprep Kit and verified with Sanger sequencing (Quintara Biosciences).

All output plasmids (pNR160, pNR163, pNR164, pNR165, pNR166, pNR186, pNR187, pNR188, pNR291, pNR292, and pNR284) have a chloramphenicol resistance cassette (camR), and are built on a bacterial artificial chromosome (BAC) vector backbone to ensure low copy number, as we ideally want ~1 register per cell. The BAC we used is derived from Wild et al. (52), and is capable of being induced to a higher copy number with Copy Control (Epicentre) in EPI300 cells. Strings of attB and attP recognition sites for pNR160 and pNR188 were synthesized from Integrated DNA Technologies and cloned into their respective backbones. For the construction of all GRSM output plasmids (pNR163, pNR164, pNR165, pNR166, pNR186, pNR187, pNR291, pNR292, and pNR284), we interleaved the array of recognition sites on pNR160 (for 2-input, 5-state) and pNR188 (for 3-input, 16-state) with promoters, terminators, and genes using Gibson assembly. In order to prevent unwanted recombination on our plasmids, we avoided re-using identical part sequences on the same plasmid. For promoters, we used proD, BBa_R0051, and BBa_J54200, which have all been previously characterized to have strong expression (53). The proD promoter is an insulated promoter, which helps with consistent performance across varying contexts (51). We fused the two promoters, BBa_R0051 and BBa_J54200, upstream of 20 nt initial transcribed sequences (ATATAGTGAACAAGGAT-TAA (SEQ ID NO: 1) and ATAGGTTAAAAGCCAGACAT (SEQ ID NO: 2), respectively) characterized in Hsu et al. (54), and named the concatenated parts proNR3 and proNR4, respectively. We chose terminators for our GRSMs from among the set of validated strong and sequence diverse terminators characterized in Chen et al. (55). We often constructed terminators in tandem to increase termination efficiency. Lastly, we used the fluorescent reporter genes gfpmut3b (56), mrfp (57), and mtagbfp (58) to produce outputs. The ribosome binding site (RBS) of each gene was optimized using the Salis Lab RBS calculator (59). Upstream of each RBS, we fused a self-cleaving hammerhead ribozyme to prevent the upstream 5' untranslated transcript region from interfering with translation of the downstream gene (60). All output plasmids were transformed into chemically competent E. coli strain EPI300 or DH5αPRO, and subsequently isolated using the QIAGEN® QIAprep Spin Miniprep Kit and verified with Sanger sequencing (Quintara Biosciences).

Like the output plasmids, all plasmids to test the forward (attB-attP→attL-attR) and reverse (attL-attR→attB-attP) recombination efficiencies for each recombinase used in this study (see FIGS. 8A-8B) have a chloramphenicol resistance cassette (camR), and are built on a bacterial artificial chromosome (BAC). The forward reaction test plasmids (pNR230 for BxbI, pNR239 for A118, and pNR276 for TP901) were each constructed with a reverse-oriented gfpmut3b (attached to the same RBS and ribozyme as on the output plasmids described above) downstream of a forward-oriented proD promoter, and with anti-aligned attB and attP sites for the cognate recombinase flanking the gene. Each forward reaction test plasmid was transformed into chemically competent E. coli strain DH5αPRO, and subsequently isolated using the QIAGEN® QIAprep Spin Miniprep Kit and verified with Sanger sequencing (Quintara Biosciences). To generate the reverse reaction test plasmids (pNR279 for BxbI, pNR280 for A1 18, and pNR287 for TP901), we transformed each forward reaction test plasmid into chemically competent E. coli strain DH5αPRO containing the pNR220 input plasmid, induced the cognate recombinase for each test plasmid, and isolated the recombined plasmid from cells using the QIAGEN® QIAprep Spin Miniprep Kit. Each reverse reaction test plasmid was then transformed into chemically competent E. coli strain DH5αPRO, and subsequently isolated again using the QIAGEN® QIAprep Spin Miniprep Kit and verified with Sanger sequencing (Quintara Biosciences). The second transformation and isolation step for these test plasmids was done to separate them from the pNR220 plasmid, which inevitably was present in the purified DNA solution after the first isolation step.

RSM Implementation

All RSMs were implemented with a two-plasmid system (an input plasmid and an output plasmid). Table 4 shows each RSM and the names of the input and output plasmids used to implement them. All 2-input RSMs used the pNR64 input plasmid with various output plasmids depending on the desired gene regulation program. All 3-input RSMs used the pNR220 input plasmid with various output plasmids depending on the desired gene regulation program.

For the 2-input, 5-state RSMs, the input plasmid (pNR64) and the output plasmid were simultaneously transformed into chemically competent E. coli DH5αPRO cells. Post-transformation, the cells were plated on LB plates with chloramphenicol and kanamycin. Colonies from these plates were used to initiate RSM testing experiments (see following "testing" sections).

For the 3-input, 16-state RSMs, we first transformed the input plasmid (pNR220) into chemically competent E. coli DH5αPRO cells and plated the transformants onto LB plates with kanamycin. Subsequently, we inoculated a colony in Azure Hi-Def media (with kanamycin) and grew it overnight at 37° C., then diluted it 1:2000 into fresh media (same media as the overnight) and let it re-grow at 37° C. to an OD600 of 0.2-0.5. The cells from this culture were then made chemically competent and transformed with the output plasmid. The purpose for the sequential transformation in this case was to allow time for the phlF gene (on the input plasmid) to be expressed at a high enough level to suppress expression of the A118 recombinase from the $P_{PhlF}$ promoter (also on the input plasmid). This was to ensure minimal recombinase levels when the output plasmid was introduced into the system; otherwise the register on the output plasmid could have falsely recorded a chemical induction event prior to its actual occurrence. Post-transformation of the output plasmid, the cells were plated on an LB plate with chloramphenicol and kanamycin. Colonies from these plates were used to initiate RSM testing experiments (see following "testing" sections).

Experiment for Testing the 2-Input, 5-State RSM from FIG. 3A

To test the 2-input, 5-state RSM for one biological replicate, a colony of E. coli cells containing input plasmid pNR64 and output plasmid pNR160 was inoculated into media with kanamycin and chloramphenicol, grown overnight (~18 hours) at 37° C., and subjected to two rounds of induction followed by a round of outgrowth. For the first round of induction, the overnight culture was diluted 1:250 into each media with no inducer, media with ATc, and media with Ara, and grown at 30° C. for 18 hours. For the second round of induction, these 3 cultures were then diluted again 1:250 into fresh media: the non-induced culture was diluted into media with no inducer again, the ATc induced culture was diluted into each media with no inducer and media with Ara, and the Ara induced culture was diluted into each media with no inducer and media with ATc. These cultures were again grown at 30° C. for 18 hours. The resulting cultures represented 5 populations of cells treated with all 5 permuted substrings of the inputs ATc and Ara. Lastly, for the outgrowth, these cultures were diluted 1:250 into media with no inducer and grown at 37° C. for ~18 hours. The purpose of this final outgrowth was to allow all cell populations to normalize to conditions without inducer, such that detected differences between populations could be attributed to their history of inputs rather than their current environment. This experiment was repeated with a different starting colony for each biological replicate. All cultures were grown in 250 μL media (in 96-well plates) shaken at 900 rpm. All media contained chloramphenicol and kanamycin. Final populations from the experiment were analyzed with sequencing assays and qPCR assays (see below).

Sequencing Assay for Testing the 2-Input, 5-State RSM from FIG. 3A

For the sequencing assay, each of the 5 experimental populations from the previous section (from each of 3 biological replicates) were diluted 1:10$^6$, plated (100 μl) onto LB plates with chloramphenicol and kanamycin, and grown overnight at 37° C. such that each resulting colony represented the clonal population of a single cell from each experimental population. The register region on the output plasmid for around 24 (at least 22) colonies from each plate (experimental population) was amplified with colony PCR and sent for Sanger sequencing (Quintara Biosciences). Chromatograms from the sequencing reactions were aligned to the expected register sequence to determine whether or not they matched. Results from all 3 replicates were totaled, and the percent of cells matching their expected sequence is displayed in FIG. 3B.

Quantitative-PCR Assay for Testing the 2-Input, 5-State RSM from FIG. 3A

For the qPCR assay, plasmids from each of the 5 experimental populations from the previous section (from each of 3 biological replicates) were isolated with the QIAprep Spin Miniprep Kit and used as template in qPCR reactions. All qPCR reactions were performed on the Roche LightCycler 96 Real-Time System using KAPA SYBR® FAST Master Mix and according to the Kapa Biosystems recommended protocol (200 nM each primer, 10 μl 2× master mix, and no more than 20 ng template in a 20 μl reaction). Each template was qPCR amplified with each of 3 primer pairs ("pp1", "pp2", and "pp3") elucidated by PSIT (see "PCR-based State Interrogation Tool" section for a description and Example 16 for the program), as well as a normalizing primer pair ("ppN") that amplified the backbone of the output plasmid. FIG. 19 shows the regions on the register to which the 3 PSIT primer pairs bind and the register states which they are supposed to amplify. Table 5 gives the primer sequences. Along with the experimental templates, we also ran qPCR reactions of each primer pair with control template made up entirely of output plasmid containing register state "S3" (see FIG. 19) that would get amplified by each primer pair. We isolated this output plasmid from our Ara-treated E. coli population and sequence verified it to make sure that the register state matched S3. We calculated the "fractional amount" of output plasmid amplified by each primer pair (pp1, pp2, or pp3) for each experimental template ("t1", "t2", "t3", "t4", or "t5") as:

$$f_{tx,ppy}=2^{(C_{q_{tx,ppn}}-C_{q_{tc,ppn}})-(C_{q_{tx,ppy}}-C_{q_{tc,ppy}})}$$

where tx is the experimental template of interest (t1, t2, t3, t4, or t5), ppy is the primer pair of interest (pp1, pp2, or pp3), tc is the control template (output plasmid in S3), ppn is the normalizing primer pair (ppN), and Cq is the Cq value from the qPCR reaction of the template and primer pair indicated in its subscript.

From these $f_{tx,ppy}$ values, we created a qPCR result vector for each experimental template, $f_{tx}$:

$$f_{tx}=[f_{tx,pp1},f_{tx,pp2},f_{tx,pp3}]$$

This result vector was compared to the theoretical result vector that we would get if the template were made up entirely of a register from one particular state in our RSM, $f_{ts}$:

$$f_{ts}=[f_{ts,pp1},f_{ts,pp2},f_{ts,pp3}]$$

where ts is the template made entirely of register from one state (S1, S2, S3, S4, or S5). The $f_{ts,ppy}$ values are 0 or 1 depending on whether or not the particular primer pair ppy amplifies that state (FIG. 19). The similarity of $f_{tx}$ to $f_{ts}$ was quantified by Euclidean distance, $D_{tx,ts}$:

$$D_{tx,ts}|f_{tx}-f_{ts}|=\sqrt{(f_{tx,pp1}-f_{ts,pp1})^2+(f_{tx,pp2}-f_{ts,pp2})^2+(f_{tx,pp3}-f_{ts,pp3})^2}$$

The Euclidean distances between the qPCR result vectors of each experimentally derived template and the theoretical qPCR result vectors of each state are displayed in a heatmap in FIG. 11 for each of 3 biological replicates.

Experiment for Testing the 3-Input, 16-State RSM from FIG. 4A

To test the 3-input, 16-state RSM for one biological replicate, a colony of E. coli cells containing input plasmid pNR220 and output plasmid pNR188 was inoculated into media with kanamycin and chloramphenicol, grown overnight (~18 hours) at 37° C., and subjected to three rounds of induction followed by a round of outgrowth. For the first round of induction, the overnight culture was diluted 1:250 into each media with no inducer, media with ATc, media with Ara, and media with DAPG, and grown at 30° C. for 24 hours. For the second round of induction, these 4 cultures were then diluted again 1:250 into fresh media: the non-induced culture was diluted into media with no inducer; the ATc-induced culture was diluted into each media with no inducer, media with Ara, and media with DAPG; the Ara-induced culture was diluted into each media with no inducer, media with ATc, and media with DAPG; and the DAPG-induced culture was diluted into each media with no inducer, media with ATc, and media with Ara. These cultures were again grown at 30° C. for 24 hours. For the third round of induction, each of these 10 cultures were diluted again 1:250 into fresh media: the non-induced→non-induced culture was diluted into media with no inducer; the ATc→non-induced culture was diluted into media with no inducer; the ATc→Ara culture was diluted into each media with no inducer and media with DAPG; the ATc→DAPG culture was diluted into each media with no inducer and media with Ara; the Ara→non-induced culture was diluted into media with no inducer; the Ara→ATc culture was diluted into each media with no inducer and media with DAPG; the Ara→DAPG culture was diluted into each media with no inducer and media with ATc; the DAPG→non-induced culture was diluted into media with no inducer; the DAPG→ATc culture was diluted into each media with no inducer and media with Ara; and the DAPG→Ara culture was diluted into each media with no inducer and media with ATc. These cultures were again grown at 30° C. for 24 hours. The resulting cultures represented 16 populations of cells treated with all 16 permuted substrings of the inputs ATc, Ara, and DAPG. Lastly, for the outgrowth, these cultures were diluted 1:250 into media with no inducer and grown at 37° C. for 18 hours. This experiment was repeated with a different starting colony for each biological replicate. All cultures were grown in 250 μL media (in 96-well plates) shaken at 900 rpm. All media contained chloramphenicol and kanamycin. Final populations from the experiment were analyzed with sequencing assays and qPCR assays (see below).

Sequencing Assay for Testing the 3-Input, 16-State RSM from FIG. 4A

For the sequencing assay, each of the 16 experimental populations from the previous section (from each of 3 biological replicates) were diluted 1:10$^6$, plated (100 μl) onto LB plates with chloramphenicol and kanamycin, and grown overnight at 37° C. such that each resulting colony represented the clonal population of a single cell from each experimental population. The register region on the output plasmid for 5-6 colonies from each plate (experimental population) was amplified with colony PCR and sent for Sanger sequencing (Quintara Biosciences). Chromatograms from the sequencing reactions were aligned to the expected register sequence to determine whether or not they matched. Results from all 3 biological replicates were totaled, and the percent of cells matching their expected sequence is displayed in FIG. 4B.

Quantitative-PCR Assay for Testing the 3-Input, 16-State RSM from FIG. 4A

For the qPCR assay, plasmids from each of the 16 experimental populations from the previous section (from each of 3 biological replicates) were isolated with the QIAGEN® QIAprep Spin Miniprep Kit and used as template in qPCR reactions. As with the 2-input, 5-state RSM testing, all qPCR reactions were performed on the Roche LightCycler 96 Real-Time System using KAPA SYBR® FAST Master Mix and according to the Kapa Biosystems recommended protocol (200 nM each primer, 10 μl 2× master mix, and no more than 20 ng template in a 20 μl reaction). Each template was qPCR amplified with each of 6 primer pairs ("pp1", "pp2", "pp3", "pp4", "pp5", and "pp6") elucidated by PSIT as well as a normalizing primer pair ("ppN") that amplified the backbone of the output plasmid. FIG. 20 shows the regions on the register to which the 6 PSIT primer pairs bind and the register states which they are supposed to amplify. Table 6 gives the actual primer sequences. Similar to the 2-input, 5-state system, we also ran qPCR reactions of each primer pair with control template made up entirely of output plasmid containing a register that would get amplified by each primer pair. Unlike with the 2-input, 5-state RSM, however, there was no single register state that would get amplified by each primer pair. So we ended up using an output plasmid in state "S2" as a control template for pp1, pp4, and pp5 and an output plasmid in state "S8" as a control template for pp2, pp3, and pp6 (FIG. 20). The plasmid with register state S2 was isolated from our ATc-treated E. coli population (and sequence verified), and the plasmid with register state S8 was isolated from our Ara→DAPG treated E. coli population (and sequence verified). We proceeded with calculating the fractional amount of plasmid amplified by each primer pair for each experimental template, and then comparing the data for each template to each theoretical state (with Euclidean distance) the same way as we did for the 2-input, 5-state RSM, except generalized to 6 primer pairs and 16 states. In other words:

$$f_{tx} = [f_{tx,pp1}, f_{tx,pp2}, \ldots, f_{tx,pp6}]$$

$$f_{ts} = [f_{ts,pp1}, f_{ts,pp2}, \ldots, f_{ts,pp6}]$$

$$D_{tx,ts} = |f_{tx} - f_{ts}| = \sqrt{(f_{tx,pp1} - f_{ts,pp1})^2 + \ldots + (f_{tx,pp6} - f_{ts,pp6})^2}$$

The Euclidean distances between the qPCR result vectors of each experimentally derived template and the theoretical qPCR result vectors of each state are displayed in a heatmap in FIG. 13 for each of 3 biological replicates.

Designing the GRSM Registers from FIG. 6 and FIGS. 17A-17C

We inputted our desired gene regulation programs into the database search function [coded in MATLAB R2013b (Mathworks, Natick, USA); Example 15], and received an output list of registers, from which we chose our candidates for implementation. Table 7 shows the MATLAB search function input matrix we used to specify our desired gene regulation programs, as well as the search function output vectors that we chose as our registers to implement the gene regulation programs, as per the instructions on how to use the search function (Example 15).

Experiment for Testing the GRSMs from FIG. 6 and FIGS. 17A-17C

The experiments to test the 2-input, 5-state GRSMs followed the same format as the experiment to test the 2-input, 5-state RSM from FIG. 3A, except we used 24 hour inductions instead of 18 hour inductions for the induction rounds, and instead of analyzing the experimental populations with sequencing and qPCR assays, we used a fluorescence assay (see "Fluorescence assay" section).

Experiment for Testing the GRSMs from FIG. 7

The experiments to test the 3-input, 16-state GRSMs followed the same format as the experiment to test the 3-input, 16-state RSM from FIG. 4A, except instead of analyzing the experimental populations with sequencing and qPCR assays, we used a fluorescence assay (see "Fluorescence assay" section).

Figure 8A:
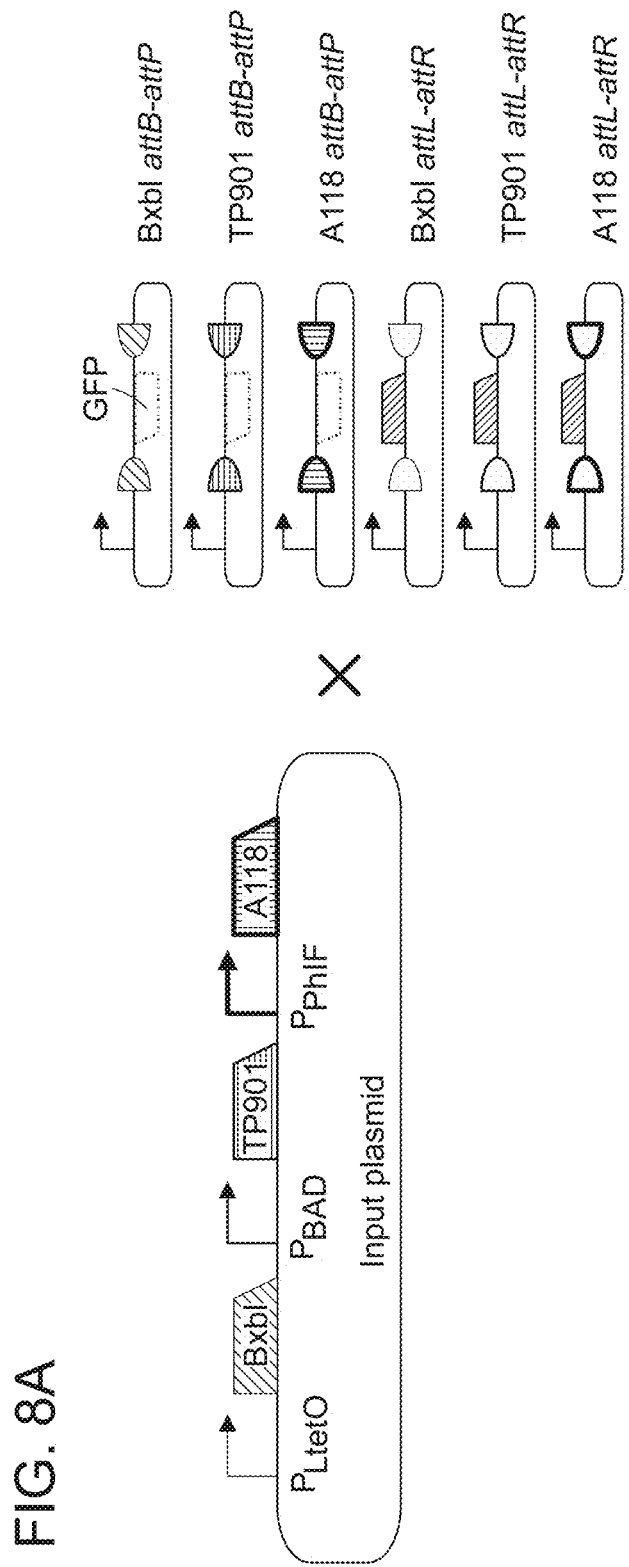
FIGS. 8A-8B. Forward and reverse recombination activity for BxbI, TP901, and A118. (A) The experimental setup in E. coli. Cells containing inducible recombinase systems on the input plasmid were transformed with plasmids containing attB-attP (with no GFP expression) or attL-attR (with GFP expression) for each of the 3 recombinases (BxbI, TP901, and A118) used in this study. (B) Fluorescence distributions of the cells after being incubated at 30° C. for 16 hours with and without recombinase induction. Induced cultures were treated with saturating amounts of inducer (250 ng/mL ATc for BxbI, 1% w/v Ara for TP901, or 25 µM DAPG for A118). Three biological replicates are shown.
Figure 8B:
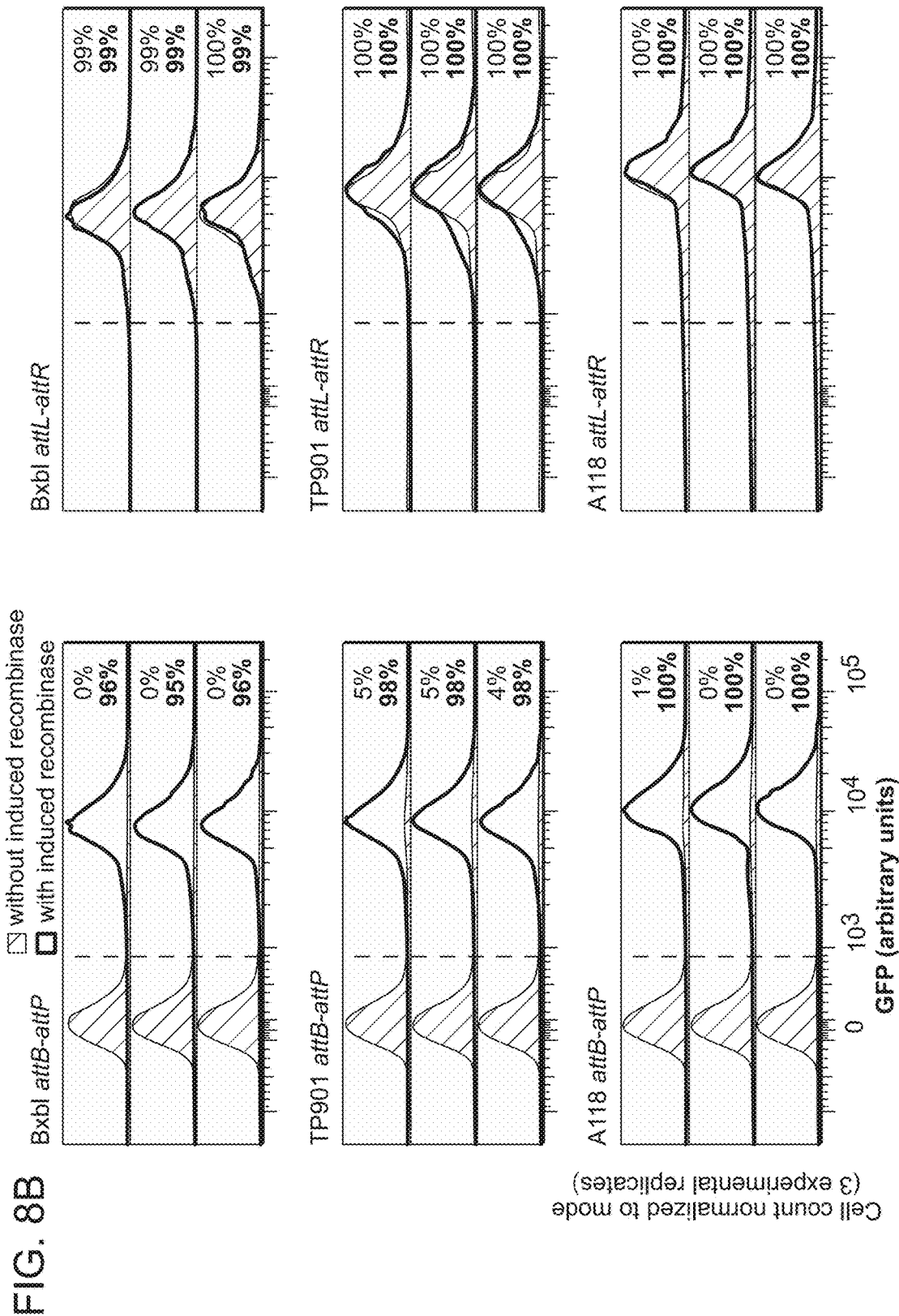

Testing the Reversibility of BxbI, TP901, and A118 in FIGS. 8A-8B

For each recombinase in our study (BxbI, TP901, and A118), we isolated two plasmids that were recombined versions of each other: one with attB-attP and no GFP expression (pNR230 for BxbI, pNR239 for A1 18, and pNR276 for TP901), and the other with attL-attR and GFP expression (pNR279 for BxbI, pNR280 for A118, and pNR287 for TP901). We transformed each of these plasmids into chemically competent $E.$ $coli$ DH5αPRO containing the input plasmid pNR220 (prepared as described in the "RSM implementation" section). To measure recombination for each transformant, a colony was inoculated into media with kanamycin and chloramphenicol, grown overnight (~18 hours) at 37° C., and subject to a round of induction followed by a round of outgrowth. For the induction, the overnight culture was diluted 1:250 into each media with no inducer and media with inducer (ATc for BxbI, Ara for TP901, or DAPG for A118), and grown at 30° C. for 16 hours. For the outgrowth, these cultures were diluted 1:250 into media with no inducer and grown at 37° C. for 18 hours. This experiment was repeated with a different starting colony for each of 3 biological replicates. All cultures were grown in 250 μL media (in 96-well plates) shaken at 900 rpm. We measured the percentage of cells from each population expressing GFP as described in the "Fluorescence assay" section.

RSM Time Course Experiment in FIGS. 16A-16E

For one biological replicate, a colony of $E.$ $coli$ DH5αPRO cells containing input plasmid pNR64 and output plasmid pNR291 was inoculated into media with kanamycin and chloramphenicol, grown overnight (~18 hours) at 37° C., re-diluted 1:75 into fresh media, split into 11 cultures, and grown at 30° C. When cells reached an OD600 of 0.1, we re-diluted cells from one culture 1:125 into fresh media and let them outgrow at 37° C. This (uninduced) population would become the 0 hour timepoint in FIG. 16C-E. All other cultures were subject to induction prior to outgrowth. Ara was directly added to 5 of the cultures, and ATc was directly added to the other 5 and they were allowed to continue growing at 30° C. Each of the 5 cultures for each input would become induction timepoints separated by 1-hour steps (for each input); we refer to them as input seed cultures. After 1 hour, we diluted cells from one ATc seed culture 1:125 into fresh media and let them outgrow at 37° C. This would become the 1-hour timepoint for ATc in FIG. 16C. From the same seed culture, we also diluted cells 1:25 into media with Ara and let them grow for the equivalent amount of input exposure time (1 hour) at 30° C. prior to diluting 1:125 into fresh media and letting them outgrow at 37° C. This would become the 1-hour timepoint for ATc→Ara in FIG. 16E. Then, for the same seed culture, we directly added Ara and let the cells grow for the equivalent amount of input exposure time (1 hour) at 30° C. prior to diluting 1:125 into fresh media and letting them outgrow at 37° C. This would become the 1-hour timepoint for ATc→Ara in FIG. 16D. The same procedure was done for an Ara seed culture after 1 hour, except with ATc as the sequentially added input. This process was subsequently repeated at 2 hours with different ATc and Ara seed cultures, and so on for 3, 4, and 5 hours. The outgrowth for all cell populations continued for 16 hours after the final cells were diluted for outgrowth (10 hours after the initial induction began). This experiment was repeated for 3 biological replicates. All cultures were grown in 250 μL media (in 96-well plates) shaken at 900 rpm. All media contained chloramphenicol and kanamycin. Final populations from the experiment were analyzed with flow cytometry (see "Fluorescence assay" section).

Fluorescence Assay

For all experiments with a fluorescence assay, we diluted cells 1:125 into phosphate buffered solution (PBS, Research Products International) and ran them on a BD-FACS LSR-Fortessa-HTS cell analyzer (BD Biosciences, CA). We measured 30,000 cells for each sample and consistently gated by forward scatter and side scatter for all cells in an experiment. GFP (product of gfpmut3b) intensity was measured on the FITC channel (488 nm excitation laser, 530/30 detection filter), RFP (product of mrfp) intensity was measured on the PE-Texas Red channel (561 nm excitation laser, 610/20 detection filter), and BFP (product of mtagbfp) intensity was measured on the PacBlue channel (405 nm excitation laser, 450/50 detection filter). A fluorescence threshold was applied in each channel to determine the percent of cells with expressed (ON) versus not expressed (OFF) fluorescent proteins. The threshold was based on a negative control ($E.$ $coli$ DH5αPRO containing pNR64 and a BAC with no fluorescent reporter genes) population, such that 0.1% of these negative control cells were considered to have ON fluorescent protein expression in each channel (corresponding to a 0.1% false positive rate).

All fluorescence-based experiments had 3 biological replicates. For the recombinase reversibility experiment (FIG. S1) and RSM time-course experiment (FIGS. 16A-16E), the data for all 3 replicates is shown. For the GRSM experiments (FIG. 6, FIG. 7, and FIG. 17A-17C), the data from all 3 replicates is averaged. For these experiments, the largest standard error for the percent of any fluorescent subpopulation was 1.22%.

GRSM Database and Search Function

The GRSM database was constructed (as discussed in the main text) using MATLAB R2013b (Mathworks, Natick, USA), partly run on the Odyssey cluster supported by the FAS Division of Science, Research Computing Group at Harvard University.

The database contains 3 arrays: registerArray—an array of GRSM registers, grpArray—an array of gene regulation programs, and register2grp—an array that maps each register in registerArray to its corresponding gene regulation program in grpArray (by index).

Each gene regulation program in grpArray is represented by a 70-element vector of "0"s and "1" s. Each contiguous stretch of 14 elements belongs to a state—S1, S2, S3, S4, and S5, respectively—corresponding to the states in FIG. 3A. And within each state, each element (1 to 14) represents a gene ("G1" to "G14", respectively). For example, given a vector in grpArray, element 1 represents G1 in S1, element 15 represents G1 in S2, element 29 represent G1 in S3, element 43 represent G1 in S4, element 57 represents G1 in S5, element 2 represents G2 in S1, element 16 represents G2 in S2, and so on. The binary value of each element indicates whether that gene in that particular state is OFF ("0") or ON ("1"). If the value of any given gene in every state in a gene regulation program is 0, then that gene does not exist in the regulation program.

Each register in registerArray is represented by a 7-element vector of numbers "1" through "25". Each element of the vector corresponds to a DNA region ("a" to "g") interleaving the recognition sites of the register shown in FIG. 3A. The value of each element (1 to 25) represents a part, as defined in Table 8. Each part is made up of genes, terminators, and constitutive promoters, arranged such that each part is functionally distinct (see Example 11). Non-palindromic parts (as indicated in Table 8) can appear inverted on the register, in which case they take on a negative value. For example, part "1" is a gene, which is a non-palindromic part. If it appears as a "1" on an element of a register vector, then it is facing left to right (5' to 3'), and if it appears as a "−1" on an element of a register vector, then it is facing right to left (5' to 3').

It is important to note that all explicitly depicted terminators in the parts (Table 8) are unidirectional, thus transcription can move through them in the reverse direction. However, the unidirectional terminator in part "3" can be replaced by a bi-directional terminator without changing the function of the part. This is because placing an additional terminator upstream of the promoter in part "3" would only terminate transcription that would subsequently be re-initiated in the same direction. Also the unidirectional nature of part "7" is not always necessary to the gene regulation program of the underlying register. That is, sometimes part "7" (a unidirectional terminator by itself) can be replaced by part "4" (a bidirectional terminator by itself) without affecting the gene regulation implemented by the underlying register. To make this distinction clear to database users, we parsed all occurrences of part "7" in the registerArray and replaced it with a special identifier, part "15", if its unidirectional nature is not important to the gene regulation program of the underlying register. Therefore, all occurrences of part "7" in registerArray now represent parts that necessitate "terminator read-through" (transcription through their unidirectional terminators in the reverse direction) for the gene regulation program of the underlying register. Likewise, because convergent (face-to-face) promoters can destructively interfere with each other (61), we made a special distinction for parts with promoters that necessitate "promoter read-through" (transcription through their promoters in the reverse direction, Table 8). Because part "10" (a promoter by itself), depending on its register context, can sometimes necessitate read-through and sometimes not, we parsed all occurrences of part "10" in the registerArray and replaced it with a special identifier, part "14", if it does not necessitate read-through for the gene regulation program of the underlying register. Therefore, all occurrences of part "10" in registerArray now represent parts that necessitate promoter read-through for the proper gene regulation program of the underlying register.

All parts with genes in registerArray also have bidirectional terminators on the 3' ends of those genes. These terminators are not explicitly depicted in Table 8. Although the database has otherwise been reduced to avoid superfluous terminators, promoters, and genes, the implicit terminators on the 3' ends of genes may sometimes be superfluous. That is, they may not be necessary for the proper gene regulation program of the underlying register.

Lastly, the array register2grp has the same number of elements as registerArray. It maps each register in registerArray to a value that is the index of its corresponding gene regulation program in grpArray.

We present the database as a MATLAB MAT-file (Additional Database S1), where each array is stored in a MATLAB variable. The search function for this MAT-file database was also created in MATLAB R2013b and requires MATLAB software to run. Code for the MATLAB search function and more information on how it works is included in Example 15.

PCR-Based State Interrogation Tool (PSIT)

The PSIT Algorithm uses an Abstract Data Type—the class DNARegister—to represent registers. In order to determine what sets of primer pairs may be used to uniquely detect an inputted DNARegister and all of its recombined states, the algorithm: (1) "recombines" the input register, generating DNARegister instances for all states that result from any permuted substring of inputs, (2) generates a list of primer pairs made up of all possible primers that bind to each region between recognition sites and on the terminal ends of the recognition site arrays, (3) narrows the list to primer pairs that only amplify in any given state when they are on adjacent regions, and (4) determines all subsets of this final list of primer pairs that can be used to uniquely identify each possible state of the DNA register. This final list of primer pair subsets is then returned as output along with details regarding which primer pairs amplify in which states. For qPCR compatibility purposes, step 3 ensures that every amplicon is short and that every primer pair always yields the same amplicon when it amplifies (regardless of state). The PSIT program was implemented in Python 2.7. Code for the PSIT program and more information on how it works is included in Example 16.

Example 5. Mathematical Discussion of RSMs

If an RSM is designed such that each input-driven recombinase only has one attB-attP pair on the register, the number of states cannot exceed $2^N$. To prove this, we first introduce the concept of "irreducibility". An irreducible string of recombinases is one in which, when the recombinases are applied to a register in the given order, each recombinase performs an operation (excision or inversion) on the register. We can make the following two statements about irreducible sequences:

Statement 1: Every possible state of a register must be accessible by the application of some irreducible string of recombinases. This follows from considering (1) that each state is the result of a string of recombination operations, and (2) that the string of recombinases corresponding to that string of recombination operations is irreducible by definition.

Statement 2: Assuming a register with one pair of attB-attP per recombinase, all irreducible strings from the same subset of recombinases generate the same state on the register. This follows from considering that (1) all 'rearrangeable' DNA segments on the register are flanked on both sides by attB and/or attP sites belonging to the subset of recombinases being applied, (2) by the definition of irreducibility, each recombinase in the irreducible string will catalyze recombination between its attB-attP pair, and (3) when recombination between attB and attP sites occur, they always form the same junctions—the back end of the attB will join the front end of the attP, and the front end of the attB will join the back end of the attP. Therefore all 'rearrangeable' DNA segments will form the same junctions after an irreducible string of recombinases is applied, regardless of the order in which those recombinases are applied.

Given a RSM with N input-driven recombinases and one pair of attB-attP per recombinase on its register, all states must be accessible by some irreducible string of recombinases (Statement 1), and all irreducible strings from the same subset of the N recombinases must generate the same state (Statement 2). Therefore, there cannot be more states than there are subsets of recombinases, which is $2^N$ (see Example 7 for a more detailed version of this proof).

More generally, this proof can be expanded to show that given k pairs of orthogonal attB-attP pairs per recombinase on a register, the number of states it can access will never exceed $2^{kN}$ (see Example 8). For large serine recombinases, there is a limit of k=6 orthogonal and directional attB-attP pairs for a given recombinase (31). Therefore, the information capacity of RSMs using large serine recombinases is intrinsically bound exponentially.

Example 6. Testing the Reversibility of Recombination Reactions for the Recombinases Used in this Study—BxbI, TP901, and A118

We tested the reversibility of recombinases used in our study (BxbI, A118, and TP901) by measuring the amount of turnover from attL-attR to attB-attP, and vice versa, over 16 hours of recombinase induction. Specifically, for testing each recombinase, we used two plasmids that were recombined versions of each other: one with attB-attP and no GFP expression, and the other with attL-attR and GFP expression. These plasmids were each transformed into E. coli with inducible recombinases (FIG. S1A). Turnover from attB-attP to attL-attR was evaluated by the number of cells that switched from not expressing GFP to expressing GFP after induction, and conversely, turnover from attL-attR to attB-attP was evaluated by the number of cells that switched from expressing GFP to not expressing GFP after induction. Results are shown in FIG. S1B. Whereas we observed >95% conversion of attB-attP to attL-attR for all recombinases, we did not observe any conversion of attL-attR to attB-attP for TP901 and A118, and <1% for BxbI. This data corroborates the irreversibility of the recombinase systems used in our study.

Example 7. Proof that, with N Recombinases, One can Only Generate at Most $2^N$ Distinct DNA States with Recombinase-Based State Machines if Limited to One Recognition Site Pair Per Recombinase Theorem:

If we have N recombinases and only one pair of recognition sites per recombinase, then given any initial DNA string (sequence) on a register, at most $2^N$ distinct DNA strings can be generated on that register by applying different recombinase strings.

Before proving this theorem, let us be clear about the assumptions of the recombinase system:

Assumption 1: We assume that the recombination reactions that occur are unidirectional. This means that once a recombinase is applied, it cannot be applied again with re-directionality factors, nor can another recombinase in the set of N be used to reverse its recombination reaction.

Assumption 2: We assume that all recognition sites are polar (have a back end and a front end) and that recombination between two recognition sites occurs by pasting (5' to 3') the back end of one recognition site with the front end of the other recognition site (and vice versa). This assumption is consistent with attB-attP recombination in large serine recombinase systems.

Assumption 3: We assume that if DNA gets excised from the register, then it is lost and no longer interacts with the register.

Assumption 4: We assume that the recombinases are specific. That is, they can only cause recombination between their cognate recognition sites.

Assumptions 1 and 2 permit the application of this theorem to large-serine recombinase based systems.

Assumption 3 is motivated by the fact that excised DNA will not replicate and will therefore be lost after multiple rounds of cell division. This assumption precludes situations where the excised DNA fragment contains an origin of replication or situations in which recombinases are applied in quick enough succession that the excised fragment has a chance to re-integrate into the register before it is lost due to cell division.

Proof of Theorem:

We assume that within a pair of recognition sites of a recombinase, one recognition site is capable of recombining with the other. For example, if using large-serine recombinases, this would mean that each recognition site pair would be composed of an attB site and an attP site. We also assume that our initial DNA string on the register has a recognition site pair for each recombinase (2N recognition sites total). These assumptions do not affect the generality our theorem, since any lesser number of active (capable of recombining) recognition sites could only further limit the number of distinct DNA strings we can generate on the register.

We represent our initial DNA string on the register as a string of 2N+1 distinct symbols (representing DNA sequences), where each symbol junction represents a recombinase recognition site, like so:

ABCDEFGHI

We define the start and end of the register as the first and last symbol of the initial string (highlighted in bold), A and I here.

The symbols here are alphabetical letters. We will assume that the DNA sequences they represent are all unique and not symmetric (with regard to their reverse complement). This assumption can only increase the number of distinct DNA strings on the register that can be generated from an initial DNA string and therefore does not affect the generality of our theorem.

To visually help us keep track of recognition site type (designating which recombinase it belongs to) and polarity, we interleave the symbols in our DNA string with asymmetric parentheses to represent the type (shape of parenthesis) and polarity (direction of parenthesis) of recognition site contained within the symbol junction, like so.

A(B[C{D<E)F]G}H>I

Note that the parentheses are not actually part of the DNA string- they are just visual markers. For example the [ between B and C and the] between F and G just let us know that those two junctions (BC and FG) are recognition sites that belong to the same recombinase and that they have opposite polarity.

We refer to the recombinase of a given recognition site by writing "r" followed by the parentheses-type of its recognition sites. So, for example r[ would be the recombinase that recombines the recognition sites represented by the [ parentheses.

If a DNA string does not contain any recognition sites for a recombinase, then when that recombinase is applied, the DNA string is unchanged.

If a DNA string contains only one recognition site for a recombinase, then when that recombinase is applied, the DNA string is also unchanged.

If a DNA string contains both recognition sites for a recombinase, then when that recombinase is applied, it cuts each recognition site at the junction between their two symbols and pastes together (5' to 3') the symbol on the back end of one recognition site with the symbol on front end of the other, and vice versa. This means that if two recognition sites are facing opposite directions, then the DNA string in between them gets inverted when they recombine. And if two recognition sites are facing the same direction, then the DNA string in between them gets excised when they recombine.

For example, if we apply r[ to the register with the DNA string:
A[B]C
the DNA in between the recognition sites gets inverted to produce the string
AB*C
where B* denotes inversion (reverse complement).

As another example, if we apply r[ to the register with the DNA string:
A[B[C
the DNA in between the recognition sites circularizes (the right end of B pastes to the left end of B) and gets excised from the register, leaving the string
AC Because the recombination reactions are unidirectional, the new symbol junctions that are formed no longer represent active (capable of recombining) recognition sites (and so we do not visually mark them with parentheses).

A recombinase string is an ordered list of recombinases, where each recombinase appears at most once. We are allowed to apply any recombinase string, like so (reading left to right):
r(r[r<
When applied to the register with the initial DNA string:
A(B[C{D<E)F]G}H>I
this recombinase string would produce the successive DNA strings on the register:
AE*>D*}C*]B*F]G}H>I
AE*>D*}C*G}H>I
AE*I We now introduce a crucial definition: given a recombinase string, we call the recombinase string "irreducible" if every recombinase in that string performs a recombination event (either excision or inversion of a DNA substring) on the register when applied. Thus, in the above example, r(r[r< was irreducible. On the other hand, for example, the recombinase string r(r<r{ is not irreducible because r{ does nothing to the register when it is applied.

Then here is the key observation for proving the theorem:
Uniqueness Lemma:
Every irreducible string involving all N recombinases leads to the same outcome on the register.
Proof of Uniqueness Lemma:
Let S be a recombinase string of length N, and suppose S is irreducible. Then as we apply the recombinases in S to our initial DNA string Y, it can never happen that an active recognition site that belongs to any recombinase in the string S besides the one currently being applied gets deleted. For suppose that a r[ recognition site got deleted when we applied r{, where r[ and r{ are any two recombinases in S. Then we can conclude, firstly, that r[ was not yet applied (it would have recombined the r[ recognition sites if it had been), and secondly, that there is no longer any point in applying r[—it will have no effect, since at most one r[ recognition site remains in the DNA string. But this means that any continuation of the current string that is irreducible must omit r[, and therefore it has length less than N, which cannot be.

Thus, every recombinase in S must do one of two things when applied: it must either invert (reverse complement) the substring between the two appropriate recognition sites, or it must perform a "benign deletion"—i.e., excising out the substring between the two appropriate recognition sites, without having any effect on any other active pairs of recognition sites belonging to a recombinase from S.

Now, given two symbols, A and B, we will call A the "left soulmate" of B, if A and B satisfy the following property: after we apply some irreducible string of length N to Y, A must occur immediately followed by B (or B* must occur immediately followed by A *) either on the register or on an excised DNA string. In general, we will call A and B "soulmates" if either A is the left soulmate of B or B is the left soulmate of A. Also, given a symbol C, we will call C a "singular soulmate" if after we apply some irreducible string of length N to Y, C occurs by itself on an excised DNA string.
Soulmate Claim:
If [A and]B both occur in Y, then A* is the left soulmate of B; if A[ and B] both occur in Y, then A is the left soulmate of B*; if A] and ]B both occur in Y, then A is the left soulmate of B; if ]A and B] both occur in Y, then B is the left soulmate of A; and if ]A] occurs in Y, then A is a singular soulmate.
Proof of Claim:
If we apply an irreducible recombinase string of length N to Y, eventually r] must be applied. And since the recombinase string is irreducible, the r] recognition sites must still be present when it happens. The fact that recombination adjoins (5' to 3') the symbol on the back end of one recognition site to the symbol on the front end of the other recognition site (and vice versa) guarantees that when recombination occurs: if [A and ]B both occur in Y, then an A*B (or B*A) junction will form; if A] and B] both occur in Y, then an AB* (or BA*) junction will form; if A] and ]B both occur in Y, then an AB (or B*A*) junction will form; if [A and B] both occur in Y, then a BA (or A*B*) junction will form; and if ]A] occurs in Y, then there will form a junction between the right side of A and the left side of A. Once these symbols are brought together as described, then no other active recognition site is (or will ever be) in between them, so nothing further can happen that will ever separate them. This completes the claim.

By the rules of the soulmate claim, we can figure out how the symbols in an initial DNA string will interconnect after applying an irreducible recombinase string of length N (given that one exists).

For example, given an initial DNA string, Y, for which there is at least one irreducible recombinase string of length N, like
A(B[C{D]E(F}G,
with N pairs of recognition sites and 2N+1 symbols, we can construct a "soulmate graph" as follows. The graph has 4N+2 vertices, corresponding to the left and right sides of each of the symbols (A, B, C, D, E, F, and G in this case). We connect the left and right side of each symbol by an edge. We also draw an edge from the left of each symbol to the right of its left soulmate (following the rules of the soulmate claim), keeping in mind that inversion switches left and right (e.g. the left of A and the right of A* are the same).

To illustrate, with the Y above, the soulmate graph would consist of the following simple path:
Left of A---Right of A---Left of F---Right of F---Right of C---Left of C---Left of E---Right of E---Left of B---Right of B---Right of D---Left of D---Left of G---Right of G Reading off the graph, we can predict that after any irreducible string of 3 recombinases is applied to Y, the result must be:
AFC*EBD*E
And indeed this prediction is borne out by the (in this case) unique irreducible string r{r(r[.

To take another example, if
Y=A(B[C)D]E
then the soulmate graph consists of the path
Left of A---Right of A---Right of C---Left of C---Left of E---Right of E
along with the cycle
Left of B---Left of D---Right of D---Right of B---Left of B
The cycle represents DNA that circularizes and excises off of the register, leaving only A C* E on the register. Indeed this is what happens when we apply either the r[r(string or the r(r[ string.

To complete the proof of the Uniqueness Lemma: notice that the rules of the soulmate claim will always find one soulmate for each symbol on the edge of the initial DNA string. Each edge symbol can only form one junction by virtue of its position; therefore, after applying an irreducible string of length N to an initial DNA string, each edge symbol only forms a junction with its soulmate. Also, the rules of the soulmate claim will always find two soulmates for each symbol that is not on the edge of the DNA string and that does not circularize with itself (e.g. ]A]). No symbol can have more than two junctions (one on each side), therefore these symbols, after applying an irreducible string of length N to an initial DNA string, only form junctions with their soulmates. It follows that the final DNA string on a register (made up of the edge symbols of the initial DNA string and whatever symbols are left in between) after applying an irreducible string of N recombinases is completely determined by the rules of the soulmate claim, which have no dependence on the ordering of the N recombinases. This completes the proof of the Uniqueness Lemma.

The Uniqueness Lemma easily implies the following corollary.

Corollary:

For every subset of k recombinases, every irreducible string involving all k of those recombinases leads to the same DNA string on the register.

Proof of Corollary:

We can just consider a shorter DNA string of 2k+1 symbols, obtained from the original string by concatenating together all pairs of symbols whose junctions are not recognition sites for any of the k relevant recombinases. For example, if we only cared about r(and r[, then
A(B[C{D<E)F]G}H>I
would become
A (B[CDE)F]GHI
where CDE and GHI are each now a single symbol. We then apply the Uniqueness Lemma to the shorter DNA string. This completes the proof of the corollary.

But the corollary means that, if X is any DNA string on the register obtained by applying some recombinase string to our initial DNA string Y, then we can specify X using only N bits, by simply listing a set Z of recombinases that should be applied to Y in an irreducible string. For clearly X can be obtained from Y by some irreducible string. And crucially, we do not need to list the order in which to apply the recombinases in the set Z—since by the corollary, the order is irrelevant to this final outcome. This completes the proof of the theorem.

Therefore at most $2^N$ distinct DNA strings can be generated on the register. QED.

For a more general analysis on the upper limits of RSMs without the one recognition site pair per recombinase constraint, see Example 8.

Example 8. Analysis on the Upper Limits of RSMs

If we consider RSMs that use no more than k orthogonal pairs of recognition sites per recombinase, then no more than $2^{kN}$ states are achievable, as per the following observation and proof:

Observation:

Suppose we are allowed N recombinases, but only k pairs of orthogonal recognition sites per recombinase (in the case of large-serine recombinases, k=6). Then given any initial DNA string Y on a register, we can produce at most $2^{kN}$ distinct strings on that register by applying different recombinase strings. This observation uses the same assumptions about the recombinase system as the theorem in Example 7.

Proof of the Observation:

Certainly the number of distinct DNA strings that we can produce on the register, in this case, is no greater than the number we could produce if we allowed ourselves an even greater freedom—namely, to treat all the kN different pairs of recognition sites that occur in our DNA string as if they each belonged to different recombinases. But we already proved, in Example 7, that in that case the number of distinct strings that can be generated on the register is upper-bounded by $2^{kN}$. QED.

Example 9. Deriving the Number of Permuted Substrings of N Inputs

If there are N total inputs at our disposal, we can take any subset of h inputs. For a given h, there are N choose h such subsets, and for each subset there are h! permutations, so there are $$\binom{N}{h} \cdot h! = \frac{N!}{(N-h)!}$$

permuted substrings of length h.

Next, because we can take substrings of any length, h, up to N, this gives us the following total number of permuted substrings:

$$\sum_{h=0}^{N} \frac{N!}{(N-h)!} = N! \sum_{h=0}^{N} \frac{1}{(N-h)!} = N! \sum_{p=0}^{N} \frac{1}{p!}$$

The summation term in this formula can be approximated by the natural exponential function e. So the formula for the total number of permuted substrings of N inputs can be approximated by eN!.

Example 10. Implementing RSMs that Encode a Distinct State for Every Permuted Substring of Inputs Up to N=7 Inputs Given a RSM with N inputs, each driving the expression of single recombinase, we have designed registers that encode a distinct state for every permuted substring of inputs up to N=7 inputs (Table S2). The first two registers (for N=1 and N=2) were designed trivially. For N>2 we used a modular construction strategy.

Modular Construction Strategy:

First, we define the "unit module" which is a recognition site array composed of 2 attB-attP pairs for different recombinases arranged as follows:

([)[ where parentheses of different shapes represent recognition sites of different recombinases. The direction of each parenthesis represents the polarity of the recognition site.

We say that the "(" recognition sites occupy position 1 of the unit module and that the "[" recognition sites occupy position 2.

The unit module will encode (enter a distinct state) for whether or not the recombinase with recognition sites in position 2 was applied, and, given whether or not the recombinase with recognition sites in position 1 was applied, it will encode for which recombinase was applied first.

It follows that we can create registers that encode for every possible permuted substring of N inputs (each driving expression of a recombinase) by concatenating together a unit module for every pairwise combination of recombinases and abiding by the following 2 rules:

1. Every unit module must be orthogonal.
2. At least one recognition site pair for each recombinase must appear in position 2 of a unit module.

Because this construction strategy requires that every recombinase be paired with N−1 other recombinases in a unit module and that each unit module be orthogonal, it follows that the strategy requires N−1 orthogonal recognition site pairs per recombinase. However we can only create up to 6 pairs of orthogonal attB-attP pairs per large serine recombinase, and therefore this construction strategy only enables registers that encode a distinct state for every permuted substring of inputs up to N=7 inputs. Beyond N=7, we adopt a different register design strategy that can access approximately $3.9^N$ states (Example 13).

Example 11. Discussion of Parts Used to Build the GRSM Database

The parts in the database are made up of constitutive promoters, terminators, and genes. All genes are assumed to have bi-directional terminators on their 3' ends. Table 8 shows all of the parts and their part IDs (an integer number) that we use to refer to them. Non-palindromic parts (as indicated in FIG. 23) can appear inverted, in which case they take on the corresponding negative value for their part ID. For example, we refer to the part composed of only a gene as part "1" when it is facing left to right (5' to 3') on a register as depicted in FIG. 23 or part "−1" when it is facing right to left (5' to 3') on a register. Below we show that the parts we used to build the database are the set of all possible functionally distinct parts.

Each part, when placed on a region of a register, performs a combination of the following four activities:

1. Providing a constitutively transcribed gene (using a self-contained promoter-gene module, e.g., part "19")
2. Providing a gene for transcription from a region on the left (e.g., part "1"), a region on right (e.g., part "−1"), or from both a region on the left and a region on the right (e.g., part "8").
3. Preventing transcription from moving to the left (e.g. part "−7"), moving to the right (e.g., part "7"), or moving both to the left and right (e.g. part "4").
4. Initiating transcription to the left (e.g. part "−10"), to the right (e.g., part "10"), or to both the left and right (e.g. part "6").

We define the function of a part by the combination of these four activities that it performs. For example, the function of part "2" is to provide a gene for transcription from the left, prevent transcription from moving to the left (recall that genes have 3' bi-directional terminators), and initiate transcription to the right. For a more complicated example, the function of part "24" is to transcribe a gene constitutively, provide a gene for transcription from both the left and right, prevent transcription from moving to the left, and initiate transcription to the right. Table 8 gives the function of all 37 parts (including the inversion of non-palindromic parts) that we used to build the database (this does not include "14", "−14", "15", and "−15"—see "GRSM database and search function" subsection of the Materials and Methods). One can observe from Table 8 that all parts are functionally distinct.

To show that these parts also comprise all possible functions, we first note that the 4 activities that define function are not mutually exclusive. For example, a part cannot initiate transcription to the left and prevent transcription from moving to the left. As another example, a part that does not initiate transcription to the left and provides a gene for transcription from the right, must necessarily prevent transcription from moving to the left (again, since genes are paired with bi-directional terminators on their 3' ends). We can summarize the mutual dependence of the four activities with two rules: (rule #1) a part cannot initiate transcription to and prevent transcription from moving to the same direction, and (rule #2) a part that provides a gene (constitutive or not) and does not initiate transcription in a particular direction must necessarily also prevent transcription from moving to that particular direction.

So to find the number of possible distinct functions, we can start by finding the total number of activity combinations. To do this we consider that, including the absence of activity, there are 2 possibilities for activity #1, 4 possibilities for activity #2, 4 possibilities for activity #3, and 4 possibilities for activity #4, so the total number of activity combinations is 2*4*4*4=128.

We apply rule #1 above to remove 56 non-permissible activity combinations. Then from the remaining pool we apply rule #2 above to remove 35 non-permissible activity combinations. This leaves us with 37 possible, distinct functions (activity combinations), which is the same as the number of functionally distinct parts we used to build the database. Therefore, the parts that we used to build the database represent all possible functionally distinct parts that we could build from constitutive promoters, terminators, and genes (with bi-directional 3' terminators).

Example 12. Number of Possible 5-State Gene Regulation Programs as a Function of Number of Regulated Genes, r First, we consider that there are 5 states, and any particular gene can be expressed or not expressed in each of those states. So in total there are $Z=2^5=32$ different regulation programs for a single gene. Next, we consider that there are r genes in our gene regulation programs. Each gene can have any of the Z=32 single-gene regulation programs. So the calculation of number of possible gene regulation programs for r genes, G(r), simplifies to choosing r combinations of Z possible regulation programs (with repetition, since multiple genes can have the same regulation program):

$$G(r) = \binom{Z+r-1}{r}$$

This function grows exponentially.

Even though there are Z=32 different regulation programs for a single gene, one of them is a program in which the gene is not expressed in any state, and another one of them is a program in which the gene is expressed in every state. These regulation programs are trivial and so we do not consider them in our GRSM database. So we used Z=30 when calculating the data for FIG. 14B.

Example 13. Implementing RSMs that can Achieve ~3.9N States for N Inputs

We define the sequence of recognition sites that, when put on a register, enable a RSM to access a distinct state for every permuted substring of N inputs as "N-permutable subsequences". In Table S2, we show N-permutable subsequences up to N=7. In Example 10, we explain that our design strategy does not permit N-permutable subsequences beyond N=7.

However, given N>7 inputs, we can divide our inputs into as many mutually exclusive sets of 7 as possible (floor(N/7)). Then we can create a 7-permutable subsequences for each of these mutually exclusive sets and concatenate them together on a register. Lastly we can take the remainder inputs (N mod 7) that did not fit into any of the mutually exclusive sets of 7, create a (N mod 7)-permutable subsequence for this set, and concatenate it to the rest of the subsequences on the register. For example, we can build a register for N=17 inputs that has two 7-permutable subsequences and one 3-permutable subsequence.

As derived in Example 9, the exact equation for the number of permuted substrings of N inputs, m(N), is:

$$m(N) = N! \sum_{p=0}^{N} \frac{1}{p!}$$

In the example above with N=17 inputs, the register would theoretically be able to access m(7)·m(7)·m(3)~3·10$^9$ distinct states. In general, the construction strategy for N>7 described above would enable the following number of states, f(N):

$$f(N) = m(7)^{\text{floor}(\frac{N}{7})} \cdot m(N \bmod 7)$$

We approximate this function as $$f(N) \sim m(7)^{\frac{N}{7}} \sim 3.9^N$$

Example 14. Database

A MAT-file that contains the GRSM database. In the MAT-file, the three database arrays are each stored as separate MATLAB variables: registerArray, grpArray, and register2grp. registerArray is a matrix where each row is a register, and grpArray is a matrix where each column is a gene regulation program. See the "The GRSM database and search function" subsection of the "Material and Methods" for a detailed explanation of these arrays, and how registers and gene regulations programs are represented within them. The array register2grp maps each register in registerArray to the index of its corresponding gene regulation program in grpArray, such that the register in row i of registerArray corresponds to the gene regulation program in column register2grp(i) of grpArray, ie. grpArray(:, register2grp(i)). We provide a search function for accessing the GRSM database in Example 15.

Example 15. Instructions on Using the GRSM Database Search Function

The search function is written in MATLAB R2013b and requires MATLAB software to run. Description. This function takes a desired gene regulation program, searches the GRSM database contained in Additional Database S1 for registers that implement that gene regulation program, and then outputs those registers.

Instructions on Using the Function.
1. Copy the "searchGRSM" script below into a text file and save it as "searchGRSM.m"
2. Copy the "registerRank" script below into a text file and save it as "registerRank.m" in the same directory as "searchGRSM.m"
3. Download the MAT-file (Additional Database S1). Ensure that the name of the file is "grsmDB.mat". If it is not, then rename it to "grsmDB.mat". Then move it to the same directory as the files above.
4. Open MATLAB and navigate the working directory to the directory of the files above.
5. Type "registers=searchGRSM(grp)" into the MATLAB command to use the function, where grp is your desired gene regulation program and registers is the variable to which the output will be stored.

Instructions on Creating the Input
Specify your grp (gene regulation program) as a 5×M matrix. Each row (row 1 to row 5) represents a state S1 to S5 (respectively) corresponding to FIG. 3A. Each column represents a gene. You can specify anywhere up to M=14 genes. Each element of the matrix should be a "0" or "1" corresponding to whether or not you want that gene to be OFF (0) or ON (1) in that state.

Interpreting the Output
The output registers is a N×7 matrix. Each row of the matrix represents a register that can be used to implement grp. Each column (column 1 to column 7) of the register represents a DNA region "a" to "g" (respectively) corresponding to FIG. 3A.

Each element of the matrix specifies a part for that register in that DNA region.

Parts are numbers "1" through "25" (with some also appearing as negative) as defined in Table S9. A more in depth explanation of the parts can be found in "The GRSM database and search function" subsection of the "Material and Methods" as well as in Supplementary Text S6.

The output registers are ordered (ranked) with the following 4 steps:
1. rank by the (least to greatest) number of parts necessitating promoter read-through
2. subrank by the (least to greatest) number of parts necessitating terminator read-through 3. subrank by the (greatest to least) number of empty parts (part "5") 4. subrank by the (least to greatest) number of promoters Example grp = [00001; 00010; 00100; 01000; 10000]

```
              -1   5   8    2    2   5  -14
              -1   5   5    8   -3  -9    1
              -1   3   5   -9    8   5    1
              -1   9   5   -3    8   5    1
              14   9   5    1    8   5    1
               9   3   5    1    8   5    1
              -1   5   8    1    9   5  -14
              -1   5   8    1   14   5   -9
              -1   5   5    8   -9  -3    1
              -1  -7   8    2   14   5   -9
              14  -1  10   -1  -12   5    1
registers =   -1  -7 -12    2    5   5   -9
              -1   7   5    8   -3  -9   -9
              -1   3   5   -9    8  -7   -9
              -1   9   5   -3    8  -7   -9
               9   3   5   -9    8  -7    1
               9   9   5   -3    8  -7    1
              -1  -7 -12    1    9   5  -14
              -1  -7 -12    1   14   5   -9
              -1   7   5    8   -9  -3   -9
               5  -7  12    5    8  -7   -9
               9  -7   5   -9    8  -7   -9
               9   7   5    8   -9   7   -9
```

For more examples, Table S8 shows the inputs and outputs from the search function used to implement the 2-input, 5-state GRSMs in this study.

Example 16. Instructions on Using PSIT

PSIT is a program written in Python 2.7.
Description.
SIT returns all possible sets of primer pairs that uniquely identify each state of an inputted DNA register, and also returns information about these states. In order to do this, one must call the outputFiles function of the DNARegister class. outputFiles takes a parameter name, a string of the name to associate with the returned files, and a parameter elucidatePP, a Boolean value denoting whether or not the user wants primer pair sets outputted, or simply information about the states.
Instructions
First the user must construct an instance of the DNARegister class by passing in a numpy array of 4-element arrays, where each 4-element array provides information about a recombinase recognition site. Let $r_i$ be one such 4-element array, then $r_i=[a_i, b_i, c_i, d_i]$, where:
   $a_i$ corresponds to the recombinase cognate for that site.
      $1<=a_i<=N$ where N is the number of recombinases/inputs.
   $b_i$ provides information about what orthogonal pair of recognition sites this particular recognition site corresponds to.
      $0<=b_i<=m-1$ where m is the number of orthogonal sites for the recombinase supplied by $a_i$. If $b_i \neq b_k$, then the ith and kth sites belong to different pairs of recognition sites, and are therefore orthogonal.
   $c_i$ tells whether the recognition site is attP, attB, attL, or attR.
      $c_i=0 \rightarrow$ attP
      $c_i=1 \rightarrow$ attB
      $c_i=2 \rightarrow$ attL
      $c_i=3 \rightarrow$ attR
   $d_i$ provides the polarity of the recognition site.
      $d_i=1 \rightarrow$ "forward"
      $d_i=-1 \rightarrow$ "reverse"
Thus, to construct a DNARegister with six recognition sites, the user will use the following form, where $r_i=[a_i, b_i, c_i, d_i]$ as discussed above.
   x=numpy.array($r_1, r_2, r_3, r_4, r_5, r_6$)
   registerX=DNARegister(x)
Below we provide a test case for the construction of a DNARegister, and the subsequent use of the outputFiles function to elucidate sets of primer pairs that uniquely identify each state of the inputted DNA register. We use the 2-input, 5-state register of FIG. 3A for this test case.
   x=numpy.array([[1,0,0,1], [1,1,0,1], [2,0,0,1], [1,1,1,-1], [2,0,1,1], [1,0,1,-1]])
   fiveStateRegister=DNARegister(x)
   fiveStateRegister.outputFiles('5state', True)
To use PSIT, one must simply copy the included script (below), and save as an executable Python program (.py extension). One must have numpy installed. Both Python and the numpy package are freely available under open-source licenses.
Once you have PSIT saved as a .py file, you may add your use cases to the bottom of the file, as is done with the included example (see the bottom of the script below). Then, you may execute the script, either running it directly through your program editor or through Terminal. The outputted files will be saved to the same directory as your script.
Interpreting the Output
If one calls outputFiles in the following way: DNARegister.outputFiles('name', False) one file will be outputted, name_info.csv.
If one calls outputFiles in the following way: DNARegister.outputFiles('name', True) three files will be outputted, name_info.csv, name_matrix.csv, name_primers.csv.
The "_info.csv" file provides information about all unique DNA states that result from all permuted substrings of the appropriate inputs to the initial DNARegister. Specifically, the regions between recombinase recognition sites are assigned an integer value. The region at the start of the register (before the first recognition site) is assigned integer "0", and the polarity of all other regions are specified relative to that region, with positive integers denoting "forward" polarity and negative integers denoting "reverse" polarity. The DNA states are assigned labels s0, s1, ... and the permuted substrings of inputs that result in a given state are also indicated.
The "_primers.csv" file provides primer pairs that may be used to uniquely identify each state of a given DNAregister. Valid primer pair subsets for qPCR can be found by choosing any one primer pair from each column of a given row. Primers are represented by integer values corresponding to the DNA regions that they bind (from "_info.csv"). Positive integers correspond to binding in the forward direction while negative integers correspond to binding in the reverse direction.
The "_matrix.csv" gives a matrix for each subset of primer pairs (in the same order as the primer pair subsets appear in "_primers.csv") that indicates which primer pairs amplify which states. Each column of a matrix represents a state (s0, s1, . . . , from the "_info.csv" file). Each row represents a primer pair, with the first row corresponding to a primer pair chosen from the first column of the "_primers.csv" file, the second row corresponding to a primer pair chosen from the second column of the "primers.csv" file, and so on. Each entry of a matrix is either a "0" where a primer pair does not amplify a state or a "1" where a primer pair does amplify a state.

TABLE 1

Information about the sequenced registers that were not in the expected state from FIG. 3B and FIG. 4B.

| Experiment | Instances | Condition | Expected state | Observed state |
|---|---|---|---|---|
| FIG. 3B | 1 | ATc | S2 | S4 |
| FIG. 3B | 2 | ATc→Ara | S4 | S5 |

TABLE 1-continued

Information about the sequenced registers that were not in the expected state from FIG. 3B and FIG. 4B.

| Experiment | Instances | Condition | Expected state | Observed state |
|---|---|---|---|---|
| FIG. 3B | 2 | Ara→ATc | S5 | S4 |
| FIG. 4B | 1 | Ara | S3 | undefined* |
| FIG. 4B | 1 | ATc→DAPG | S6 | undefined** |
| FIG. 4B | 1 | ATc→Ara→DAPG | S11 | undefined* |
| FIG. 4B | 1 | ATc→Ara→DAPG | S11 | S13 |
| FIG. 4B | 1 | DAPG→ATc→Ara | S15 | S16 |
| FIG. 4B | 1 | ATc→Ara | S5 | undefined* |

*There was recombination between TP901 attB and attP sites with mismatched dinucleotides. The recombination appeared to take place along a homologous 3-nucleotide region directly adjacent to the central nucleotide.
**One pair of TP901 attB-attP recombined when it was not supposed to.

TABLE 2

Relevant input plasmid parts and their sequences.

| Part name | Type | Notes | Sequence | Derived from | SEQ ID NO |
|---|---|---|---|---|---|
| bxbI | gene | recombinase | GTGAGAGCCCTGGTAGTCATCCGCCT GTCCCGCGTCACCGATGCTACGACTTC ACCGGAGCGTCAGCTGGAGTCTTGCC AGCAGCTCTGCGCCCAGCGCGGCTGG GACGTCGTCGGGGTAGCGGAGGATCT GGACGTCTCCGGGGCGGTCGATCCGT TCGACCGGAAGCGCAGACCGAACCTG GCCCGGTGGCTAGCGTTCGAGGAGCA ACCGTTTGACGTGATCGTGGCGTACC GGGTAGATCGGTTGACCCGATCGATC CGGCATCTTCAGCAGCTGGTCCACTG GGCCGAGGACCACAAGAAGCTGGTCG TCTCCGCGACCGAAGCGCACTTCGAT ACGACGACGCCGTTTGCGGCGGTCGT CATCGCGCTTATGGGAACGGTGGCGC AGATGGAATTAGAAGCGATCAAAGAG CGGAACCGTTCGGCTGCGCATTTCAA TATCCGCGCCGGGAAATACCGAGGAT CCCTGCCGCCGTGGGGATACCTGCCT ACGCGCGTGGACGGGGAGTGGCGGCT GGTGCCGGACCCTGTGCAGCGAGAGC GCATCCTCGAGGTGTATCACCGCGTC GTCGACAACCACGAGCCGCTGCATCT GGTGGCCCACGACCTGAACCGGCGTG GTGTCCTGTCGCCGAAGGACTACTTC GCGCAGCTGCAAGGCCGCGAGCCGCA GGGCCGGGAGTGGTCGGCTACCGCGC TGAAGCGATCGATGATCTCCGAGGCG ATGCTCGGGTACGCGACTCTGAACGG TAAGACCGTCCGAGACGACGACGGAG CCCCGCTGGTGCGGGCTGAGCCGATC CTGACCCGTGAGCAGCTGGAGGCGCT GCGCGCCGAGCTCGTGAAGACCTCCC GGGCGAAGCCCGCGGTGTCTACCCCG TCGCTGCTGCTGCGGGTGTTGTTCTGC GCGGTGTGCGGGGAGCCCGCGTACAA GTTCGCCGGGGAGGACGTAAGCACC CGCGCTACCGCTGCCGCTCGATGGGG TTCCCGAAGCACTGCGGGAACGGCAC GGTGGCGATGGCCGAGTGGGACGCGT TCTGCGAGGAGCAGGTACTGGATCTG CTCGGGGACGCGGAGCGTCTGGAGAA AGTCTGGGTAGCGGGCTCGGACTCCG CGGTCGAACTCGCGGAGGTGAACGCG GAGCTGGTGGACCTGACGTCGCTGAT CGGCTCCCCGGCCTACCGGGCGGGCT CTCCGCAGCGAGAAGCACTGGATGCC CGTATTGCGGCGCTGGCCGCGCGGCA AGAGGAGCTGGAGGGCCTGGAGGCTC GCCCGTCTGGCTGGGAGTGGCGCGAG ACCGGGCAGCGGTTCGGGGACTGGTG | (22) | 3 |

TABLE 2-continued

Relevant input plasmid parts and their sequences.

| Part name | Type | Notes | Sequence | Derived from | SEQ ID NO |
|---|---|---|---|---|---|
| | | | GCGGGAGCAGGACACCGCGGCAAAG AACACCTGGCTTCGGTCGATGAACGT TCGGCTGACGTTCGACGTCCGCGGCG GGCTGACTCGCACGATCGACTTCGGG GATCTTCAGGAGTACGAGCAGCATCT CAGGCTCGGCAGCGTGGTCGAACGGC TACACACCGGGATGTCGTAA | | |
| tp901 | gene | recombinase | ATGAAACATCATCACCATCACCACCA GGCCGGCACTAAGAAAGTAGCAATCT ATACACGAGTATCCACTACTAACCAA GCAGAGGAAGGCTTCTCAATTGATGA GCAAATTGACCGTTTAACAAAATATG CTGAAGCAATGGGGTGGCAAGTATCT GATACTTATACTGATGCTGGTTTTTCA GGGGCCAAACTTGAACGCCCAGCAAT GCAAAGATTAATCAACGATATCGAGA ATAAAGCTTTTGATACAGTTCTTGTAT ATAAGCTAGACCGCCTTTCACGTAGT GTAAGAGATACTCTTTATCTTGTTAAG GATGTGTTCACAAAAAATAAAATAGA CTTTATCTCGCTTAATGAAAGTATTGA TACTTCTTCTGCTATGGGTAGCTTGTT TCTCACTATTCTTTCTGCAATTAATGA GTTTGAAAGAGAGAATATAAAAGAAC GCATGACTATGGGTAAACTAGGGCGA GCGAAATCTGGTAAGTCTATGATGTG GACTAAGACAGCTTTTGGGTATTACC ACAACAGAAAGACAGGTATATTAGAA ATTGTTCCTTTACAAGCTACAATAGTT GAACAAATATTCACTGATTATTTATCA GGAATATCACTTACAAAATTAAGAGA TAAACTCAATGAATCTGGACACATCG GTAAAGATATACCGTGGTCTTATCGT ACCCTAAGACAAACACTTGATAATCC AGTTTACTGTGGTTATATCAAATTTAA GGACAGCCTATTTGAAGGTATGCACA AACCAATTATCCCTTATGAGACTTATT TAAAAGTTCAAAAAGAGCTAGAAGAA AGACAACAGCAGACTTATGAAAGAAA TAACAACCCTAGACCTTTCCAAGCTA AATATATGCTGTCAGGGATGGCAAGG TGCGGTTACTGTGGAGCACCTTTAAA AATTGTTCTTGGCCACAAAAGAAAAG ATGGAAGCCGCACTATGAAATATCAC TGTGCAAATAGATTTCCTCGAAAAAC AAAAGGAATTACAGTATATAATGACA ATAAAAAGTGTGATTCAGGAACTTAT GATTTAAGTAATTTAGAAAATACTGTT ATTGACAACCTGATTGGATTTCAAGA AAATAATGACTCCTTATTGAAAATTAT CAATGGCAACAACCAACCTATTCTTG ATACTTCGTCATTTAAAAAGCAAATTT CACAGATCGATAAAAAAATACAAAAG AACTCTGATTTGTACCTAAATGATTTT ATCACTATGGATGAGTTGAAAGATCG TACTGATTCCCTTCAGGCTGAGAAAA AGCTGCTTAAAGCTAAGATTAGCGAA AATAAATTTAATGACTCTACTGATGTT TTTGAGTTAGTTAAAACTCAGTTGGGC TCAATTCCGATTAATGAACTATCATAT GATAATAAAAGAAAATCGTCAACAA CCTTGTATCAAAGGTTGATGTTACTGC TGATAATGTAGATATCATATTTAAATT CCAACTCGCTACCGGTGCTGCTAAGG ACGAAAACTACGCTCTGGCTGCTTAA | (22) | 4 |
| a118 | gene | recombinase | ATGAAGGCAGCTATTTATATACGTGTT TCTACTCAAGAGCAAGTAGAAAATTA TTCAATACAAGCTCAAACTGAAAAAC TAACAGGATTGTGCCGCTCGAAGGAC TGGGACGTATACGATATTTTCATTGAC GGCGGATACTCCGGCTCAAATATGAA TCGTCCCGCATTAAATGAAATGCTAA | (62) | 5 |

TABLE 2-continued

Relevant input plasmid parts and their sequences.

| Part name | Type | Notes | Sequence | Derived from | SEQ ID NO |
|---|---|---|---|---|---|
| | | | GTAAACTACACGAAATTGATGCTGTA<br>GTCGTATATCGATTAGACAGACTATC<br>CCGCTCACAAAGAGACACAATAACGC<br>TTATTGAAGAATACTTCTTAAAAAAC<br>AATGTAGAGTTTGTTAGTTTGTCTGAA<br>ACGCTTGATACTAGTTCCCCTTTCGGT<br>CGTGCAATGATTGGTATATTATCAGTA<br>TTCGCACAGCTAGAGCGCGAAACAAT<br>CCGAGATCGTATGGTGATGGGGAAAA<br>TTAAGCGTATTGAAGCAGGTCTTCCGT<br>TAACAACTGCGAAAGGTAGAACGTTC<br>GGCTATGATGTTATAGATACAAAATT<br>ATACATTAATGAAGAAGAAGCAAAAC<br>AGTTACAACTGATTTATGATATTTTCG<br>AAGAAGAACAAAGTATAACTTTTTTA<br>CAGAAAAGACTAAAAAAATTAGGCTT<br>TAAAGTTAGAACATATAATCGCTATA<br>ACAACTGGCTAACTAATGATTTGTATT<br>GTGGTTATGTTTCATATAAAGATAAA<br>GTTCATGTAAAAGGTATTCATGAACC<br>TATCATCAGTGAAGAGCAATTCTATA<br>GAGTTCAAGAAATATTTACTCGTATG<br>GGTAAAAATCCGAACATGAATAGAGA<br>TTCAGCATCGTTGCTAAATAATTTAGT<br>AGTTTGTAGTAAATGCGGGTTAGGCT<br>TTGTTCATCGTAGAAAAGATACAATG<br>TCGCGTGGTAAAAAATATCATTATAG<br>ATATTATAGTTGCAAGACTTATAAAC<br>ATACTCATGAACTCGAAAAATGCGGG<br>AATAAAATTTGGAGAGCTGACAAACT<br>TGAAGAATTAATTATTAATCGTGTGA<br>ATAATTATAGTTTCGCTTCCAGAAATG<br>TAGATAAAGAAGATGAATTAGATAGC<br>TTAAATGAAAAGCTTAAAATAGAACA<br>TGCAAAGAAAAACGATTATTTGATT<br>TATATATAAATGGCTCGTATGAAGTTT<br>CAGAACTTGATTCTATGATGAATGAT<br>ATTGATGCTCAAATTAATTATTATGAA<br>TCACAAATAGAAGCTAACGAAGAATT<br>GAAGAAAAACAAAAGATACAAGAA<br>AATTTAGCTGATTTAGCAACAGTTGAT<br>TTTGACTCTTTAGAGTTCAGAGAAAA<br>GCAACTTTATTTAAAATCACTAATAA<br>ACAAAATTTATATTGATGGTGAACAA<br>GTTACTATTGAATGGCTCTAG | | |
| phlF | gene | | ATGGCACGTACCCCGAGCCGTAGCAG<br>CATTGGTAGCCTGCGTAGTCCGCATA<br>CCCATAAAGCAATTCTGACCAGCACC<br>ATTGAAATCCTGAAAGAATGTGGTTA<br>TAGCGGTCTGAGCATTGAAAGCGTTG<br>CACGTCGTGCCGGTGCAAGCAAACCG<br>ACCATTTATCGTTGGTGGACCAATAA<br>AGCAGCACTGATTGCCGAAGTGTATG<br>AAAATGAAAGCGAACAGGTGCGTAA<br>ATTTCCGGATCTGGGTAGCTTTAAAGC<br>CGATCTGGATTTTCTGCTGCGTAATCT<br>GTGGAAAGTTTGGCGTGAAACCATTT<br>GTGGTGAAGCATTTCGTTGTGTTATTG<br>CAGAAGCACAGCTGGACCCTGCAACC<br>CTGACCCAGCTGAAAGATCAGTTTAT<br>GGAACGTCGTCGTGAGATGCCGAAAA<br>AACTGGTTGAAAATGCCATTAGCAAT<br>GGTGAACTGCCGAAAGATACCAATCG<br>TGAACTGCTGCTGGATATGATTTTTGG<br>TTTTTGTTGGTATCGCCTGCTGACCGA<br>ACAGCTGACCGTTGAACAGGATATTG<br>AAGAATTTACCTTCCTGCTGATTAATG<br>GTGTTTGTCCGGGTACACAGCGTTAA | (36) | 6 |
| araC | gene | | ATGCAATATGGACAATTGGTTTCTTCT<br>CTGAATGGCGGGAGTATGAAAAGTAT<br>GGCTGAAGCGCAAAATGATCCCCTGC<br>TGCCGGGATACTCGTTTAATGCCCATC | (22) | 7 |

TABLE 2-continued

Relevant input plasmid parts and their sequences.

| Part name | Type | Notes | Sequence | Derived from | SEQ ID NO |
|---|---|---|---|---|---|
| | | | TGGTGGCGGGTTTAACGCCGATTGAG<br>GCCAACGGTTATCTCGATTTTTTTATC<br>GACCGACCGCTGGGAATGAAAGGTTA<br>TATTCTCAATCTCACCATTCGCGGTCA<br>GGGGGTGGTGAAAAATCAGGGACGA<br>GAATTTGTTTGCCGACCGGGTGATATT<br>TTGCTGTTCCCGCCAGGAGAGATTCAT<br>CACTACGGTCGTCATCCGGAGGCTCG<br>CGAATGGTATCACCAGTGGGTTTACTT<br>TCGTCCGCGCGCCTACTGGCATGAAT<br>GGCTTAACTGGCCGTCAATATTTGCCA<br>ATACGGGGTTCTTTCGCCCGGATGAA<br>GCGCACCAGCCGCATTTCAGCGACCT<br>GTTTGGGCAAATCATTAACGCCGGGC<br>AAGGGGAAGGGCGCTATTCGGAGCTG<br>CTGGCGATAAATCTGCTTGAGCAATT<br>GTTACTGCGGCGCATGGAAGCGATTA<br>ACGAGTCGCTCCATCCACCGATGGAT<br>AATCGGGTACGCGAGGCTTGTCAGTA<br>CATCAGCGATCACCTGGCAGACAGCA<br>ATTTTGATATCGCCAGCGTCGCACAG<br>CATGTTTGCTTGTCGCCGTCGCGTCTG<br>TCACATCTTTTCCGCCAGCAGTTAGGG<br>ATTAGCGTCTTAAGCTGGCGCGAGGA<br>CCAACGTATCAGCCAGGCGAAGCTGC<br>TTTTGAGCACCACCCGGATGCCTATCG<br>CCACCGTCGGTCGCAATGTTGGTTTTG<br>ACGATCAACTCTATTTCTCGCGGGTAT<br>TTAAAAAATGCACCGGGGCCAGCCCG<br>AGCGAGTTCCGTGCCGGTTGTGAAGA<br>AAAAGTGAATGATGTAGCCGTCAAGT<br>TGTCATAA | | |
| P<sub>PhlF</sub> | promoter | Induced by DAPG | TCTGATTCGTTACCAATTGACATGATA<br>CGAAACGTACCGTATCGTTAAGGT | (36) | 8 |
| P<sub>BAD</sub> | promoter | Induced by Ara | ACATTGATTATTTGCACGGCGTCACAC<br>TTTGCTATGCCATAGCATTTTTATCCA<br>TAAGATTAGCGGATCCTACCTGACGC<br>TTTTTATCGCAACTCTCTACTGTTTCTC<br>CATACCGTTTTTTTGGGCTAGC | (22) | 9 |
| P<sub>LtetO</sub> | promoter | Induced by ATc | TCCCTATCAGTGATAGAGATTGACAT<br>CCCTATCAGTGATAGAGATACTGAGC<br>AC | (22) | 10 |

TABLE 3

Relevant output plasmid parts and their sequences.

| Part name | Type | Notes | Sequence | Derived From | SEQ ID NO |
|---|---|---|---|---|---|
| gfpmut3b | gene | GFP | ATGAGTAAAGGAGAAGAACTTTTC<br>ACTGGAGTTGTCCCAATTCTTGTTG<br>AATTAGATGGTGATGTTAATGGGC<br>ACAAATTTTCTGTCAGTGGAGAGG<br>GTGAAGGTGATGCAACATACGGAA<br>AACTTACCCTTAAATTTATTTGCAC<br>TACTGGAAAACTACCTGTTCCATG<br>GCCAACACTTGTCACTACTTTCGGT<br>TATGGTGTTCAATGCTTTGCGAGAT<br>ACCCAGATCATATGAAACAGCATG<br>ACTTTTTCAAGAGTGCCATGCCCGA<br>AGGTTATGTACAGGAAAGAACTAT<br>ATTTTTCAAAGATGACGGGAACTA<br>CAAGACACGTGCTGAAGTCAAGTT<br>TGAAGGTGATACCCTTGTTAATAG<br>AATCGAGTTAAAAGGTATTGATTTT<br>AAAGAAGATGGAAACATTCTTGGA | (56) | 11 |

TABLE 3-continued

Relevant output plasmid parts and their sequences.

| Part name | Type | Notes | Sequence | Derived From | SEQ ID NO |
|---|---|---|---|---|---|
| | | | CACAAATTGGAATACAACTATAAC TCACACAATGTATACATCATGGCA GACAAACAAAAGAATGGAATCAA AGTTAACTTCAAAATTAGACACAA CATTGAAGATGGAAGCGTTCAACT AGCAGACCATTATCAACAAAATAC TCCAATTGGCGATGGCCCTGTCCTT TTACCAGACAACCATTACCTGTCCA CACAATCTGCCCTTTCGAAGATCC CAACGAAAAGAGAGACCACATGGT CCTTCTTGAGTTTGTAACAGCTGCT GGGATTACACATGGCATGGATGAT CTCTACAAATAA | | |
| mtagbfp | gene | BFP | ATGAGCGAGCTGATTAAGGAGAAC ATGCACATGAAGCTGTACATGGAG GGCACCGTGGACAACCATCACTTC AAGTGCACATCCGAGGGCGAAGGC AAGCCCTACGAGGGCACCCAGACC ATGAGAATCAAGGTGGTCGAGGGC GGCCCTCTCCCCTTCGCCTTCGACA TCCTGGCTACTAGCTTCCTCTACGG CAGCAAGACCTTCATCAACCACAC CCAGGGCATCCCCGACTTCTTCAA GCAGTCCTTCCCTGAGGGCTTCACA TGGGAGAGAGTCACCACATACGAA GACGGGGGCGTGCTGACCGCTACC CAGGACACCAGCCTCCAGGACGGC TGCCTCATCTACAACGTCAAGATC AGAGGGGTGAACTTCACATCCAAC GGCCCTGTGATGCAGAAGAAAACA CTCGGCTGGGAGGCCTTCACCGAG ACGCTGTACCCCGCTGACGGCGGC CTGGAAGGCAGAAACGACATGGCC CTGAAGCTCGTGGGCGGGAGCCAT CTGATCGCAAACATCAAGACCACA TATAGATCCAAGAAACCCGCTAAG AACCTCAAGATGCCTGGCGTCTAC TATGTGGACTACAGACTGGAAAGA ATCAAGGAGGCCAACAACGAGACC TACGTCGAGCAGCACGAGGTGGCA GTGGCCAGATACTGCGACCTCCCT AGCAAACTGGGGCACTAA | (58) | 12 |
| mrfp | gene | RFP | ATGTCCAGATTAGATAAAAGTAAA GTTGCGAGCTCTGAAGACGTTATC AAAGAGTTCATGCGTTTCAAAGTT CGTATGGAAGGTTCCGTTAACGGT CACGAGTTCGAAATCGAAGGTGAA GGTGAAGGTCGTCCGTACGAAGGT ACCCAGACCGCTAAACTGAAAGTT ACCAAAGGTGGTCCGCTGCCGTTC GCTTGGGACATCCTGTCCCCGCAGT TCCAGTACGGTTCCAAAGCTTACGT TAAACACCCGGCTGACATCCCGGA CTACCTGAAACTGTCCTTCCCGGAA GGTTTCAAATGGGAACGTGTTATG AACTTCGAAGACGGTGGTGTTGTT ACCGTTACCCAGGACTCCTCCCTGC AAGACGGTGAGTTCATCTACAAAG TTAAACTGCGTGGTACCAACTTCCC GTCCGACGGTCCGGTTATGCAGAA AAAAACCATGGGTTGGGAAGCTTC CACCGAACGTATGTACCCGGAAGA CGGTGCTCTGAAAGGTGAAATCAA AATGCGTCTAAAACTGAAAGACGG TGGTCACTACGACGCTGAAGTTAA AACCACCTACATGGCTAAAAAACC GGTTCAGCTGCCGGGTGCTTACAA AACCGACATCAAACTGGACATCAC CTCCCACAACGAAGACTACACCAT CGTTGAACAGTACGAACGTGCTGA AGGTCGTCACTCCACCGGTGCTTA ATAA | (57) | 13 |

TABLE 3-continued

Relevant output plasmid parts and their sequences.

| Part name | Type | Notes | Sequence | Derived From | SEQ ID NO |
|---|---|---|---|---|---|
| BxbIB-CA | attB | CA dinucleotide | CGGCCGGCTTGTCGACGACGGCGC ACTCCGTCGTCAGGATCATCCGGG C | | 14 |
| BxbIP-CA | attP | CA dinucleotide | GTCGTGGTTTGTCTGGTCAACCACC GCGCACTCAGTGGTGTACGGTACA AACCCCGAC | | 15 |
| BxbIB-GT | attB | GT dinucleotide | CGGCCGGCTTGTCGACGACGGCGG TCTCCGTCGTCAGGATCATCCGGGC | (21) | 16 |
| BxbIP-GT | attP | GT dinucleotide | GTCGTGGTTTGTCTGGTCAACCACC GCGGTCTCAGTGGTGTACGGTACA AACCCCGAC | (21) | 17 |
| TP901B-AG | attB | AG dinucleotide | ATGCCAACACAATTAACATCAGAA TCAAGGTAAATGCTTTTTGCTTTTT TTGC | | 18 |
| TP901P-AG | attP | AG dinucleotide | GCGAGTTTTTATTTCGTTTATTAGA ATTAAGGTAACTAAAAAACTCCTT T | | 19 |
| TP901B-TC | attB | TC dinucleotide | ATGCCAACACAATTAACATCTCAA TCAAGGTAAATGCTTTTTGCTTTTT TTGC | (22) | 20 |
| TP901P-TC | attP | TC dinucleotide | GCGAGTTTTTATTTCGTTTATTTCA ATTAAGGTAACTAAAAAACTCCTT T | (22) | 21 |
| A118B-AA | attB | AA dinucleotide | AACTTTTCGGATCAAGCTATGAAA AACGCAAAGAGGGAACTAAACACT T | | 22 |
| A118P-AA | attP | AA dinucleotide | TTAGTTCCTCGTTTTCTCTCGTTAA AAGAAGAAGAAACGAGAAACTAA A | | 23 |
| A118B-GG | attB | GG dinucleotide | AACTTTTCGGATCAAGCTATGAAG GACGCAAAGAGGGAACTAAACACT T | (62) | 24 |
| A118P-GG | attP | GG dinucleotide | TTAGTTCCTCGTTTTCTCTCGTTGG AAGAAGAAGAAACGAGAAACTAA A | (62) | 25 |
| proD | promoter | | CACAGCTAACACCACGTCGTCCCT ATCTGCTGCCCTAGGTCTATGAGTG GTTGCTGGATAACTTTACGGGCAT GCATAAGGCTCGTATAATATATTC AGGGAGACCACAACGGTTTCCCTC TACAAATAATTTTGTTTAACTTT | (51) | 26 |
| proNR3 | promoter | BBa_R0051 fused upstream of the ITS sequence ATATAGTG AACAAGGA TTAA (SEQ ID NO: 1) | TAACACCGTGCGTTTGACTATTTTA CCTCTGGCGGTGATAATGGTTGCAT ATAGTGAACAAGGATTAA | BBa_R0051 (53) ITS (54) | 27 |
| proNR4 | promoter | BBa_J54200 fused upstream of the ITS sequence ATAGGTTA AAAGCCAG ACAT (SEQ ID NO: 2) | CCGTGACGGATCCTGGTGCAAAAC CTTTCGCGGTATGGCATGATAGCG CCATAGGTTAAAAGCCAGACAT | BBa_J54200 (53) ITS (54) | 28 |

TABLE 3-continued

Relevant output plasmid parts and their sequences.

| Part name | Type | Notes | Sequence | Derived From | SEQ ID NO |
|---|---|---|---|---|---|
| BBa_B0062-R | terminator | used for insulating the register | CAGATAAAAAAATCCTTAGCTTT CGCTAAGGATGATTTCT | (55) | 29 |
| ECK1200 10850 | terminator | used for insulating the register | AGTTAACCAAAAAGGGGGATTTT ATCTCCCCTTTAATTTTTCCT | (55) | 30 |
| ECK1200 10825 | terminator | used for insulating the register | ATCTCCTTTCACGGCCCATTCCTCA TGGATGGGCCGTTTATTTCCC | (55) | 31 |
| ECK1200 30221 | terminator | used for insulating the register | CCCGCACTTAACCCGCTTCGGCGG GTTTTTGTTTTT | (55) | 32 |
| ECK1200 10799 | terminator | used for insulating the register | GTTATGAGTCAGGAAAAAAGGCGA CAGAGTAATCTGTCGCCTTTTTTCT TTGCTTGCTTT | (55) | 33 |
| ECK1200 10818 | terminator | used for insulating the register | GTCAGTTTCACCTGTTTTACGTAAA AACCCGCTTCGGCGGGTTTTTACTT TTGG | (55) | 34 |
| ECK1200 33737 | terminator | | GGAAACACAGAAAAAAGCCCGCA CCTGACAGTGCGGGCTTTTTTTTC GACCAAAGG | (55) | 35 |
| BBa_B0010 | terminator | | CCAGGCATCAAATAAAACGAAAGG CTCAGTCGAAAGACTGGGCCTTTC GTTTTATCTGTTGTTTGTCGGTGAA CGCTCTC | (55) | 36 |
| ECK1200 29600 | terminator | | TTCAGCCAAAAAACTTAAGACCGC CGGTCTTGTCCACTACCTTGCAGTA ATGCGGTGGACAGGATCGGCGGTT TTCTTTTCTCTTCTCAA | (55) | 37 |
| ECK1200 33736 | terminator | | AACGCATGAGAAAGCCCCCGGAAG ATCACCTTCCGGGGGCTTTTTTATT GCGC | (55) | 38 |
| ECK1200 16586 | terminator | | AAGAACGAGTAAAAGGTCGGTTTA ACCGGCCTTTTATTTTGTGA | (55) | 39 |
| ilvBN | terminator | | AAGACCCCGCACCGAAAGGTCCG GGGGTTTTTTTT | (55) | 40 |
| ECK1200 10782 | terminator | | ACCTGTAAAAAAGGCAGCCATCTG GCTGCCTTAGTCTCCCCA | (55) | 41 |
| ECK1200 15440 | terminator | | TCCGGCAATTAAAAAAGCGGCTAA CCACGCCGCTTTTTTTACGTCTGCA | (55) | 42 |
| ECK1200 10876 | terminator | | TAAGGTTGAAAAATAAAAACGGCG CTAAAAAGCGCCGTTTTTTTGACG GTGGTA | (55) | 43 |
| ECK1200 15170 | terminator | | ACAATTTTCGAAAAACCCGCTTC GGCGGGTTTTTTATAGCTAAAA | (55) | 44 |
| pyrBI | terminator | | AGCCCCTCAATCGAGGGGCTTTTTT TTGC | (55) | 45 |
| ECK1200 26481 | terminator | | TACCACCGTCAAAAAAAACGGCGC TTTTTAGCGCCGTTTTTATTTTTCAA CCTT | (55) | 46 |
| ECK1200 15444 | terminator | | ACATTTAATAAAAAAAGGGCGGTC GCAAGATCGCCCTTTTTTACGTATG ACA | (55) | 47 |

TABLE 3-continued

Relevant output plasmid parts and their sequences.

| Part name | Type | Notes | Sequence | Derived From | SEQ ID NO |
|---|---|---|---|---|---|
| ECK1200 16882 | terminator | | TGTGAAAAAGCCCGCGCAAGCGGG TTTTTTTATG | (55) | 48 |

TABLE 4

RSMs and the plasmids used to implement them.

Figure 6C:
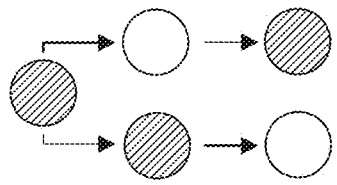
Figure 6D:
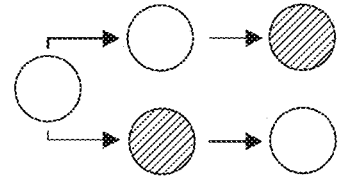
Figure 6E:
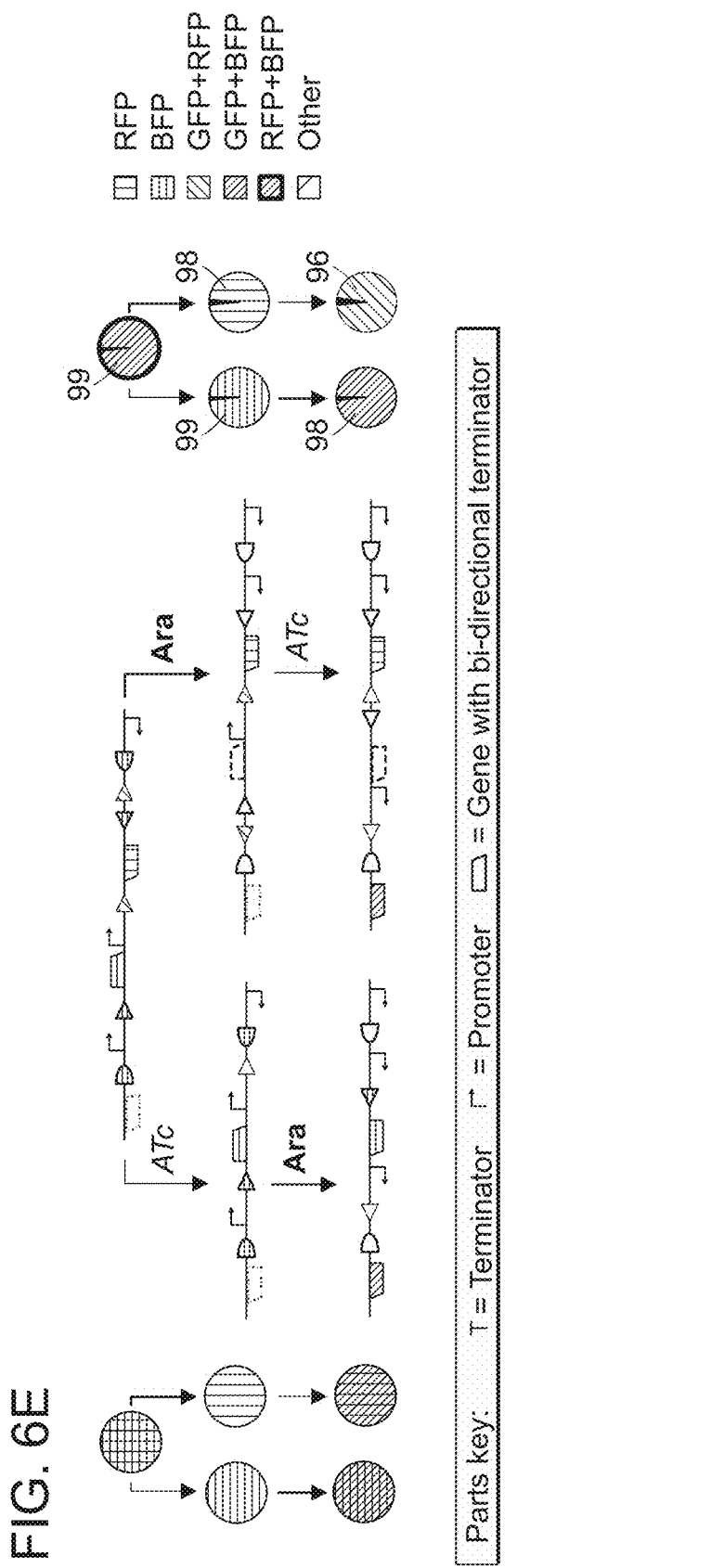

| RSM | Input plasmid | Output plasmid |
|---|---|---|
| FIG. 3A | pNR64 | pNR160 |
| FIG. 4A | pNR220 | pNR188 |
| FIG. 6A | pNR64 | pNR163 |
| FIG. 6B | pNR64 | pNR186 |
| FIG. 6C | pNR64 | pNR165 |
| FIG. 6D | pNR64 | pNR164 |
| FIG. 6E | pNR64 | pNR291 |
| FIG. 7A | pNR220 | pNR292 |
| FIG. 7B | pNR220 | pNR284 |
| FIG. 17A | pNR64 | pNR166 |
| FIG. 17B | pNR64 | pNR187 |

TABLE 5

Quantitative-PCR primers used to interrogate the 2-input, 5-state RSM from FIG. 3A. The first column identifies the primer by the DNA region of the register to which it binds (r1-r7, corresponding to FIG. 19) and the direction in which it binds it ("F" for forward and "R" for reverse). The second column gives the primer pair to which it belongs (corresponding to FIG. 19). The primers in pair "ppN" are used for normalization- they bind the backbone of the output plasmids.

| Primer | Primer pair | Name | Sequence | SEQ ID NO |
|---|---|---|---|---|
| r3-F | pp1 | NR346 | TCGTCCGTGACA TTCTGTGCG | 49 |
| r4-R | pp1 | NR347 | CTTCTGGCATAG ACAGCCGCTG | 50 |
| r1-F | pp2 | NR342 | GAGTGCGGTATT CCTCTGGGC | 51 |
| r6-F | pp2 | NR352 | CATAGCCAGCCT GACAGTAGCC | 52 |
| r3-R | pp3 | NR345 | CGCCATTCCCTA GTGAGCCC | 53 |
| r5-R | pp3 | NR349 | CATGTCATGTCG CGCGAACG | 54 |
| normal- ization | ppN | NR444 | CCAATATGGACA ACTTCTTCGCCC | 55 |
| normal- ization | ppN | NR445 | ATGGAAGCCATC ACAAACGGC | 56 |

TABLE 6

Quantitative-PCR primers used to interrogate the 3-input, 16-state RSM from FIG. 4A. The first column identifies the primer by the DNA region of the register to which it binds (r1-r13, corresponding to FIG. 20) and the direction in which it binds it ("F" for forward and "R" for reverse). The second column gives the primer pair to which it belongs (corresponding to FIG. 20). The primers in pair "ppN" are used for normalization- they bind the backbone of the output plasmid.

| Primer | Primer pair | Name | Sequence | SEQ ID NO |
|---|---|---|---|---|
| r10-F | pp1 | NR360 | ACTCGCGCTTCGT CGACAC | 57 |
| r11-R | pp1 | NR361 | TGAACTGCAGCCT CAGGGACG | 58 |
| r6-F | pp2 | NR352 | CATAGCCAGCCTG ACAGTAGCC | 59 |
| r7-R | pp2 | NR353 | ACTGTGTCGCTCT CAGCTGC | 60 |
| r6-R | pp3 | NR351 | GTGCATGGTTGGC GCTATTGC | 61 |
| r8-R | pp3 | NR355 | ATGGCCTACCTGC ACCCCAAG | 62 |
| r2-R | pp4 | NR343 | GGTAGCTAGATCC GCACCACG | 63 |
| r4-R | pp4 | NR347 | CTTCTGGCATAGA CAGCCGCTG | 64 |
| r4-F | pp5 | NR348 | TCGGTCAGGTCGG AGTCCTAG | 65 |
| r5-R | pp5 | NR349 | CATGTCATGTCGC GCGAACG | 66 |
| r10-R | pp6 | NR359 | CGGAACCTACACT AAGGAGATCCGG | 67 |
| r12-R | pp6 | NR634 | CACCTGGTCTACC TGTCGATCTG | 68 |
| normal- ization | ppN | NR444 | CCAATATGGACAA CTTCTTCGCCC | 69 |
| normal- ization | ppN | NR445 | ATGGAAGCCATCA CAAACGGC | 70 |

TABLE 7

GRSM database search function input and output objects used to design the 2-input, 5-state GRSMs. The inputs are matrices (comma-separated columns, and semi-colon-separated rows) and the outputs are vectors, as per the GRSM search function instructions in Example 15. The inputs can be pasted directly into the search function, and the registers are direct outputs.

| GRSM | gene regulation program (input) | register (output) |
| --- | --- | --- |
| FIG. 6A | [1; 0; 1; 1; 0] | [14, −1, 5, 5, −3, 5, 5] |
| FIG. 6B | [0; 0; 1; 1; 0] | [5, 5, 6, 5, 15, 15, 1] |
| FIG. 6C | [1; 1; 0; 0; 1] | [−1, −14, 5, 5, −14, 5, 5] |
| FIG. 6D | [0; 1; 0; 0; 1] | [14, 5, 5, 5, −3, 1, 5] |
| FIG. 6E | [1, 0, 1; 1, 0, 0; 0, 0, 1; 1, 1, 0; 0, 1, 1] | [−1, 14, 2, −1, 5, 5, −14] |
| FIG. 17A | [0; 0; 1; 1; 0] | [5, 5, 1, −15, 5, −14, −14] |
| FIG. 17B | [0; 0; 1; 1; 0] | [−1, 14, 5, −15, 14, 5, 5] |

TABLE 8

GRSM database part functions. All parts used to build the database. Parts are given by their ID in the left column corresponding to Table 9 (negative IDs refer to parts in inverse orientation). The function of each part on a register is specified by columns 2-5. (Column 2) Does the part provide a constitutively transcribed gene: no (N) or yes (Y). (Column 3) Does the part provide a gene that can be transcribed from another region of the register: no (N), yes from the left (L), yes from the right (R), yes from both sides (B). (Column 4) Does the part prevent transcription from moving out of it: no (N), yes to the left (L), yes to the right (R), yes to both sides (B). (Column 5) Does the part initiate transcription out of it: no (N), yes to the left (L), yes to the right (R), yes to both sides (B).

| Part ID | Provides constitutive gene? | Provides non-constitutive gene? | Prevents transcription moving out of it? | Initiates transcription moving out of it? |
| --- | --- | --- | --- | --- |
| 1 | N | L | B | N |
| −1 | N | R | B | N |
| 2 | N | L | L | R |
| −2 | N | R | R | L |
| 3 | N | N | L | R |
| −3 | N | N | R | L |
| 4 | N | N | B | N |
| 5 | N | N | N | N |
| 6 | N | N | N | B |
| 7 | N | N | R | N |
| −7 | N | N | L | N |
| 8 | N | B | B | N |
| 9 | N | R | L | R |
| −9 | N | L | R | L |
| 10 | N | N | N | R |
| −10 | N | N | N | L |
| 11 | N | L | N | B |
| −11 | N | R | N | B |
| 12 | N | B | L | R |
| −12 | N | B | R | L |
| 13 | N | B | N | B |
| 16 | Y | L | B | N |
| −16 | Y | R | B | N |
| 17 | Y | L | L | R |
| −17 | Y | R | R | L |
| 18 | Y | N | L | R |
| −18 | Y | N | R | L |
| 19 | Y | N | B | N |
| 20 | Y | N | N | B |
| 21 | Y | B | B | N |
| 22 | Y | R | L | R |
| −22 | Y | L | R | L |
| 23 | Y | L | N | B |
| −23 | Y | R | N | B |
| 24 | Y | B | L | R |
| −24 | Y | B | R | L |
| 25 | Y | B | N | B |

REFERENCES

1. J. E. Hopcroft, J. D. Ullman, *Introduction to Automata Theory, Languages, and Computation* (Addison Wesley, ed. 1, 1979).
2. S. M. Kaech, W. Cui, Transcriptional control of effector and memory $CD8_+$ T cell differentiation. *Nat. Rev. Immunol.* 12, 749-761 (2012).
3. N. Yosef et al., Dynamic regulatory network controlling TH17 cell differentiation. *Nature.* 496, 461-468 (2013).
4. S. Agarwal, K. L. Holton, R. Lanza, Efficient Differentiation of Functional Hepatocytes from Human Embryonic Stem Cells. *Stem Cells.* 26, 1117-1127 (2008).
5. C. E. Murry, G. Keller, Differentiation of embryonic stem cells to clinically relevant populations: lessons from embryonic development. *Cell.* 132, 661-680 (2008).
6. T. Brambrink et al., Sequential Expression of Pluripotency Markers during Direct Reprogramming of Mouse Somatic Cells. *Cell Stem Cell.* 2, 151-159 (2008).
7. R. Jaenisch, R. Young, Stem Cells, the Molecular Circuitry of Pluripotency and Nuclear Reprogramming. *Cell.* 132, 567-582 (2008).
8. C. A. Ortmann et al., Effect of Mutation Order on Myeloproliferative Neoplasms. *N. Engl. J. Med.* 372, 601-612 (2015).
9. E. Fokas, W. G. McKenna, R. J. Muschel, The impact of tumor microenvironment on cancer treatment and its modulation by direct and indirect antivascular strategies. *Cancer Metastasis Rev.* 31, 823-842 (2012).
10. A. N. Hata et al., Tumor cells can follow distinct evolutionary paths to become resistant to epidermal growth factor receptor inhibition. *Nat. Med.* 22, 262-269 (2016).
11. J. Shah, P. T. Desai, D. Chen, J. R. Stevens, B. C. Weimer, Preadaptation to cold stress in *Salmonella enterica* serovar *typhimurium* increases survival during subsequent acid stress exposure. *Appl. Environ. Microbiol.* 79, 7281-7289 (2013).
12. R. Roemhild, C. Barbosa, R. E. Beardmore, G. Jansen, H. Schulenburg, Temporal variation in antibiotic environments slows down resistance evolution in pathogenic *Pseudomonas aeruginosa. Evol. Appl.* 8, 945-955 (2015).
13. Y. Benenson, Biomolecular computing systems: principles, progress and potential. *Nat. Rev. Genet.* 13, 455-468 (2012).
14. K. Oishi, E. Klavins, Framework for engineering finite state machines in gene regulatory networks. *ACS Synth. Biol.* 3, 652-665 (2014).

15. J. Bonnet, P. Subsoontorn, D. Endy, Rewritable digital data storage in live cells via engineered control of recombination directionality. *Proc. Natl. Acad. Sci. U.S.A* 109, 8884-8889 (2012).
16. T. S. Ham, S. K. Lee, J. D. Keasling, A. P. Arkin, Design and construction of a double inversion recombination switch for heritable sequential genetic memory. *PLoS One.* 3, e2815 (2008).
17. T. S. Ham, S. K. Lee, J. D. Keasling, A. P. Arkin, A Tightly Regulated Inducible Expression System Utilizing the fim Inversion Recombination Switch. *Biotechnol. Bioeng.* 94, 1-4 (2006).
18. L. Yang et al., Permanent genetic memory with >1-byte capacity. *Nat. Methods.* 11, 1261-1266 (2014).
19. L. Prochazka, B. Angelici, B. Haefliger, Y. Benenson, Highly modular bow-tie gene circuits with programmable dynamic behaviour. *Nat. Commun.* 5, 4729 (2014).
20. A. E. Friedland et al., Synthetic gene networks that count. *Science.* 324, 1199-1202 (2009).
21. P. Siuti, J. Yazbek, T. K. Lu, Synthetic circuits integrating logic and memory in living cells. *Nat. Biotechnol.* 31, 448-452 (2013).
22. J. Bonnet, P. Yin, M. E. Ortiz, P. Subsoontorn, D. Endy, Amplifying Genetic Logic Gates. *Science.* 340, 599-603 (2013).
23. V. Hsiao, Y. Hori, P. W. K. Rothemund, R. M. Murray, "A population-based temporal logic gate for timing and recording chemical events" (2015), bioRxiv doi:10.1101/029967.
24. N. D. F. Grindley, K. L. Whiteson, P. A. Rice, Mechanisms of site-specific recombination. *Annu. Rev. Biochem.* 75, 567-605 (2006).
25. W. R. A. Brown, N. C. O. Lee, Z. Xu, M. C. M. Smith, Serine recombinases as tools for genome engineering. *Methods.* 53, 372-379 (2011).
26. H. M. Thorpe, M. C. Smith, In vitro site-specific integration of bacteriophage DNA catalyzed by a recombinase of the resolvase/invertase family. *Proc. Natl. Acad. Sci. U.S.A.* 95, 5505-5510 (1998).
27. P. Ghosh, N. R. Pannunzio, G. F. Hatfull, M. Gottesman, Synapsis in phage Bxb1 integration: Selection mechanism for the correct pair of recombination sites. *J. Mol. Biol.* 349, 331-348 (2005).
28. P. A. Rowley, M. C. A. Smith, E. Younger, M. C. M. Smith, A motif in the C-terminal domain of PhiC31 integrase controls the directionality of recombination. *Nucleic Acids Res.* 36, 3879-3891 (2008).
29. M. C. A. Smith, R. Till, M. C. M. Smith, Switching the polarity of a bacteriophage integration system. *Mol. Microbiol.* 51, 1719-1728 (2004).
30. P. Ghosh, L. A. Bibb, G. F. Hatfull, Two-step site selection for serine-integrase-mediated excision: DNA-directed integrase conformation and central dinucleotide proofreading. *Proc. Natl. Acad. Sci. U.S.A* 105, 3238-3243 (2008).
31. S. D. Colloms et al., Rapid metabolic pathway assembly and modification using serine integrase site-specific recombination. *Nucleic Acids Res.* 42, e23 (2013).
32. See Materials and Methods section below.
33. B. Wang, R. I. Kitney, N. Joly, M. Buck, Engineering modular and orthogonal genetic logic gates for robust digital-like synthetic biology. *Nat. Commun.* 2, 508 (2011).
34. R. Gaber et al., Designable DNA-binding domains enable construction of logic circuits in mammalian cells. *Nat. Chem. Biol.* 10, 203-208 (2014).
35. J. J. Lohmueller, T. Z. Armel, P. A. Silver, A tunable zinc finger-based framework for Boolean logic computation in mammalian cells. *Nucleic Acids Res.* 40, 5180-5187 (2012).
36. A. A. Nielsen, C. A. Voigt, Multi-input CRISPR/Cas genetic circuits that interface host regulatory networks. *Mol. Syst. Biol.* 10, 763 (2014).
37. S. Regot et al., Distributed biological computation with multicellular engineered networks. *Nature.* 469, 207-211 (2011).
38. T. S. Moon, C. Lou, A. Tamsir, B. C. Stanton, C. A. Voigt, Genetic programs constructed from layered logic gates in single cells. *Nature.* 491, 249-253 (2012).
39. A. Tamsir, J. J. Tabor, C. A. Voigt, Robust multicellular computing using genetically encoded NOR gates and chemical "wires". *Nature.* 469, 212-5 (2011).
40. M. N. Win, C. D. Smolke, Higher-order cellular information processing with synthetic RNA devices. *Science.* 322, 456-460 (2008).
41. W. S. Teo, M. W. Chang, Development and characterization of AND-gate dynamic controllers with a modular synthetic GAL1 core promoter in *Saccharomyces cerevisiae*. *Biotechnol. Bioeng.* 111, 144-151 (2014).
42. S. Ausländer, D. Ausländer, M. Müller, M. Wieland, M. Fussenegger, Programmable single-cell mammalian biocomputers. *Nature.* 487, 123-127 (2012).
43. J. M. Callura, D. J. Dwyer, F. J. Isaacs, C. R. Cantor, J. J. Collins, Tracking, tuning, and terminating microbial physiology using synthetic riboregulators. *Proc. Natl. Acad. Sci. U.S.A* 107, 15898-15903 (2010).
44. J. Hasty, D. McMillen, J. J. Collins, Engineered gene circuits. *Nature.* 420, 224-230 (2002).
45. A. C. Groth, E. C. Olivares, B. Thyagarajan, M. P. Calos, A phage integrase directs efficient site-specific integration in human cells. *Proc. Natl. Acad. Sci. U.S.A* 97, 5995-6000 (2000).
46. E. C. Olivares, R. P. Hollis, M. P. Calos, Phage R4 integrase mediates site-specific integration in human cells. *Gene.* 278, 167-176 (2001).
47. S. M. Stoll, D. S. Ginsburg, M. P. Calos, Phage TP901-1 Site-Specific Integrase Functions in Human Cells. *J. Bacteriol.* 184, 3657-3663 (2002).
48. A. Keravala et al., A diversity of serine phage integrases mediate site-specific recombination in mammalian cells. *Mol. Genet. Genomics.* 276, 135-146 (2006).
49. J. Sambrook, E. Fritsch, T. Maniatis, *Molecular Cloning: A Labratory Manual* (Cold Spring Laboratory Press, ed. 2, 1989).
50. D. G. Gibson et al., Enzymatic assembly of DNA molecules up to several hundred kilobases. *Nat. Methods.* 6, 343-344 (2009).
51. J. H. Davis, A. J. Rubin, R. T. Sauer, Design, construction and characterization of a set of insulated bacterial promoters. *Nucleic Acids Res.* 39, 1131-1141 (2011).
52. J. Wild, Z. Hradecna, W. Szybalski, Conditionally Amplifiable BACs: Switching From Single-Copy to High-Copy Vectors and Genomic Clones. *Genome Res.* 12, 1434-1444 (2002).
53. iGem Registry of Standard Biological Parts (parts.igem.org).
54. L. M. Hsu et al., Initial transcribed sequence mutations specifically affect promoter escape properties. *Biochemistry.* 45, 8841-8854 (2006).
55. Y. J. Chen et al., Characterization of 582 natural and synthetic terminators and quantification of their design constraints. *Nat. Methods.* 10, 659-664 (2013).

56. B. P. Cormack, R. H. Valdivia, S. Falkow, FACS-optimized mutants of the green fluorescent protein (GFP). *Gene.* 173, 33-38 (1996).
57. R. E. Campbell et al., A monomeric red fluorescent protein. *Proc. Natl. Acad. Sci. U.S.A.* 99,7877-7882 (2002).
58. O. M. Subach et al., Conversion of Red Fluorescent Protein into a Bright Blue Probe. *Chem. Biol.* 15, 1116-1124 (2008).
59. H. M. Salis, E. A. Mirsky, C. A. Voigt, Automated design of synthetic ribosome binding sites to control protein expression. *Nat. Biotechnol.* 27, 946-950 (2009).
60. C. Lou, B. Stanton, Y. J. Chen, B. Munsky, C. A. Voigt, Ribozyme-based insulator parts buffer synthetic circuits from genetic context. *Nat. Biotechnol.* 30, 1137-1142 (2012).
61. B. P. Callen, K. E. Shearwin, J. B. Egan, Transcriptional Interference between Convergent Promoters Caused by Elongation over the Promoter. *Mol. Cell.* 14, 647-656 (2004).
62. M. J. Loessner, R. B. Inman, P. Lauer, R. Calendar, Complete nucleotide sequence, molecular analysis and genome structure of bacteriophage A118 of *Listeria monocytogenes*: implications for phage evolution. *Mol. Microbiol.* 35, 324-340 (2000).

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed:

1. A system, comprising:
   (a) n serine recombinases, wherein n is greater than 2; and
   (b) an engineered nucleic acid comprising n(n−1) pairs of cognate recombination recognition sites (RRS),
   wherein the n(n−1) pairs of RRSs of (b) are arranged in an overlapping configuration such that the two RRSs of each pair of the n(n−1) pairs of RRSs are separated from each other by at least one RRS of another pair of the n(n−1) pairs of RRSs, and wherein recombination between the two RRSs of each pair of the n(n−1) pairs of RRSs either inverts or excises at least one RRS of another pair of the n(n−1) pairs of RRSs.

2. The system of claim 1, wherein n is greater than or equals 3, 4, 5, 6, 7, 8, 9, 10, 11, 12, 13, 14, 15, 16, 17, 18, 19 or 20.

3. The system of claim 1, wherein the n serine recombinase is selected from Bxb1, Tp901, A118, PhlF and AraC.

4. The system of claim 1, wherein the RRSs are selected from an attB site, an attP site, an attB site modified to include a CA dinucleotide, an attP site modified to include a CA dinucleotide, an attB site modified to include a GT dinucleotide, an attP site modified to include a GT dinucleotide, an attB site modified to include a AG dinucleotide, an attP site modified to include a AG dinucleotide, an attB site modified to include a TC dinucleotide, an attP site modified to include a TC dinucleotide, an attB site modified to include a AA dinucleotide, an attP site modified to include a AA dinucleotide, an attB site modified to include a GG dinucleotide, and an attP site modified to include a GG dinucleotide.

5. The system of claim 1, wherein the system further comprises at least one engineered nucleic acid comprising at least one promoter operably linked to a nucleotide sequence encoding at least one of the n serine recombinases.

6. The system of claim 5, wherein the at least one promoter is inducible.

7. The system of claim 6, wherein the at least one promoter is selected from $P_{PhlF}$, $P_{BAD}$ and $P_{LtetO}$.

8. The system of claim 1, wherein the engineered nucleic acid of (b) further comprises a nucleotide sequence encoding a detectable molecule.

9. The system of claim 8, wherein the detectable molecule is a fluorescent molecule.

10. A system, comprising:
    (a) three serine recombinases; and
    (b) an engineered nucleic acid comprising six pairs of cognate recombinase recognition sites (RRSs),
    wherein the six pairs of RRSs of (b) are arranged in an overlapping configuration such that the two RRSs of each pair of the six pairs of RRSs are separated from each other by at least one RRS of another pair of the six pairs of RRSs, and wherein recombination between the two RRSs of each pair of the six pairs of RRSs either inverts or excises at least one RRS of another pair of the six pairs of RRSs.

11. A system, comprising:
(a) four serine recombinases; and
(b) an engineered nucleic acid comprising twelve pairs of cognate recombinase recognition sites (RRSs),
wherein the twelve pairs of RRSs of (b) are arranged in an overlapping configuration such that the two RRSs of each pair of the twelve pairs of RRSs are separated from each other by at least one RRS of another pair of the twelve pairs of RRSs, and wherein recombination between the two RRSs of each pair of the twelve pairs of RRSs either inverts or excises at least one RRS of another pair of the twelve pairs of RRSs.

12. An isolated cell comprising the system of claim 1.

13. The isolated cell of claim 12, wherein the isolated cell is a bacterial cell or a mammalian cell.

14. The isolated cell of claim 12, wherein the isolated cell is a stem cell.

* * * * *

UNITED STATES PATENT AND TRADEMARK OFFICE
CERTIFICATE OF CORRECTION

PATENT NO. : 10,480,009 B2
APPLICATION NO. : 15/283162
DATED : November 19, 2019
INVENTOR(S) : Timothy Kuan-Ta Lu et al.

It is certified that error appears in the above-identified patent and that said Letters Patent is hereby corrected as shown below:

In the Claims

In Claim 1, at Column 91, Line 41:
"n serine recombinases, wherein n is greater than 2"
Should read:
--$n$ serine recombinases, wherein $n$ is greater than 2--

In Claim 1, at Column 91, Line 42-51:
"an engineered nucleic acid comprising n(n-1) pairs of cognate recombination recognition sites (RRS), wherein the n(n-1) pairs of RRSs of (b) are arranged in an overlapping configuration such that the two RRSs of each pair of the n(n-1) pairs of RRSs are separated from each other by at least one RRS of another pair of the n(n-1) pairs of RRSs, and wherein recombination between the two RRSs of each pair of the n(n-1) pairs of RRSs either inverts or excises at least one RRS of another pair of the n(n-1) pairs of RRSs"
Should read:
--an engineered nucleic acid comprising $n(n-1)$ pairs of cognate recombination recognition sites (RRS),wherein the $n(n-1)$ pairs of RRSs of (b) are arranged in an overlapping configuration such that the two RRSs of each pair of the $n(n-1)$ pairs of RRSs are separated from each other by at least one RRS of another pair of the $n(n-1)$ pairs of RRSs, and wherein recombination between the two RRSs of each pair of the $n(n-1)$ pairs of RRSs either inverts or excises at least one RRS of another pair of the $n(n-1)$ pairs of RRSs--

In Claim 2, at Column 91, Line 52:
"wherein n is greater than or"
Should read:
--wherein $n$ is greater than or--

In Claim 3, at Column 91, Lines 55-56:
"wherein the n serine recombinase"

Signed and Sealed this
Seventeenth Day of March, 2020

Andrei Iancu
*Director of the United States Patent and Trademark Office*

CERTIFICATE OF CORRECTION (continued)
U.S. Pat. No. 10,480,009 B2

Should read:
--wherein the *n* serine recombinase--

In Claim 4, at Column 91, Lines 58-67, and Column 92, Lines 39-40:
"The system of claim 1, wherein the RRSs are selected from an attB site, an attP site, an attB site modified to include a CA dinucleotide, an attP site modified to include a CA dinucleotide, an attB site modified to include a GT dinucleotide, an attP site modified to include a GT dinucleotide, an attB site modified to include a AG dinucleotide, an attP site modified to include a AG dinucleotide, an attB site modified to include a TC dinucleotide, an attP site modified to include a TC dinucleotide, an attB site modified to include a AA dinucleotide, an attP site modified to include a AA dinucleotide, an attB site modified to include a GG dinucleotide, and an attP site modified to include a GG dinucleotide."
Should read:
--The system of claim 1, wherein the RRSs are selected from an *attB* site, an *attP* site, an *attB* site modified to include a CA dinucleotide, an *attP* site modified to include a CA dinucleotide, an *attB* site modified to include a GT dinucleotide, an *attP* site modified to include a GT dinucleotide, an *attB* site modified to include a AG dinucleotide, an *attP* site modified to include a AG dinucleotide, an *attB* site modified to include a TC dinucleotide, an *attP* site modified to include a TC dinucleotide, an *attB* site modified to include a AA dinucleotide, an *attP* site modified to include a AA dinucleotide, an *attB* site modified to include a GG dinucleotide, and an *attP* site modified to include a GG dinucleotide.--

In Claim 5, at Column 92, Line 44:
"at least one of the n serine recombinases"
Should read:
--at least one of the *n* serine recombinases--